US010555936B2

(12) United States Patent
Baskin et al.

(10) Patent No.: US 10,555,936 B2
(45) Date of Patent: Feb. 11, 2020

(54) CHEMOTHERAPEUTIC COMPOSITIONS AND METHODS FOR TREATING HUMAN GLIOMAS

(71) Applicant: The Methodist Hospital, Houston, TX (US)

(72) Inventors: David S. Baskin, Houston, TX (US); Martyn Alun Sharpe, Houston, TX (US)

(73) Assignee: THE METHODIST HOSPITAL, Houston, TX (US)

( * ) Notice: Subject to any disclaimer, the term of this patent is extended or adjusted under 35 U.S.C. 154(b) by 0 days.

(21) Appl. No.: 14/266,729

(22) Filed: Apr. 30, 2014

(65) Prior Publication Data

US 2014/0323513 A1 Oct. 30, 2014

Related U.S. Application Data

(63) Continuation-in-part of application No. PCT/US2012/062850, filed on Oct. 31, 2012.

(60) Provisional application No. 61/553,854, filed on Oct. 31, 2011.

(51) Int. Cl.
| | | |
|---|---|---|
| *A61K 31/44* | (2006.01) | |
| *A61K 31/435* | (2006.01) | |
| *A61K 31/4375* | (2006.01) | |
| *A61K 31/4745* | (2006.01) | |
| *A61K 45/06* | (2006.01) | |
| *A61K 47/48* | (2006.01) | |
| *A61N 5/10* | (2006.01) | |

(52) U.S. Cl.
CPC .......... *A61K 31/44* (2013.01); *A61K 31/435* (2013.01); *A61K 31/4375* (2013.01); *A61K 31/4745* (2013.01); *A61K 45/06* (2013.01); *A61K 47/48061* (2013.01); *A61N 5/10* (2013.01)

(58) Field of Classification Search
None
See application file for complete search history.

(56) References Cited

U.S. PATENT DOCUMENTS

| | | |
|---|---|---|
| 4,913,891 A | 4/1990 | Fowler et al. |
| 5,399,363 A | 3/1995 | Liversidge et al. |
| 5,543,158 A | 8/1996 | Gref et al. |
| 5,612,329 A | 3/1997 | Gallery et al. |
| 5,641,515 A | 6/1997 | Ramtoola |
| 6,197,770 B1 | 3/2001 | Natchus et al. |
| 6,727,361 B2 | 4/2004 | LaPointe et al. |
| 6,946,479 B2 | 9/2005 | Warshakoon et al. |
| 2006/0079532 A1 | 4/2006 | Fu et al. |
| 2006/0171893 A1 | 8/2006 | Zheng et al. |

| | | |
|---|---|---|
| 2007/0275944 A1 | 11/2007 | Sharpe |
| 2009/0197864 A1 | 8/2009 | Li et al. |
| 2011/0110889 A1 | 5/2011 | Ahrendt et al. |

FOREIGN PATENT DOCUMENTS

| | | |
|---|---|---|
| JP | 2009-501147 | 1/2009 |
| WO | WO 1994/029333 | 12/1994 |
| WO | WO 1998/022110 | 5/1998 |
| WO | WO 2011/035332 | 3/2011 |
| WO | WO 2013/151584 | 10/2013 |

OTHER PUBLICATIONS

Gabilondo et al., "Monoamine Oxidase B Activity is Increased in Human Gliomas," Neurochemistry International, Pergamon Press, Oxford, GB, vol. 52, No. 1-2, Dec. 12, 2007, pp. 230-234, XP022386354, ISSN: 0197-0186, DOI: 10.1016/J.NEUINT.2007/05/015.

International Preliminary Report on Patentability and Written Opinion dated May 6, 2013 issued in PCT/US12/62850.

International Search Report dated May 5, 2013 issued in PCT/US12/62850.

Nakao A. et al., "Tetrahydropyridine Derivatives with Inhibitory Activity on the Production of Proinflammatory Cytokines: Part 3," Bioorganic & Medical Chemistry Letters, Pergamon, Elsevier Science, GB, vol. 20, No. 16, Aug. 15, 2010, pp. 4774-4778, XP027172620, ISSN: 0960-894X.

Chinese Fourth Office Action dated Mar. 16, 2017, Application No. 201280064763.1, pp. 4.

Gabilondo, AM et al., "Monoamine oxidase B activity is increased in human gliomas," Neurochemistry International, 52 pp. 230-234, 2008.

Japanese Office Action dated Jun. 27, 2016, Application No. 2014-540047, pp. 6.

Australian Patent Examintation Report No. 1 dated Aug. 23, 2016, Application No. 2012376221, pp. 5.

Albers, AE et al., "Activity-based fluorescent reporters for monoamine oxidases in living cells," Chem. Comm. (Camb.), 44:4647-4649, Nov. 2007.

Baskin, DS et al., "Quantification and calibration of images in fluorescence microscopy," Anal. Biochem., 404(2):118-126, Sep. 2010.

(Continued)

*Primary Examiner* — Samantha L Shterengarts
(74) *Attorney, Agent, or Firm* — Haynes and Boone, LLP

(57) ABSTRACT

Disclosed are compound for targeting chemotherapeutic agents to mammalian mitochondria. Also disclosed are monoamine oxidase-specific compositions, and methods of using them for the selective therapy of mammalian cancers, and in particular, in the treatment of human gliomas. Also disclosed are methods employing the novel targeted chemotherapeutics with one or more conventional anti-cancer therapies, including, for example, radiotherapy, or multi-drug regimens.

36 Claims, 49 Drawing Sheets
(39 of 49 Drawing Sheet(s) Filed in Color)
Specification includes a Sequence Listing.

(56) References Cited

OTHER PUBLICATIONS

Baskin, DS et al., "Quantification of DNase type I ends, DNase type II ends, and modified bases using fluorescently labeled ddUTP, terminal deoxynucleotidyl transferase, and formamidopyrimidine-DNA glycosylase," Biotechniques, 49(1):505-512, Jul. 2010.
Berridge, MV et al., "Tetrazolium dyes as tools in cell biology: New insights into their cellular reduction," Biotechnol. Annu. Rev., 11:127-152, 2005.
Binda, C et al., "Structures of human monoamine oxidase B complexes with selective noncovalent inhibitors: safinamide and coumarin analogs," J. Med. Chem., 50(23):5848-5852, Jun. 2007.
Boveris, A and Chance, B, "The mitochondrial generation of hydrogen peroxide. General properties and effect of hyperbaric oxygen," Biochem. J., 134(3):707-716, Feb. 1973.
Castagnoli, K et al., "The neuronal nitric oxide synthase inhibitor 7-nitroindazole also inhibits the monoamine oxidase-B-catalyzed oxidation of 1-methyl-4-phenyl-1,2,3,6-tetrahydropyridine," Chem. Res. Toxicol., 10(4):364-368, Jan. 1997.
Castagnoli, K et al., "Neuroprotection by (R)-deprenyl and 7-nitroindazole in the MPTP C57BL/6 mouse model of neurotoxicity," Neurobiol., 7(2):135-149, 1999.
Chinese First Office Action dated May 28, 2015, Application No. 201280064763.1, pp. 13.
Chinese Second Office Action dated Jan. 12, 2016, Application No. 201280064763.1, pp. 5.
Chinese Third Office Action dated Jul. 22, 2016, Application No. 201280064763.1, pp. 9.
Colvin, O. M. et al., "Alkylating Agents," Cancer: Principles & Practice of Oncology 7$^{th}$ Edition. Section 4, 1-31, 2005.
Costantini, P. et al., "Mitochondrion as a novel target of anticancer chemotherapy," J Natl Cancer inst., 5;92(13):1042-53, Jul. 2000.
Decker, T and Lohmann-Matthes, ML, "A quick and simple method for the quantitation of lactate dehydrogenase release in measurements of cellular cytotoxicity and tumor necrosis factor (TNF) activity," J. Immunol. Methods, 115(1):61-69, Jun. 1988.
De Colibus, L et al., "Three-dimensional structure of human monoamine oxidase A (MAO A): Relation to the structures of rat MAO A and human MAO B," Proc. Natl. Acad. Sci. USA, 102:12684-12689, May 2005.
Differding, E and Ghosez, L, "Intramolecular Diels-Alder cycloadditions of vinylketenimines: a convergent route to carbazoles and pyridocarbazole alkaloids," Tetrahedron Lett., 26(13):1647-1650, Jan. 1985.
Dröge, W, "Free radicals in the physiological control of cell function," Physiol. Rev., 82(1):47-95, 2002.
Efange, SMN and Boudreau, RJ, "Molecular determinants in the bioactivation of the dopaminergic neurotoxin N-methyl-4-phenyl-1,2,3,6-tetrahydropyridine (MPTP)," J. Comp. Aided Mol. Des., 5(5):405-417, Mar. 1991.
Fierro, A et al., "Similarities between the binding sites of monoamine oxidase (MAO) from different species—is Zebrafish a useful model for the discovery of novel MAO inhibitors?" In an Integrated View of the Molecular Recognition and Toxinology—From Analytical Procedures to Biomedical Applications, Radis-Baptista, G., (Ed.), 2013.
Flamand, V et al., "Targeting monoamine oxidase A in advanced prostate cancer," J. Cancer Res. Clin. Oncol., 136(11):1761-1771, Nov. 2010.
Fukuda, T, "Neurotoxicity of MPTP," Neuropathology, 21(4):323-332, Sep. 2001.
Geha, RM et al., "Substrate and inhibitor specificities for human monoamine oxidase A and B are influenced by a single amino acid," J. Biol. Chem., 276(13):9877-9882, Mar. 2001.
Gimenez, BG et al., "Evaluation of blockbuster drugs under the rule-of-five." Pharmazie, 65(2):148-152, 2010.
Hao, R et al., "Selegiline protects dopaminergic neurons in culture from toxic factor(s) present in the cerebrospinal fluid of patients with Parkinson's disease," Neurosci. Lett., 200(2):77-80, Sep. 1995.
Hare, MLC "Tyramine oxidase: A new enzyme system in liver," Biochem. J., 22(4):968-979, Jun. 1928.
Heikkila, RE et al., "Importance of monoamine oxidase A in the bioactivation of neurotoxic analogs of 1-methyl-4-phenyl-1,2,3,6-tetrahydropyridine," Proc. Natl. Acad. Sci. USA, 85:6172-6176, Aug. 1988.
Huet, O et al., "NADH-dependent dehydrogenase-activity estimation by flow cytometric analysis of 3-(4,5-dimethylthiazolyl-2-YI)-2,5-diphenyltetrazolium bromide (MTT) reduction," Cytometry, 13(5):532-539 (1992).
Iwami, K et al., "A novel method of intracranial injection via the postglenoid foramen for brain tumor mouse models," J. Neurosurgery, 116:630-635, Mar. 2012.
Jekabsone, A et al., "Fibrillar beta-amyloid peptide A$_\beta$1-40 activates microglial proliferation via stimulating TNF-$\alpha$ release and H2O2 derived from NADPH oxidase: a cell culture study," J. Neuroinflammation, 3:24, Sep. 2006.
Jian, Y, "Synthesis and mechanistic studies on the monoamine oxidase (MAO) catalyzed oxidation of 1,4-disubstituted-1,2,3,6-tetrahydropyridines," in Chemistry, Virginia Polytechnic Institute and State University, Blacksburg, VA, USA, p. 179, Aug. 1998.
Johansson, M. et al., "Distribution of estramustine in the BT4C rat glioma model," Cancer Chemother Pharmacol, 41: 317-325, 1998.
Korzeniewski, C and Callewaert, DM, "An enzyme-release assay for natural cytotoxicity," J. Immunol. Methods, 64(3):313-320, 1983.
Lajiness, MS et al., "Molecular properties that influence oral drug-like behavior," Curr. Opin. Drug Discov. Develop., 7(4):470-477, 2004.
Lena, A. et al., "Drugs targeting the mitochondrial pore act as citotoxic and cytostatic agents in temozolomide-resistant glioma cells," Journal of Translational Medicine, 7: 13, Feb. 2009.
Lipinski, CA et al., "Experimental and computational approaches to estimate solubility and permeability in drug discovery and development settings," Adv. Drug Delivery Rev., 46(1-3):3-26, 2001.
Malmström, BG et al., Copper-containing oxidases and superoxide dismutase. in: P.D. Boyer, (Ed.), The Enzymes, Academic Press, New York, pp. 507-579, 1975.
Mander, PK et al., "Microglia proliferation is regulated by hydrogen peroxide from NADPH oxidase," J. Immunol., 176(2):1046-1052, 2006.
Nimkar, SK et al., "Studies on the monoamine oxidase-B-catalyzed biotransformation of 4-azaaryl-1-methyl-1,2,3,6-tetrahydropyridine derivatives," J. Med. Chem., 42(10):1828-1835, Jan. 1999.
Ottoboni, S et al., "Deuterium isotope effect measurements on the interactions of the neurotoxin 1-methyl-4-phenyl-1,2,3,6-tetrahydropyridine with monoamine oxidase B," J. Biol. Chem., 264:13684-13688 (1989).
Palmer, SL, "The investigation of the active sites of monoamine oxidase (MAO) A and B and the study of MAO A mediated neurotoxicity using 4-substituted tetrahydropyridines," Ph.D. thesis, Department of Chemistry, Virginia Polytechnic Institute, Blacksburg, VA, USA, May 1998.
Palmer, SL et al., "Probing the active sites of monoamine oxidase A and B with 1,4-di-substituted tetrahydropyridine substrates and inactivators," J. Med. Chem., 40(13):1982-1989, Feb. 1997.
Price, CC et al., "Relative reactivities for monofunctional nitrogen mustard alkylation of nucleic acid components," Biochim. Biophys. Acta., 166(2):327-359 (1968).
Regina, GL et al., "New pyrrole inhibitors of monoamine oxidase: synthesis, biological evaluation, and structural determinants of MAO A and MAO B selectivity," J. Med. Chem., 50(5):922-931, 2007.
Sharpe, MA et al., "Thimerosal-derived ethylmercury is a mitochondrial toxin in human astrocytes: possible role of Fenton chemistry in the oxidation and breakage of mtDNA," J. Toxicol., 2012:1-12, 2012.
Sharpe, MA et al., "Design and Synthesis of a MAO-B-Selectively Activated Prodrug Based on MPTP: Mitochondria-Targeting Chemotherapeutic Agent for Treatment of Human Malignant Gliomas," ChemMedChem, 10, 621-628, 2015.
Shi, H et al., "1-Methyl-4-phenyl-2,3-dihydropyridinium is transformed by ubiquinone to the selective nigrostriatal toxin 1-methyl-4-phenylpyridinium," FEBS Lett., 461(3)196-200, 1999.

(56) References Cited

OTHER PUBLICATIONS

Stupp, R et al. "Radiotherapy plus Concomitant and Adjuvant Temozolomide for Glioblastoma," The New England Journal of Medicine 352;10, 987-996, Mar. 2005.
Toninello, A et al., "Amine oxidases in apoptosis and cancer," Biochim. Biophys. Acta, 1765:1-13, 2006.
True, L et al., "A molecular correlate to the Gleason grading system for prostate adenocarcinoma," Proc. Natl. Acad. Sci. USA, 103(29):10991-10996, May 2006.
Van De Waterbeemd, H et al., "Estimation of blood-brain barrier crossing of drugs using molecular size and shape and H-bonding descriptors," J. Drug Target., 6(2):151-165, 1998.
Veber, DF et al., "Molecular properties that influence the oral bioavailability of drug candidates," J. Med. Chem., 45(12):2615-2623, Jan. 2002.
Vizi, ES "Role of high-affinity receptors and membrane transporters in nonsynaptic communication and drug action in the central nervous system," Pharmacol. Rev., 52:63-90, 2000.
Wang, YX and Castagnoli, NJ, "Studies on the monoamine oxidase (MAO)-catalyzed oxidation of phenyl-substituted 1-methyl-4-phenoxy-1,2,3,6-tetrahydropyridine derivatives: factors contributing to MAO A and MAO B selectivity," J. Med. Chem., 38(11)1904-1910, Jan. 1995.
Yao, Y-S et al., "Total synthesis of 7-ethyl-10-hydroxycamptothecin (SN38) and its application to the development of C18-functionalized camptothecin derivatives," Chemistry, 17(37)10462-10469, 2011.
Youngster, SK et al., "Evaluation of the biological activity of several analogs of the dopaminergic neurotoxin 1-methyl-4-phenyl-1,2,3,6-tetrahydropyridine," J. Neurochem., 48(3):929-934, 1987.
Yoshida, D. et al., "Induction of apoptosis by estramustine phosphate mediated by phosphorylation of bcl-2," Journal of Neuro-Oncology 54: 23-29, 2001.

MAO-A and MAO-B sequences;
Channel blocking amino acids underlined and highlighted

```
         1234567890123456789012345678901234567890 (1-50)
         MSNKCDVVVVGGGISGMAAAKLLHDSGLNVVVLEARDRVGGRTYTLRNQK
         --23456789012345678901234567890123456789 (12-59)
         --HMFDVVVIGGGISGLSAAKLLTEYGVSVLVLEARDRVGGRTYTIRNEH
         1234567890123456789012345678901234567890 (51-100)
         VKYVDLGGSYVGPTQNRILRLAKELGLETYKVNEVERLIHHVKGKSYPFR
         01234567890123456789012345678901234567890 (60-109)
         VDYVDVGGAYVGPTQNRILRLSKELGIETYKVNSERLVQYVKGKTYPFR
         1234567890123456789012345678901234567890 (101-150)
         [shaded]MDDMGREIPSDAPWKAPLAEEWDNMTMKE (P102)
         0123456789012345678901234567890123456789 (110-159)
         G[shaded]IDNMGKEIPTDAPWEAQHADRWDKMTMKE
         1234567890123456789012345678901234567890 (151-200)
         LLDKLCWTESAKQ ATLFVNL VTAETHEVSALWFLWYVKQCGGTTRI  (L164/C172/I199/S200)
         0123456789012345678901234567890123456789 (160-209)
         L DKICWTKTAPR AYLFVNI VTSEPHEVSALWFLWYVKQCGGTTRI  (F173/N181/F208/S209)
         1234567890123456789012345678901234567890 (210-250)
         NG Q RKFVGGSGQVSERIMDLLGDRVKLERPVIYIDQTRENVLVETL (T201/Q206)
         0123456789012345678901234567890123456789 (210-259)
         NGG RKFVGGSGQVSERIMDLLGDQVKLNHPVTHVDQSSDNIIIETL (V210/T211/E216)
         1234567890123456789012345678901234567890 (251-300)
         NHEMYEAKYVISAIPPTLGMKIHFNPPLPMMRNQMITRVPLGSVIKCIVY
         0123456789012345678901234567890123456789 (260-309)
         NHEHYECKYVINAIPPTLTAKIHFRPELPAERNQLIQRLPMGAVIKCMMY
         1234567890123456789012345678901234567890 (301-350)
         YKEPFWRKKDYCG MIIDGEEAPVA TLDDTKPEGNYAAIMGFILAHKAR (T314/Y326)
         0123456789012345678901234567890123456789 (310-359)
         YKEAFWKKKDYCG MIEDEDAPIS TLDDTKPDGSLPAIMGFILARKAD (C323/I335)
         1234567890123456789012345678901234567890 (351-400)
         KLARLTKEERLKKLCELYAKVLGSLEALEPVHYEEKNWCEEQYSGGCYTT
         0123456789012345678901234567890123456789 (360-409)
         RLAKLHKEIRKKKICELYAKVLGSQEALHPVHYEEKNWCEEQYSGGCYTA
         1234567890123456789012345678901234567890 (401-450)
         YFPPGILTQYGRVLRQPVDRIYFAGTETATHWSGYMEGAVEAGERAAREI
         0123456789012345678901234567890123456789 (410-459)
         YFPPGIMTQYGRVIRQPVGRIFFAGTETATKWSGYMEGAVEAGERAAREV
         1234567890123456789012345678901234567890 (451-500)
         LHAMGKIPEDEIWQSEPESVDVPAQPITTTFLERHLPSVPGLLRLIGLTT
         0123456789012345678901234567890123456789 (460-509)
         LNGLGKVTEKDIWQEPESKDVPAVEITHTFWERNLPSVSGLLKIIGFST
         12345678901234567890                    (501-520)
         IFSATALGFLAHKRGLLVRV        (SEQ ID NO:1)
         012345678901234              (510-524)
         SVTALGFVLYKYKLL             (SEQ ID NO:2)
```

*FIG. 3*

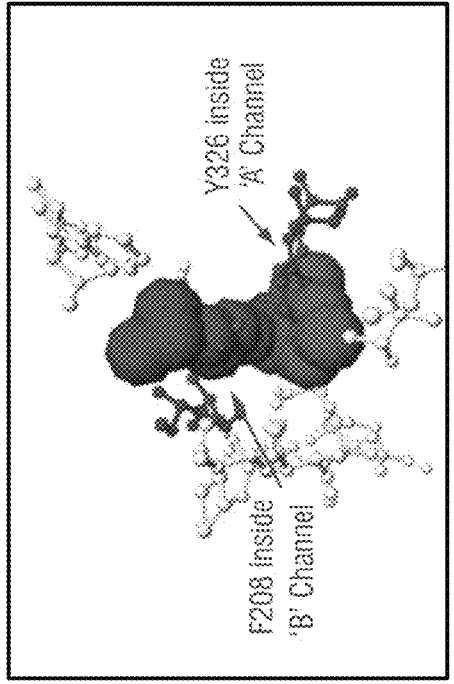
FIG. 4A THE 'A' AND 'B' CHANNELS IN MAO
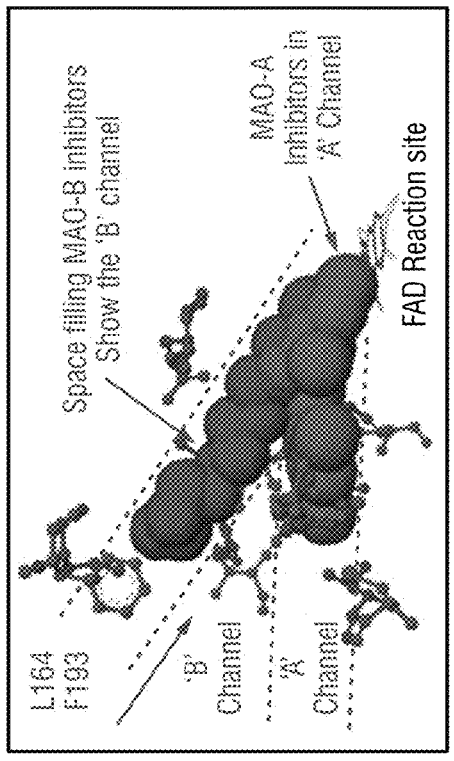
FIG. 4B 'A' BLOCKED BY Y326 AND 'B' BLOCKED BY F208
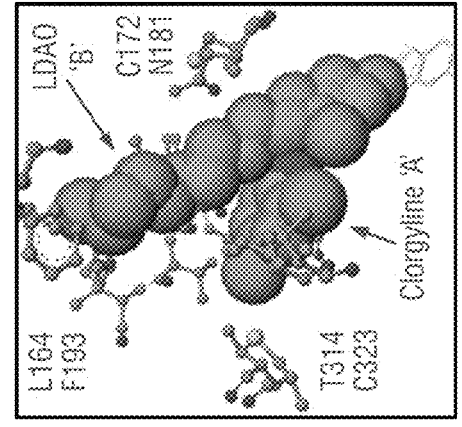
FIG. 4C INHIBITORS IN CHANNELS
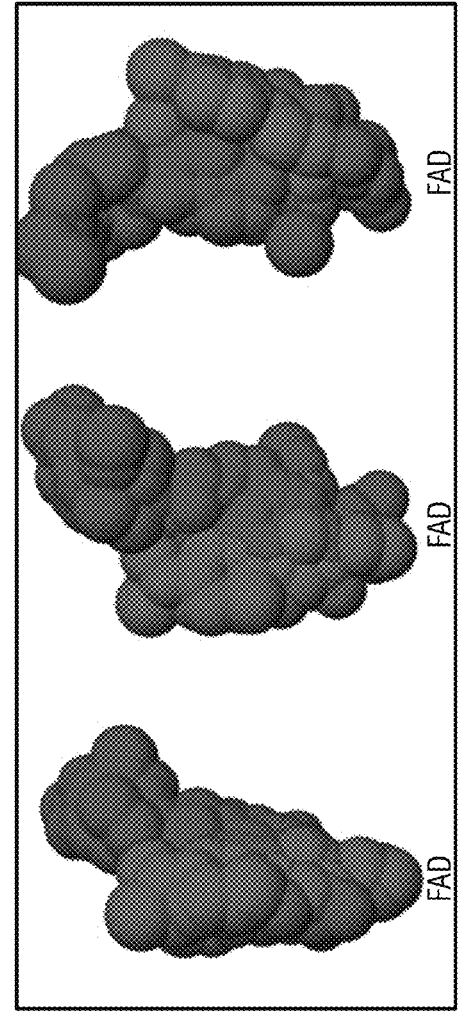
FIG. 4D D. SPACEFILLING OVERLAY OF SPECIFIC 'A' AND 'B' INHIBITORS

Monoamine Oxidase Inhibitory Activities of Pyrroles; $K_i$ μM

| Assig # | 20 | 19 | 7 | 21 | 22 | 23 |
|---|---|---|---|---|---|---|
| STRUCTURE | | | | | | |
| MAO-A | 0.02 | 0.15 | 3.5 | 0.05 | 0.05 | 0.1 |
| MAO-B | 0.7 | 85 | 0.02 | 4.8 | 2 | 2.5 |
| B/A | 35 | 566.6 | 0.0057 | 96 | 40 | 25 |
| A/B | 0.03 | 0.00 | 175.5 | 0.01 | 0.03 | 0.04 |

Data from P. egina, et al., J. Med. Chem. 2007

FIG. 5

THE HUMAN MAO-B CHANNEL AND REACTION POCKET
PROBED USING PROTEIN CRYSTAL STRUCTURES OF
SPECIFIC MAO-B INHIBITORS AND MODELED WITH PRO-DRUGS
| ALL INHIBITORS | MPMUS & PAMSN38 | MP-MUS | PAM-SN38 |
|---|---|---|---|
| 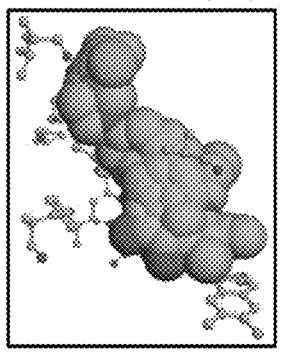 | 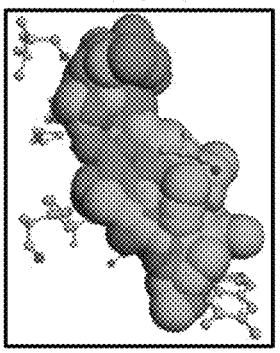 | 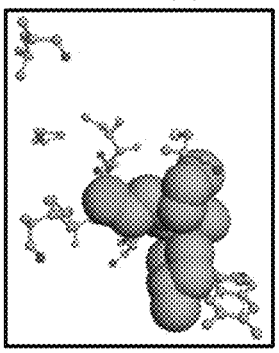 | 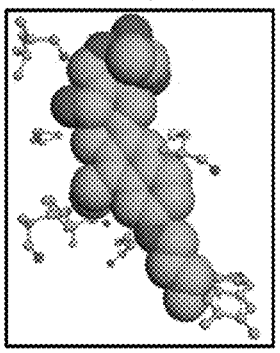 |
| FIG. 9A | FIG. 9B | FIG. 9C | FIG. 9D |
| 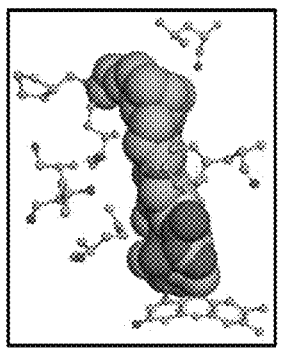 | 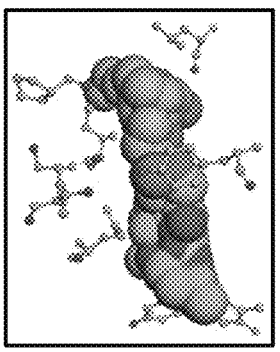 | 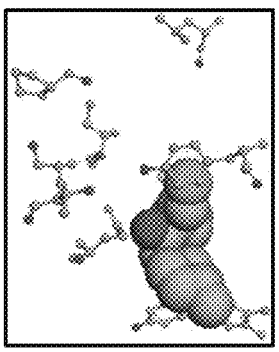 | 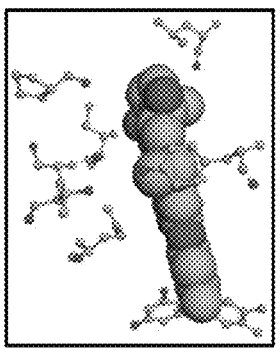 |
| FIG. 9E | FIG. 9F | FIG. 9G | FIG. 9H |
| 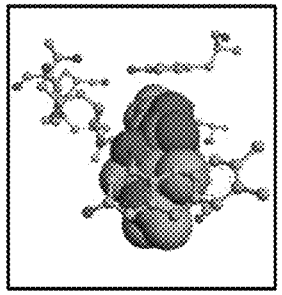 | 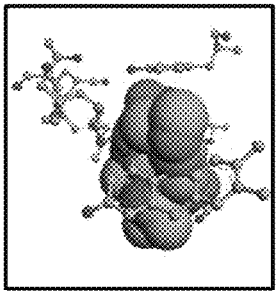 | 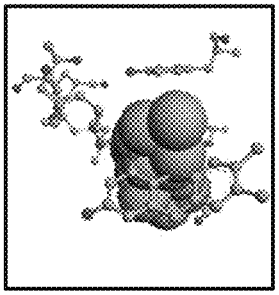 | 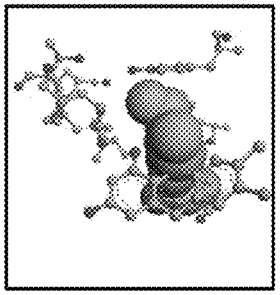 |
| FIG. 9I | FIG. 9J | FIG. 9K | FIG. 9L |
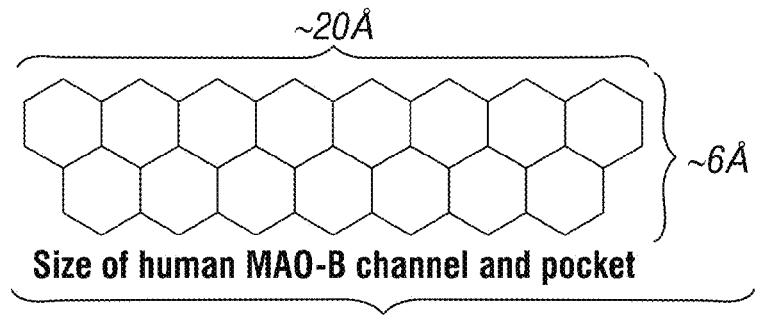
Size of human MAO-B channel and pocket
FIG. 9M 3-(R2)-oxypropyl-(R1)-amine 3-(R2)-oxy-N-(R1)cyclohexan-1-amine (3-methoxypropyl)(methyl)amine 4-(R2)-oxy-1-(R1)-3,6-dihydro-2H-pyridine 2,2-difluoro-3-(R2)-oxy-1-(R1)-5H-pyrrole 2,2-dimethyl-3-(R2)-oxy-1-(R1)-5H-pyrrole 2-R3-N-R2-N-R1-2-(1-X-1,2,3,6-tetrahydropyridin-4-yl) acetamide 4-phenyl-1-X-1,2,3,6-tetrahydropyridine 4-cyclohexyl-1-X-1,2,3,6-tetrahydropyridine 4-(5-R1-4-R2-3-R3-furan-2-yl)-1-X-1,2,3,6-tetrahydropyridine

NITROGEN MUSTARD:

bis(2-chloroethyl)[Linker-TP]amine

SULPHUR MUSTARD:

1-[(2-R1-2-R2-2-[Linker-TP]ethyl)sulfanyl]-3-chloropropane

SULPHUR MUSTARD:

({[(3-chloropropyl)sulfanyl]
methyl})[Linker-TP]-R1-
amine

SULPHAN:

3-[Linker-TP]-4-
(methanesulfonylmethoxy)butyl
methanesulfonate

PLATIN TETRANITRATE:

1,10-dichloro-5-[Linker-TP]-2,9-
diaza-1,10-diplatinadecane-
1,1,10,10-tetramine

***cis*-PLATIN DERIVED:**

2,2-diamino-5-[Linker-TP]-1,3-dioxa-
2-platinacyclohexane-4,6-dione

| Structure | Name |
|---|---|
| Cl~~~NH-C≡CH | (3-chloropropyl)(ethynyl)amine; N-(3- |
| Cl~~~NH-cyclobutyl | chloropropyl)cyclobutanamine; N-(3- |
| Cl~~~NH-cyclopropyl | chloropropyl)cyclopropanamine; [(3- |
| Cl~~~NH-CH2OH | chloropropyl)amino]methanol; |
| Cl~~~NH-C(CH3)3 | tert-butyl(3-chloropropyl)amine |
| Cl~~~NH-C(R1)(R2)(R3) | [R1, R2, R3, methyl](3-chloropropyl)amine; |
| Substituents R1, R2 and R3 include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as, $-NR_aR_b$, $-NR_aC(=O)R_b$, $-NR_aC(=O)NR_aNR_b$, $-NR_aC(=O)OR_b$, $-NR_aSO_2R_b$, $-C(=O)R_a$, $-C(=O)OR_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$. |||

*FIG. 27*

Vinblastine (vinca alkaloid)

Docetaxel (taxel)

SN-38 (Topoisomerase I)

Etoposide (Topoisomerase II)

| MPTP phenyl ring derivatives indicate size and shape define specificity | | | | | | | | | |
|---|---|---|---|---|---|---|---|---|---|
| R1 | -CF₃ | isopropyl | propyl | ethyl | -OMe | methyl | -Cl | -H | -F |
| B/A | 0.0006 | 0.05 | 0.13 | 0.4 | 0.46 | 2.15 | 3.38 | 3.66 | 10.54 |

FIG. 30

MAO-A substrates have rings rotated by 90° and are 'fatter' than MAO-B substrates

In Vivo Studies:
Q1: MP-MUS rapidly shrinks GBM tumors
Single 8μg/g MP-MUS tail-vein injection at 24 hours

| Animal at end of study period† | Brain Fixation | Dehydration | Sample Slicing |
|---|---|---|---|
| 4 Saline treated (Sal #7 to #11) | Remove Brains<br>↓<br>48 hr 2% Ice-Cold Paraformaldehyde | Graded ethanol dehydration<br>Xylene<br>Embed in wax<br>5μm slices on slides | Sagittal 5μm slices<br>Wax block |
| Caged matched MP-MUS treated | Antigen Retrieval<br>↓<br>20 min Steam Bath NaCitrate, pH6.0 | Rehydration<br>↓<br>Xylene<br>Graded Ethanol | |
| Binding Block<br>↓<br>IgG-Blocking<br>1 hr Vector 1:100 Horse HRP-IgG Anti-Mouse (H&L) | Lable Epitope<br>↓<br>Primary IgG<br>1:100 1 hour | Permeabilization<br>↓<br>Wash PBS 0.1% Tween X-100 | HRP-linkage*<br>↓<br>1 hr Vect or 1:100 Horse HRP-IgG Anti-Mouse (H&L) or HiDef HRP System |
| Wash<br>↓<br>PBS 0.1% Tween X-100 | Wash<br>↓<br>PBS 0.1% Tween X-100 | Wash<br>↓<br>PBS 0.1% Tween X-100 | Wash<br>↓<br>PBS 0.1% Tween X-100 |
| Peroxidase Block*<br>↓<br>1.8% $H_2O_2$ 5 min<br>1% Periodate 5 min<br>0.02% $NaBH_4$ 2 min | | DAB Lable<br>↓<br>DAKO<br>DAB Labeling Kit 10-30 minutes | |
| Nuclear DNA Labeling<br>↓<br>Hematoxylin<br>$Li_2CO_3$ Development<br>PBS 0.1% Tween | 1 μm DAPI 5 min<br>PBS 0.1% Tween | | |

FIG. 39

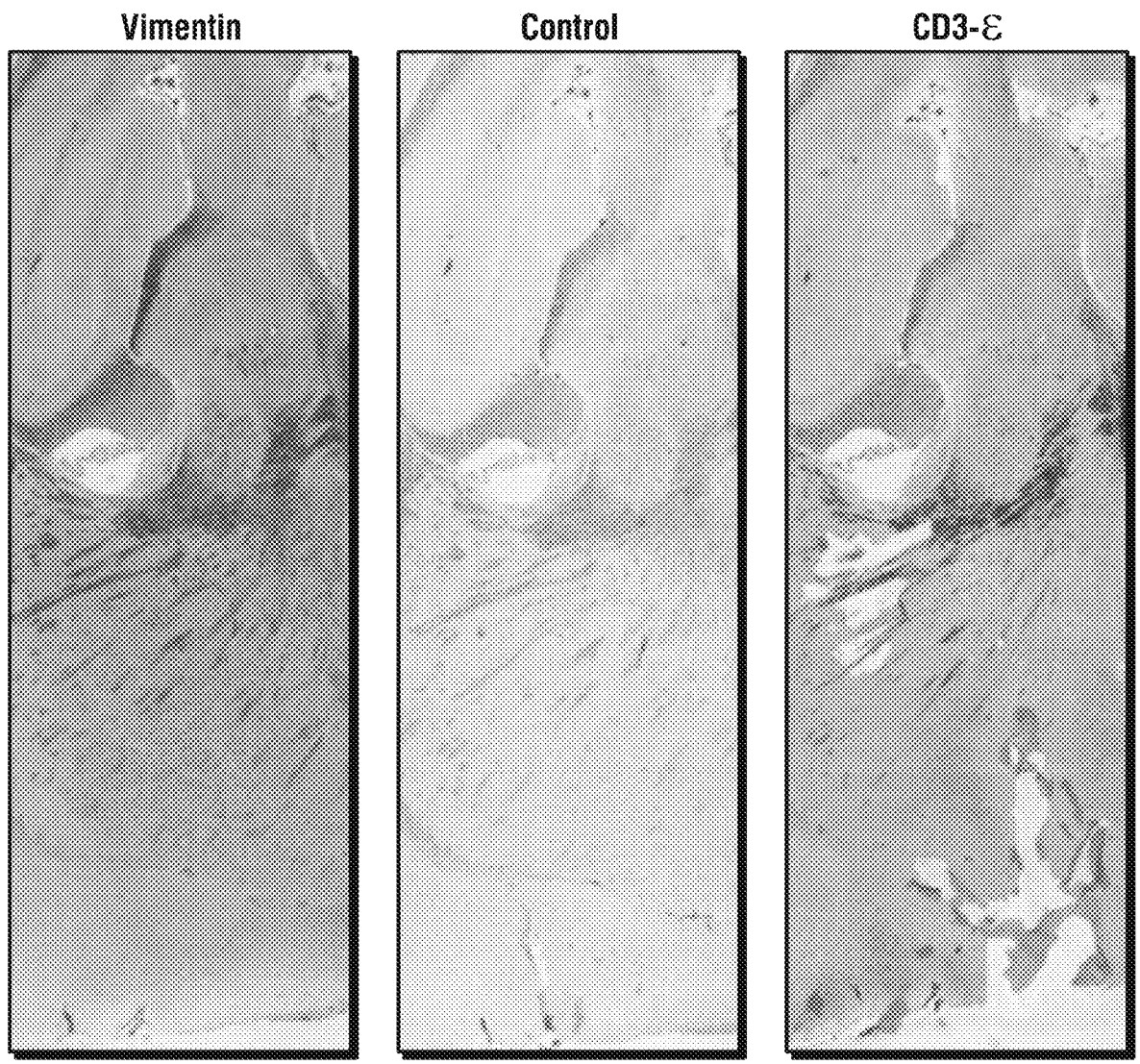
LABELING OF ADJACENT TISSUE SAMPLES, ON THE SAME SLIDE, WITH ANTI-VIMENTIN, NO PRIMARY ANTIBODY AND ANTI-CD3ε; ALL DEVELOPED WITH HORSE HRP/DAB
*FIG. 40A*  *FIG. 40B*  *FIG. 40C*

INFILTRATION OF HUMAN PRIMARY GLIOMA FROM RIGHT HAND SIDE INJECTION SITE TO LEFT HEMISPHERE. GLIOMA LABELED USING ANTI-VIMENTIN (V9) AND VISUALIZED USING DAB.

HUMAN VIMENTIN↑

VIMENTIN AND DAPI↑

DAPI↑

HUMAN VIMENTIN↑

VIMENTIN AND DAPI↑

DAPI↑

CD3-ε(NK/T-CELLS)↑ 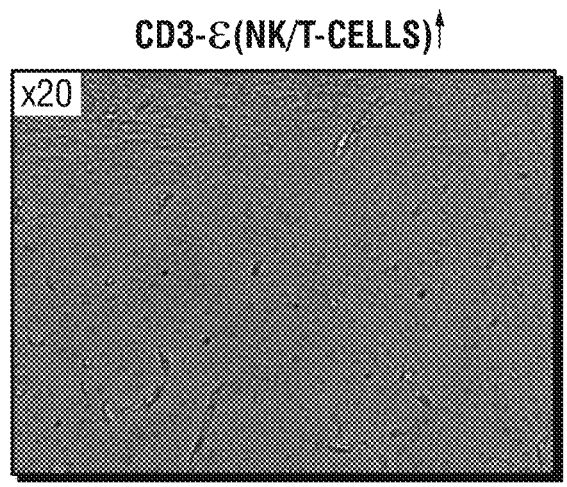 CD3-ε AND DAPI↑ 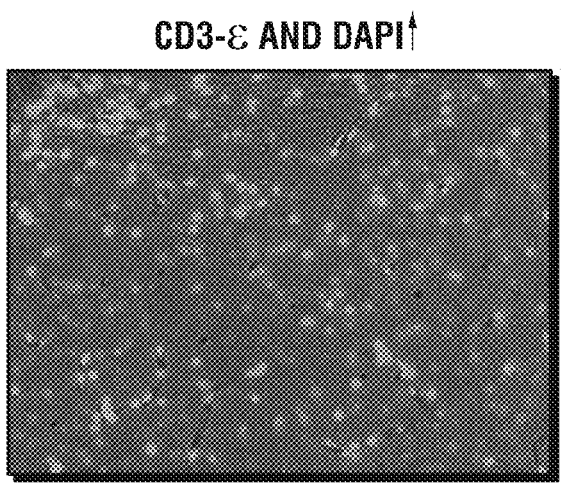
FIG. 42G　　　　　　　　　FIG. 42H
DAPI↑ 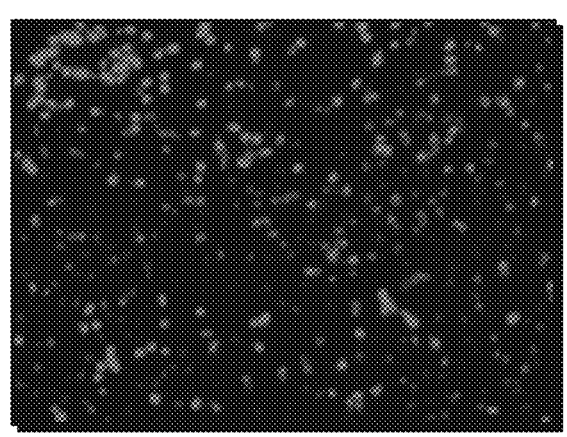 CD3-ε(NK/T-CELLS)↑ 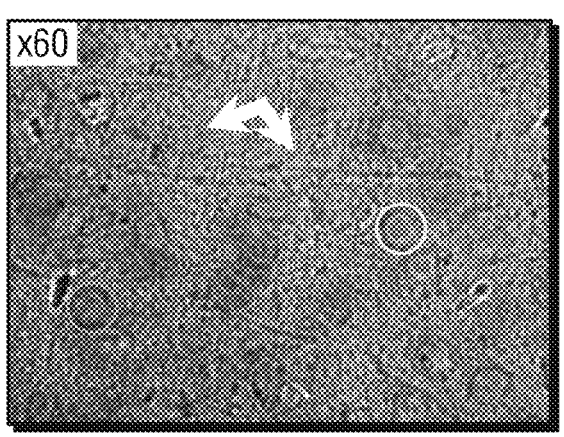
FIG. 42I　　　　　　　　　FIG. 42J
CD3-ε AND DAPI↑ 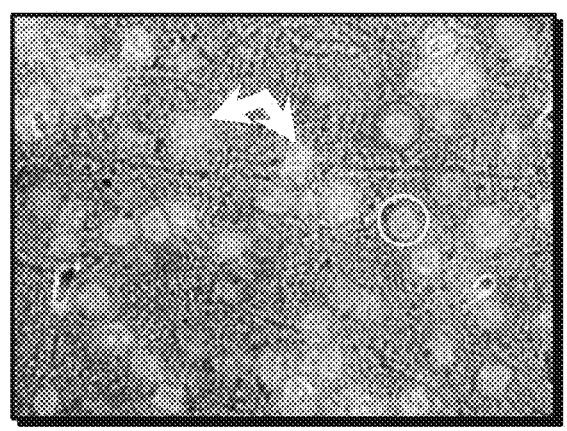 DAPI↑ 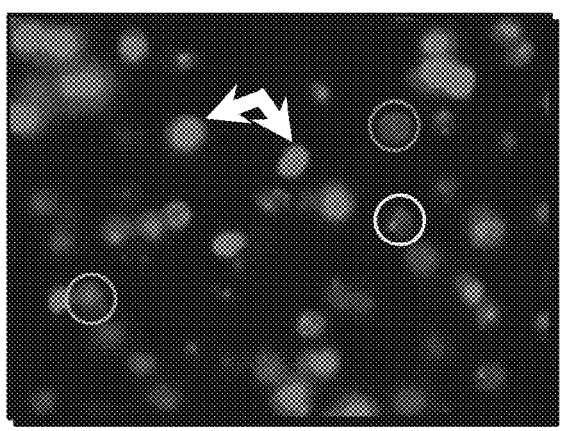
FIG. 42K　　　　　　　　　FIG. 42L

VEMENTIN

CD3ε

EGFR

VEMENTIN

CD3ε

EGFR

NO PRIMARY (SLIDE 14)
VIMENTIN LABELED
(SLIDE 17; 30μm DISTANT)
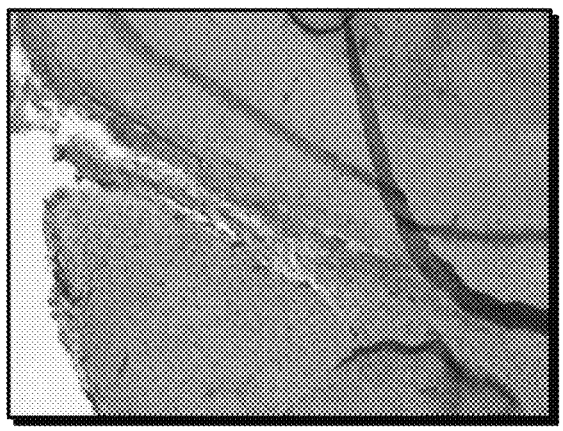 
FIG. 44A
FIG. 44B
NO PRIMARY (SLIDE 14)
VIMENTIN LABELED
(SLIDE 17; 30μm DISTANT)
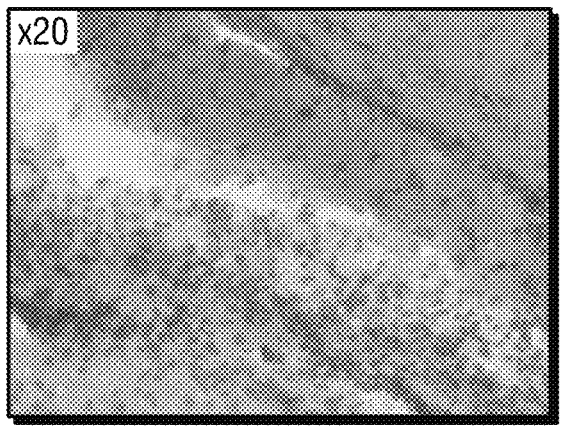 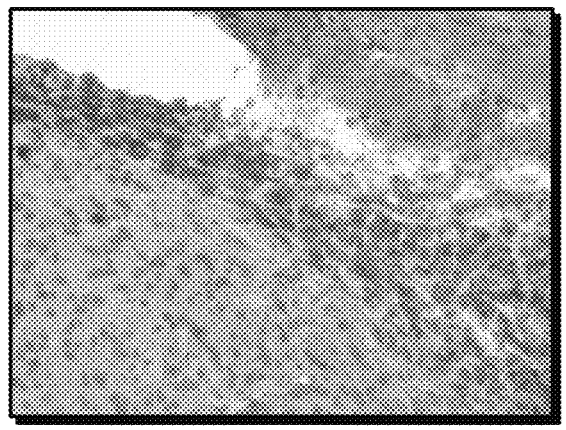
FIG. 44C
FIG. 44D

VIMENTIN

NO PRIMARY

CD3-ε

VIMENTIN

NO PRIMARY

CD3-ε

VIMENTIN

NO PRIMARY

CD3-ε

VIMENTIN

NO PRIMARY

CD3-ε

CHEMOTHERAPEUTIC COMPOSITIONS AND METHODS FOR TREATING HUMAN GLIOMAS

CROSS-REFERENCE TO RELATED APPLICATIONS

The present application is a continuing application based upon PCT Intl. Pat. Appl. No. PCT/US2012/062850; filed Oct. 31, 2012, which claims priority to U.S. Provisional Pat. Appl. No. 61/553,854; filed Oct. 31, 2011, the contents of each of which is specifically incorporated herein in its entirety by express reference thereto.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

BACKGROUND OF THE INVENTION

Field of the Invention

The present invention generally relates to pharmaceutical compositions and oncological treatment methods. In particular, the invention provides improved compositions for targeting chemotherapeutics to mitochondria, and methods for selective therapy of mammalian cancers, and in particular, human cancers such as gliomas.

Description of Related Art

Gliomas: Prognosis and Treatment. Nearly 10,000 Americans each year are diagnosed with malignant glioma. Of those, 50% survive one year, and only 20% survive two years. Five-year survival rate is <3%. Conventional treatment consists of a triad: surgery (if the location allows it), radiotherapy, and chemotherapy. After surgery, chemotherapy (normally in the form of DNA acylating agents such as temozolomide or carmustine or more rarely, the topoisomerase inhibitor, irinotecan) is initiated. In certain patients, carmustine may also be delivered in the form of wafers placed into the post-surgical wound.

Gliomas are the most common malignant brain tumors reported in humans. Gliomas are neuronal malignancies that arise from an uncontrolled proliferating cell of the central nervous system. Patients diagnosed with gliomal cancer have a dismal prognosis, and although symptoms vary with the particular site of the tumor, they tend to develop very quickly due to the rapid growth behavior of the tumor cell. Gliomas can originate from several cell types including ependymal cells, astrocytes, oligodendrocytes and different types of glia cells. Clinically, gliomas are divided into four grades, which are determined by pathologic evaluation of the tumor. Low-grade gliomas are well-differentiated and slower growing, thus biologically less aggressive, and therefore offer a relatively better prognosis for the patient. Conversely, high-grade gliomas are anaplastic, fast-growing, and invasive towards adjacent tissues. Consequently, high-grade gliomas offer a worse prognosis for the patient. Unfortunately, the most aggressive of these grades, grade 4 or glioblastoma multiforme (GBM), is also the most frequent in humans. Because most patients with GBMs die of their disease in less than a year (and essentially no GBM patient has what would be considered a "long-term survival"), the development of more effective treatment regimens for the disease has been vigorously pursued for more than fifty years, with, unfortunately, only limited success to date.

Cancers, Mitochondria and Hydrogen Peroxide as a Mitogen. Hydrogen peroxide is a product of mitochondrial respiration, which produces superoxide by the one-electron reduction of molecular oxygen with hydrogen; peroxide is then generated by the action of superoxide dismutase or due to spontaneous dismutation (Vizi, 2000; Boveris and Chance, 1973). Hydrogen peroxide is a potent mitogen, particularly in microglia (Jekabsone et al., 2006; Mander et al., 2006). Cancer cells produce high amounts of hydrogen peroxide, which is linked to key alterations in cancer, including cell proliferation, apoptosis resistance, metastasis, angiogenesis and hypoxia-inducible factor 1 activation (Droge, 2002). In the absence of mitochondrially generated hydrogen peroxide, many cancers upregulate other enzymes, which produce hydrogen peroxide as a byproduct of their function. One such enzyme is monoamine oxidase.

Monoamine Oxidase A (MAO-A) and Monoamine Oxidase B (MAO-B)-Substrate and Inhibitor Specificity. Monoamine oxidases are the major enzymes used by the body to metabolize monoamine hormones and neurotransmitters such as epinephrine, norepinephrine, serotonin, and dopamine. There are two MAO subtypes, MAO-A and MAO-B, which are encoded by two separate genes but have a high degree of homology, and are both localized to the outer mitochondrial membrane. The two enzymes have different substrate/inhibitor specificity and tissue localization in different mammals.

Endogenous Substrates. MAO-A oxidatively deaminates epinephrine, norepinephrine, and serotonin and is found in the brain in adrenergic and noradrenergic neurons.

MAO-B acts preferentially on phenylethylamine and telemethylhistamine as substrates and is present in astrocytes and in serotoninergic and histaminergic neurons.

Inhibitors. In addition to different substrate specificities, the two MAO's also have different specificities toward inhibitors. MAO-A is classically inhibited by clorgiline, and MAO-B is classically inhibited by L-deprenyl (most often called selegiline).

The major structural difference between human MAO-A and B is that MAO-A has a single ovoid substrate cavity of ~550 $Å^3$ in volume and MAO-B contains an hour-glass-shaped cavity with an upper volume of ~290 $Å^3$, and a lower substrate cavity of ~400 $Å^3$ (Milczek et al., 2011).

The differential sensitivity toward inhibitors is a function of the differences in the structure of the two enzymes. The amino acid sequences of human MAO-A (red) and MAO-B (blue) are shown in FIG. 1.

The presence of a proline residue in position 102 of the B structure, with respect to the corresponding alanine in position 111 of the A structure, causes a change in the loop formed by the following 19 amino acids. The difference between the position and nature of the two loops cause the entrance to the reactive pocket in MAO-B to be smaller, and more hydrophobic than is the case in MAO-A. One consequence is that larger, bulkier, groups are able to enter the pocket of MAO-A.

The difference in the substrate channels, leading to the FAD active site pocket, of the two enzymes is shown in FIG. 2. This figure draws upon a number of crystal structures of human MAO-A and MAO-B, where the enzymes were pretreated with specific inhibitors. Overlaying structures indicates which amino acid variants between the two enzymes are responsible for the different substrate and inhibitor specificities. Geha et al. (2001) demonstrated that the substrate/inhibitor specificities of the two forms of the human MAO could be inverted by double substitutions of hMAO-A-I335Y and hMAO-B-Y326I indicate that the large, aromatic, residues midway along the MAO channels largely control substrate specificity.

Monoamine Oxidase B in Glioma. MAO-B catalyzes deamination of dopamine through a two-electron reduction of oxygen to hydrogen peroxide. In the brains of primates and mice, it is found only in the glia and dopaminergic neurons. The activity of MAO-B is four-fold greater in glioblastoma multiforme, low-grade astrocytomas, and in anaplastic astrocytomas than in postmortem control brains or meningiomas (Gabilondo et al., 2008). It appears that hydrogen peroxide is generated by gliomal MAO-B is part of a proliferation signal. Interestingly, in high-grade prostate cancer, there is a four-fold increase in MAO-A, and again the mitotic hydrogen peroxide signaling resulting from up-regulation may be the trigger for this increase in lethality (Flamand et al., 2010).

hMAO-Specific Inhibitors. It has been previously shown that it is possible to design and synthesize small molecular families that display highly differential inhibition constants to MAO-A and MAO-B; as an example, the inventors have drawn from Regina and co-workers in their examination of pyrroles as inhibitors of hMAO. In Table 1, six structures are shown which differ by the addition of a single $CH_2$ group.

FIG. 5 shows the inhibition constant ($K_i$ in μM) of MAO-A and MAO-B, and the inhibition ratio, for a series of related pyrrols. Structure #7 is a highly potent MAO-B inhibitor, but has very poor inhibition of MAO-A. Increasing the length of the chain between the phenyl ring and the tertiary amine, by a single —$CH_2$— unit, flips the sensitivity, and Structure #21, for example, is a potent MAO-A inhibitor, but is a very poor MAO-B inhibitor.

Three-dimensional modeling demonstrates that within the MAO channel, the phenyl rings of Structure #7 and Structure #21 tend to interact with the blocking amino acids described earlier. This is graphical illustrated in FIG. 3, which shows an overlay of Structure #7 and Structure #21, where the pyrrol is hydrogen bonded to the FAD ring. In MAO-B, Structure #7 does not overlay any of the amino acids lining the channel, but in MAO-A, the phenyl group of Structure #7 abuts F208.

Conversely, in MAO-A, Structure #21 does not overlay any of the amino acids lining the channel, but in MAO-B the phenyl group of Structure #21 abuts Y323.

A similar study performed on human recombinant MAO, looking at competitive inhibition using variations of a core phenylamine structure, was performed by Fierro and co-workers. The inhibitor structures and $K_i$ constants they found is presented in Table 2.

1-Methyl-1,2,3,6-Tetrahydropyridines. The best-known exogenous substrate of MAO-B is (1-methyl-4-phenyl-1,2,3,6-tetrahydropyridine) (MPTP), which is converted to its cationic form, 1-methyl-4-phenylpyridinium ($MPP^{30}$), by glial cells. $MPP^{30}$ is a dopamine mimetic, and is concentrated inside dopaminergic neurons via the dopamine transporter. Inside these neurons, $MPP^+$ undergoes a second concentrating effect; moving into their mitochondria in response to the membrane potential, $\Delta\Psi$, causing both inhibition and superoxide generation at Complex I, which can result in loss of mitochondrial function, caspase activation, dopaminergic cell apoptosis, and phenotypically, Parkinson's disease (Fukuda, 2001).

The mechanism of the conversion of MPTP to $MPP^{30}$ has been elucidated in two key papers: Ottoboni et al. (1989), which examined the kinetic effects of deuteration of different positions on MPTP to understand which hydrogen atoms are abstracted by the FAD reaction center; and Shi et al. (1999), who resolved the second oxidant step in the reaction.

FIG. 5 shows how MPTP is initially oxidized by MAO, with a hydrogen atom (from the C6 position on the tetrahydropyridine) and an electron from the amine to form 1-methyl-4-phenyl-2,3-dihydropyridin-1-ium ($MPDP^+$). The $MPDP^+$ diffuses from the enzyme and is then typically oxidized further by the mitochondrial ubiquinone pool to $MPP^+$, although direct oxidation by aqueous molecular oxygen occurs in vitro.

Much work has been done on probing the two MAO channels using substitutions on the MPTP template [see Palmer et al. (1997) and Palmer (1998)]. She examined the kinetics of human MAO-A and bovine MAO-B (which is very similar to human) enzymes with substitutions in the phenyl ring of MPTP. FIG. 6 shows the effects of nine different substituents in the 2'-position of the phenyl ring of MPTP, and how it effects the kinetics of the two enzymes. Modeling the shape of the nine molecules shows that there is a trend in the space-filling shape of the substrate and how well it acts as a substrate. In MPTP derivatives where the rings sit in a crossed position, 90° to one another, then the molecule serves as a better MAO-A substrate, whereas flat, planar MPTP molecules are far better MAO-B substrates.

It is evident that tetrahydropyridines can be designed so that they serve as very good MAO-B substrates, but very poor MAO-A substrates. It follows that following oxidation of the tetrahydropyridine to the pyridinium cation, the now-charged molecule will partition from near the outer mitochondrial membrane, into the inside of the mitochondria, with accumulation driven by the mitochondrial membrane potential.

Amino-Propyl Ethers. In addition to their oxidation of secondary and tertiary amines, outline above, monoamine oxidases can also cleave ether or thiol ether bonds; bonds which unlike amides or ester, are generally very stable in human beings. Albers, Rawlsa and Chang demonstrated the ability of MAO-A and MAO-B to oxidize the primary or secondary amine of a propylamine ester to form an alcohol (FIG. 7).

This reaction series, amine oxidation to imine, hydration and then rearrangement converting an ether to an alcohol is biologically unusual, given that ethers are typically biologically stable. Moreover, in addition to the conversion of an ether to an alcohol, the reaction could function to cleave a thioether to a thiol or secondary/tertiary amines into primary/secondary amines.

Deficiencies in the Prior Art

One of the reasons for the resistance of GBM to therapeutic treatments is the complex character of the tumor itself. As the name GBM implies, glioblastoma is multiforme. It is multiforme both grossly (often presenting regions of necrosis and hemorrhage) and microscopically (complete with regions of pseudopalisading necrosis, pleomorphic nuclei and cells, and microvascular proliferation). Moreover, GBM is genetically diverse, with various deletions, amplifications, and point mutations leading to activation of signal transduction pathways downstream of tyrosine kinase receptors such as epidermal growth factor receptor (EGFR) and platelet-derived growth factor receptor (PDGFR), as well as to disruption of cell-cycle arrest pathways by INK4a-ARF loss or by p53 mutations associated with cyclin-dependent kinase 4 (CDK4) amplification or retinoblastoma-protein (Rb) loss.

Compounding the difficulty in successful GBM treatment is the fact that surgical resection of the tumor is hampered by the topographically-diffuse nature of the tumors themselves. Moreover, the location of the GBM tumor cells within the brain can also be highly variable, resulting in the inability to completely resect this tumor. Glioma cells migrate away from the initial tumor through the brain parenchyma, collect just below the pial margin (subpial spread), surround neurons and vessels (e.g., perineuronal and perivascular satellitosis), and migrate through the white matter tracks (e.g., intrafascicular spread). As a result, the individual tumor cells diffuse over long distances, and into areas of the brain that are essential for the patient's survival. An extreme example of this behavior is a condition referred to as "gliomatosis cerebri," in which the entire brain is diffusely infiltrated by neoplastic cells with minimal or no central focal area of tumor per se. Although gliomas do not metastasize via the bloodstream, they can spread via cerebrospinal fluid and cause what is referred to as "drop metastases" in the spinal cord. Fully one quarter of patients with GBM demonstrate multiple or multi centric GBMs at autopsy. Consequently, the infiltrative growth pattern of these tumors precludes curative neurosurgery, and high-grade gliomas almost always recur even after what was thought to be "complete" surgical resection.

Despite recent advances in therapy, treatment of malignant gliomas remains palliative. Median post-diagnosis survival for anaplastic astrocytoma is less than 3 years and for glioblastoma multiforme is typically only 12 to 14 months. Temozolomide, an oral methylating chemotherapeutic agent, became standard of care for newly diagnosed glioblastoma when used concurrently with external beam radiation followed by adjuvant therapy, although GBM continue to be highly resistant to radiation. Under even the best of circumstances (in which essentially all of the tumor can be surgically removed and the patients are fully treated with radiation and chemotherapy), the mean survival of this disease is extended only by a period of a few months.

The poor outcome of the standard treatments for GBM coupled with the diffuse nature of the disease itself, have influenced a number of attempts at novel therapeutic approaches with the aim of also killing neoplastic cells disseminated from the main tumor. To date, however, the only significant therapeutic options for GBM are limited to surgery, radiotherapy and conventional chemotherapy using drugs such as carmustine, lomustine, vincristine, procarbazine, carboplatin, cis-platin, etoposide, irinotecan, and its active metabolites, and related agents.

Concurrent administration of temozolomide (TMZ) and radiotherapy (RT) has emerged as the primary 'standard of care' for patients with newly diagnosed GBM. A clinically-meaningful improvement in survival compared to RT alone has been demonstrated, but the increase is still disappointing (median survival time for patients treated with TMZ/RT is 15 months, vs. only 12 months for patients treated with RT alone).

In spite of the successful introduction of TMZ-based combination therapy, however, clinicians still concur that there remains a significant need for the development of new chemotherapeutically-active agents for use in the treatment of glioma, and particularly for GBM and advanced stages of the disease. Similarly, there remains a significant, unmet need in the medical arts for new chemotherapeutic agents effective in the prevention, treatment, and/or amelioration of one or more symptoms of hyperproliferative disorders, and particularly for aggressive forms of mammalian cancers, such as human gliomal tumors.

Primary brain tumors are classified into more than 10 types according to their origin of onset and pathological tissue type, examples of which include glioma and meningioma. Gliomas are particularly serious in terms of both incidence and malignancy, and are classified into seven or more types such as glioblastoma and anaplastic astrocytoma according to their detailed pathological tissue type. Disease stage (i.e., tumor size, presence of distal metastasis) and histological malignancy are used to determine the degree of malignancy of primary brain tumors, with histological malignancy being classified into four levels of advancing degree of malignancy (G1 to G4). For example, the malignancy of glioblastoma is G4 (WHO4), while the malignancy of anaplastic astrocytoma is G3 (WHO3), and both G3 and G4 are classified as malignant. Thus, those primary brain tumors that should first be targeted by anti-brain tumor agents are gliomas, and particularly glioblastoma or anaplastic astrocytoma associated with a high degree of malignancy.

Although definitive efficacy of chemotherapy has only been confirmed for alkylating agents and temozolomide, their efficacy is limited to concomitant use with radiotherapy. Post-surgical radiotherapy has also been demonstrated to demonstrate life-prolonging (albeit brief) effects.

Therefore, an important object of the present invention is to provide novel compounds (and pharmaceutical that include them) for use in chemotherapeutic methods aimed at treating malignant cancer in affected animals, and in particular, in mammals such as humans, diagnosed with one or more forms of glioma.

BRIEF SUMMARY OF THE INVENTION

The present invention addresses these and other unmet deficiencies inherent in the relevant oncological and pharmaceutical arts, by providing novel, non-obvious, and useful tripartite compounds (as well as compositions comprising them) for preventing, treating, and/or ameliorating one or more symptoms of at least a first mammalian cancer.

In an overall and general sense, the compounds of the present invention preferably include at least a first targeting or "seeker" moiety that is operably linked (preferably via at least a first chemical linker molecule), to at least a first therapeutic moiety. Preferably, the first therapeutic moiety is a neutral, blood brain barrier permeable molecule, and in particular embodiments, is an inactive, or substantially inactive, pro-drug. Such therapeutic moieties are preferably DNA acylating or DNA damaging agents, and in certain embodiments, is a "nitrogen mustard," a "sulfur mustard," a platin tetranitrate, vinblastine, docetaxel, etoposide, camptothecin (or one of its active metabolites such as SN38, lomustine, or carmustine), or a derivative, an analog, a salt or any combination thereof.

In particular, the present invention overcomes various limitations inherent in the prior art by providing novel compositions and methods for treating human gliomas. In illustrative embodiments, the inventors have synthesized and tested pro-drug compounds, which are MAO-B-specific substrates that have been specifically designed to kill cancer cells such as human gliomas. After oxidation of the pro-drug, the cationic mature drug preferentially accumulates in the mitochondria of the targeted cancer cells, where it acylates mitochondrial DNA and ribosomal RNA, and thereby inactivates and/or kills the cancer cells by disrupting the normal function of the mitochondria.

Using an enzyme that is highly "up-regulated" in glioma, MAO-B, neutral, blood-brain-barrier permeable pro-drugs, including, for example MP-MUS and APE-SN38 (3-amino-propoxy-SN38 or Amino Propyl Ether-SN38), have been prepared and shown to be highly active against cancer cells via the MAO-B conversion into active species, P+-MUS, and SN38, respectively.

In the case of MP-MUS the conversion to the P+-MUS mature drug, a cationic species that accumulates inside mitochondria at a cytosolic/mitochondrial matrix ratio of approximately 1:1000. Thus, the linked chemotherapeutic, in this case a DNA acylating agent, a nitrogen mustard, is selectively delivered in concentrations effective to destroy the mitochondrial DNA. While MAO-B is found in normal glia, the enzyme is up-regulated at least five-fold in gliomas, making it an ideal candidate for selectively targeting chemotherapeutic agents to gliomal mitochondria, since mitochondria are required by gliomal cells for pyrimidine synthesis. In addition, because mitochondrial DNA damage does not increase the typical base-excision repair pathways that are typically associated with nuclear DNA damaging chemotherapeutic resistance, the delivery of the chemotherapeutic preferentially to the mitochondria offer significant advantages over conventional chemotherapeutic protocols.

In the case of APE-SN38, the parental compound is SN38, a camptothecin which is a potent topoisomerase-I inhibitor. This chemotherapeutic agent is normally given to patients as a pro-drug, irinotecan. In irinotecan, the topoisomerase-I activity of the camptothecin is arrested, until bioactivation, by esterification of the phenolic alcohol of SN38 with 4-(piperidin-1-yl)piperidine-1-carboxylic acid. In PAM-SN38, the pro-drug has no activity toward topoisomerase-I. The pro-drug undergoes MAO specific activation by oxidative cleavage of the amino-propyl-ether, unmasking the phenolic alcohol of the camptothecin.

The present invention provides new and useful compounds that may advantageously be used to selectively target one or more chemotherapeutic agents to mammalian mitochondria. The invention also provides novel compositions comprising these compounds, as well as methods of use for these compounds, including, for example, in the preparation of medicaments for the therapeutic treatment of one or more mammalian hyperproliferative disorders, including, for example, human gliomal cancers and the like.

To exploit the chemotherapeutic action of cytotoxic compounds useful in chemotherapy regimens, the inventors have developed unique targeting moieties whose activity is modulated by the activity of an enzyme that is up-regulated in many types of cancer cells, including GBM. These novel targeting moieties permit the delivery of a non-cytotoxic pro-drug to cells, which is then transformed into a cytotoxic, active chemotherapeutic agent via accumulation within the mitochondria of mammalian cells, where the compounds exert their cytotoxic effect(s), including for example, DNA acylation and damage. The targeted delivery of such cytotoxic active compounds, by designing them to be preferentially uptaken by cellular mitochondria across the mitochondrial membrane, improve the efficacy of the delivered chemotherapeutic, while at the same time, lowering the amount of cytotoxic agent to other compartments of the cell, including, for example, the nucleus.

Preferably, the compounds disclosed herein are multicomponent in nature, such that each compound preferably includes one or more "targeting" or "seeker" moieties operably linked (either directly or indirectly, by the incorporation of one or more chemical linkers) to one or more "cytotoxic" or "chemotherapeutic" moieties, wherein the initial pro-drug form of the compound is substantially "inactive" (i.e., non-cytotoxic), but whereupon is converted to an "active" (i.e., a cytotoxic or chemotherapeutic "warhead") form by the enzymatic catalysis of the pro-drug to the active drug by a mammalian enzyme such as monoamine oxidase (MAO), and in particular, by the enzymatic action of MAO-B. In particularly preferred embodiments, the pro-drug is preferentially converted to active drug by the enzymatic action of MAO-B, but remains substantially un-converted to active drug by the action of the related enzyme, MAO-A. In certain embodiments, the specificity of the multicomponent compound for MAO-B is at least about 10 times greater, more preferably, at least about 15 times greater, and more preferably still, about 20 times greater or more than for MAO-A. In illustrative embodiments, the inventors have designed multicomponent compounds that are at least about 10-fold more specific for MAO-B catalysis than for catalysis by MAO-A.

An exemplary substrate of MAO-B that is useful in the development of the tripartite compounds of the present invention is MPTP. MPTP, 1-methyl-4-phenyl-1,2,3,6-tetrahydropyridine, is shown in general formula 1:

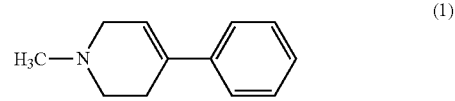

(1)

MPTP can be converted by MAO-B to MPP (1-methyl-4-phenylpyridinium), shown in general formula 2:

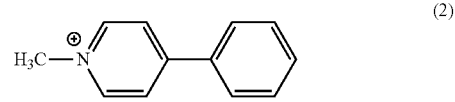

(2)

An exemplary chemotherapeutic compound that was employed in the development of the tripartite compounds of the present invention, MPTP was chemically linked to a nitrogen mustard, to form MP-MUS (I), (N,N-bis(2-chloro ethyl)-2-(1-methyl-1,2,3,6-tetrahydropyridin-4-yl) propanamide) (general formula 3). MP-MUS is composed of a mitochondrial targeting, or "seeker" moiety, MP, operably linked to a cytotoxic moiety, such as a nitrogen mustard, via a chemical linker. MP-MUS (3) has been shown to be effective in primary gliomal cell cultures.

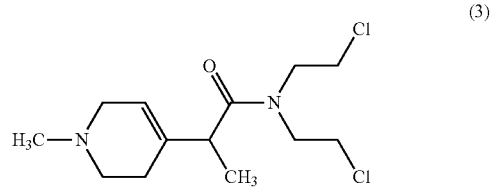

(3)

In these studies, MP-MUS (I) killed gliomal cells at chemotherapeutic dosages; collapsed the mitochondrial membrane potential, increased mitochondrial protein levels and caused large numbers of mtDNA breaks. The effects of the pro-drug were almost completely negated by the addition of the MAO-B specific inhibitor, selegiline.

In illustrative embodiments, the chemotherapeutic moiety is operably linked to the targeting/seeker moiety by at least one linker group, such as 2-methylpropanamide and cyclohexane, to provide a therapeutic/linker combination including one or more selected from the group consisting of bis(2-chloroethyl)[Linker-TP]amine, 1-[(2-R1-2-R2-2-[Linker-TN]ethyl)sulfanyl]-3-chloropropane, ({[(3-chloropropyl)sulfanyl]methyl})[Linker-TN]-R1-amine, 3-[Linker-TN]-4-(methanesulfonylmethoxy)butyl methanesulfonate, 1,10-dichloro-5-[Linker-TN]-2,9-diaza-1,10-diplatinadecane-1,1,10,10-tetramine, and 2,2-diamino-5-[Linker-TN]-1,3-dioxa-2-platinacyclohexane-4,6-dione.

Preferably, the first targeting/seeker moiety is specifically recognized as a substrate for a mammalian monoamine oxidase (MAO) enzyme, including for example MAO-A and MAO-B forms of the enzyme. In the practice of the invention, the targeting/seeker molecule confers selectivity to the compound, such that it confers to the compound at least two-fold (and preferably at least three-fold more, or even four-fold more or greater) greater specificity for one form of the MAO enzyme (preferably MAO-B), than for another form of the enzyme (e.g., MAO-A).

Through the action of MAO, the targeting/seeker moiety is converted to its corresponding 1-methyl-4-(X)-pyridinium cationic form, wherein the resulting 1-methyl-4-(X)-pyridinium cationic form of the targeting moiety facilitates an enhanced uptake of the compound across the mitochondrial membrane of a mammalian cell at a rate that is at least 10-fold (and preferably at least 15-fold, at least 20-fold, or at least 30-fold) higher than that of the corresponding non-ionic form of the targeting moiety. This increased ability of the targeting/seeker moiety to translocate the compound across the mitochondrial membrane (due substantially in part to the high electrical potential across that membrane) such that the presence of the 1-methyl-4-(X)-pyridinium cation facilitates accumulation of the compound in the mitochondria of a population of mammalian cells to which the compound has been administered, in an amount that is about 50-fold (any more preferably, at least about 100-fold, at least about 200-fold, or even about 500-fold) higher than the concentration of the compound that remains in the cytosolic fraction of such cells.

In exemplary embodiments, the targeting/seeker moiety is selected from the group consisting of 1-methyl-1,2,3,6-tetrahydropyridine and 1-cyclopropyl-1,2,3,6-tetrahydropyridin-.

Exemplary compounds in accordance with the present invention include, without limitation, 2-$R_3$—N—$R_2$—N—$R_1$-2-(1-X-1,2,3,6-tetrahydropyridin-4-yl) acetamide, 4-phenyl-1-X-1,2,3,6-tetrahydropyridine, 4-cyclohexyl-1-X-1,2,3,6-tetrahydropyridine, and 4-(5-$R_1$-4-$R_2$-3-$R_3$-furan-2-yl)-1-X-1,2,3,6-tetrahydropyridine, wherein $R_1$, $R_2$, $R_3$, and $R_5$, are each halogen, hydroxyl, oxo, cyano, nitro, amino, alkylamino, dialkylamino, alkyl, alkoxy, alkylthio, haloalkyl, aryl, arylalkyl, heteroaryl, heteroarylalkyl, heterocycle, heterocyclealkyl, —$NR_aR_b$, —$NR_aC(\!=\!O)R_b$, —$NR_aC(\!=\!O)NR_aNR_b$, —$NR_aC(\!=\!O)OR_b$—$NR_aSO_2R_b$, —$C(\!=\!O)R_a$, $C(\!=\!O)OR_a$, —$C(\!=\!O)NR_aR_b$, —$C(\!=\!O)NR_aR_b$, —$OR_a$, —$SR_a$, —$SOR_a$, —$S(\!=\!O)_2R_a$, —OS$(\!=\!O)_2$ $R_a$, —$S(\!=\!O)_2OR_a$, substituted alkyl, substituted aryl, substituted arylalkyl, substituted heterocycle, or substituted heterocyclealkyl; wherein $R_a$ and $R_b$ are the same or different and, are, independently, hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl, and further wherein X is a therapeutic moiety. In preferred embodiments, X is a chemotherapeutic drug selected from the group consisting of a nitrogen mustard, a sulfur mustard, a platin tetranitrate, cis-platin, or a derivative or salt thereof. In illustrative embodiments, the compound is MP-MUS.

In another aspect of the invention, a pharmaceutical composition is provided that includes one or more of the compound disclosed herein, admixed with one or more pharmaceutically-acceptable carriers, diluents, excipients, or any combination thereof, as described elsewhere herein. In some embodiments, the composition may further optionally include one or more other antineoplastic, cytotoxic, cytostatic, or chemotherapeutic agents, or any combination thereof. Exemplary agents include, without limitation, sulfans, platin tetranitrates, nitrogen mustards, sulfur mustards, cis-platin, topoisomerase inhibitors (including topoisomerase I and II inhibitors), as well as derivatives, analogs, salts, active metabolites, or combinations thereof.

In an exemplary embodiment, the one or more other antineoplastic agents is selected from the group consisting of camptothecin, irinotecan, temozolomide, vinblastine, docetaxel, etoposide, carmustine, lomustine, a nitrogen mustard, a sulfur mustard, an active metabolite of camptothecin (such as SN38), and any combination thereof.

The invention also provides a method of treating or ameliorating one or more symptoms of cancer in an animal in need thereof. Such a method generally includes at least the step of providing or administering to the animal, either systemically, or locally at one or more regions or sites within, or about the body of the animal an effective amount of at least a first chemotherapeutic compound disclosed herein, or an analog, an agonist, an antagonist, or a derivative or salt thereof, for a time sufficient to treat or ameliorate the one or more symptoms of the cancer in the animal.

In a further aspect, the invention also provides a method for inhibiting the growth of a cancer cell or tumor in an animal. This method, in an overall and general sense includes providing to one or more cells or tissues of the body of an animal in need thereof, an amount of one or more of the chemotherapeutic compound disclosed herein, or an analog, an agonist, an antagonist, or a derivative or salt thereof, in an amount and for a time effective to inhibit the growth of the cancer cell or the tumor.

In another aspect, the invention provides a method for treating cancer in a subject, and preferably in a human. In an overall and general sense, the method generally includes administering to the subject in need thereof a therapeutically-effective amount of one or more of the chemotherapeutic compounds disclosed herein, or an analog, an agonist, an antagonist, or a derivative or salt thereof; and administering one or more additional chemotherapeutics, or a therapeutically effective amount of an ionizing radiation, or combinations thereof.

The invention also provides a method of ameliorating one or more symptoms of cancer in an animal. Such methods generally include providing to the animal an effective amount of a chemotherapeutic composition that comprises one or more of the therapeutic compounds disclosed herein, or an analog, an agonist, an antagonist, or a derivative or salt thereof, and at least a first pharmaceutically-acceptable diluent, for a time sufficient to ameliorate the one or more symptoms of the cancer in the animal.

A further method is provided by the invention for altering, affecting, increasing, or improving the effectiveness of a chemotherapeutic agent in damaging or killing one or more types of cancer cells or tumors in an animal. This method generally involves chemically linking such an agent to a MAO-convertible, mitochondria-targeting/seeking drug delivery moiety to form a mitochondrially-targeted composition, and then providing an effective amount of the resulting chemotherapeutic composition to one or more cells, tissues, or organs of the animal, wherein the effectiveness of the composition for killing one or more cancer cells in the animal is greater than the effectiveness of the un-linked agent alone.

The invention also provides a method of targeting a chemotherapeutic agent to one or more cancer cell mitochondria in an animal in need of anti-cancer therapy. Such a method generally includes the process of chemically linking one or more mitochondrially-active, chemotherapeutic agents to one or more inactive pro-drugs that, when present in the mitochondria exhibit at least a first chemotherapeutic property (e.g., DNA damaging and/or DNA acylating activity). Such a compound is preferably convertible from its inactive pro-drug form to an active form by the enzymatic action of a mitochondrial MAO into the corresponding cationic form, which is then able to cross the mitochondrial membrane at a relatively high degree of efficiency, and in an amount that has resulting cytotoxic properties, and then providing an effective amount of the composition to one or more cells, tissues, or organs of the animal, wherein the level of chemotherapeutic agent localized to the mitochondria is substantially higher than the level of chemotherapeutic agent remaining in the cytosol of the one or more cancer cells. Such exemplary compounds include, without limitation, MP-MUS or APE-SN38.

In the practice of the present methods, the hyperproliferative condition is preferably one or more cancers, including without limitation, gliomal cancers, such as glioblastoma multiforme (GBM), recurrent glioblastoma multiforme (rGBM), astrocytoma, ependymoma, oligodendroglioma, brainstem glioma, or mixed glioma. Such cancers may be diagnosed as, or identified as, an advanced-stage or an advanced-grade type of cancer, including, without limitation, advanced-stage GBM. Such malignant gliomas may include, without limitation, one or more types of radiation-resistant glioma, or glioma stem cells.

Exemplary additional agents, which may be co-administered to the subject, include, without limitation, one or more conventional anti-cancer drugs, such as camptothecin, temozolomide, carmustine, and combinations thereof. Alternatively, the methods of the present invention may also include one or more surgical interventions, such as tumor resection, or may further optionally include one or more courses of therapeutically effective ionizing radiation (i.e., radiation therapy).

The invention also provides pharmaceutical composition for use in the therapy of cancer in an animal subject, wherein the composition comprises one or more of the chemotherapeutic compounds disclosed herein, and may include such a use for preventing, treating, or ameliorating one or more symptoms of malignant glioma in a human subject.

In another aspect, the invention provides a MAO-convertible (and in particular, a MAO-B-convertible) tetrahydropyridine chemotherapeutic targeting/seeking moiety operably linked to at least a first chemotherapeutic agent. Such an agent may include, without limitation, a nitrogen mustard, a sulfur mustard, a sulfan, cis-platin, a platin tetranitrate derivative, temozolomide, camptothecin, carmustine, lomustine, or any derivative or analog thereof. Preferably, the MAO-B convertible tetrahydropyridine chemotherapeutic targeted delivery compound has the general formula 1-methyl-4-(X)-pyridine, wherein X is as defined as in FIG. 30. In exemplary embodiments, the MAO-B convertible tetrahydropyridine chemotherapeutic delivery compound is MP-MUS or APE-SN38.

In the practice of the invention, "seeker/linker/warhead" tripartite compounds of the present invention are preferably combined with one or more pharmaceutically-acceptable vehicles or carriers to provide therapeutic medicament compositions that find particular utility in the treatment and/or amelioration of at least a first symptom of one or more mammalian (and in particular, human) diseases, dysfunctions, disorders, abnormal conditions, and the like. In a particularly preferred embodiment, these MAO-converting pro-drug compounds may be provided in pharmaceutical compositions, suitable for delivery to an animal for use in the diagnosis, treatment, prevention, and/or ameliorating at least one or more symptoms of at least a first hyperproliferative-related disorder in an animal, and preferably a disorder including mammalian cancers, such as human glioma, and the like.

The invention also provides a method of altering, affecting, destroying, or killing one or more mammalian cells within or about the body of an animal that has, is suspected of having, or has been diagnosed with one or more forms of mammalian cancer. Such methods generally involve providing to one or more animal cells a therapeutically-effective amount of one or more of the disclosed chemotherapeutic formulations for a time sufficient to treat, and/or ameliorate the one of more symptoms of such a disease.

Also provided herein are methods of altering, modulating, controlling, increasing, and/or attenuating at least one component, pathway, enzyme, or step involved in the process of hyperproliferative cell grown within or about the body of an animal, by providing to one or more cells, tissues, and/or organs of a subject in need thereof an effective amount of one of more of the disclosed therapeutic compositions for a time effective to alter, modulate, control, increase, and/or attenuate at least one component, pathway, enzyme, or step involved in the process of hyperproliferative cell growth within such cells, tissues, organ, and/or body.

Further provided herein are methods of treating, preventing, and/or ameliorating at least one symptom of a mammalian cancer, including, without limitation, human gliomas. Further provided herein are methods and pharmaceutical formulations for controlling the rate, extent, and/or metabolism of at least a first mammalian cell, in one or more cancers, solid tumors, and the like. In certain embodiments, the method generally includes administration to such cells and/or tissues a first chemotherapeutic compound in accordance with the present invention, in an amount and for a time effective to disrupt, damage, alter, or impair synthesis of one or more mitochondrial nucleotides (for example, by inducing DNA damage through one or more DNA-acylating "warhead" moieties as described herein), to facilitate sufficient damage to the function of such mitochondria (and the cells in which they are located) to disrupt or kill one or more such cells (and preferably, part or all of a mammalian tumor containing such cells) within or about the body of an animal, in an amount and for a time sufficient to facilitate killing of the cancer, and/or destruction of the cancerous tumor within the body of a patient receiving such therapy.

Also provided herein are methods of treating, preventing, and/or ameliorating at least one symptom of a human hyperproliferative disorder (such as a mammalian glioma and the like) within one or more (and preferably within a plurality) of cancerous cells, tissues, tumors, and the like in an animal undergoing therapy and/or cancer treatment. In certain embodiments, the disclosed multifunctional compounds will be designed such that an inactive pro-drug form of the compound may be delivered to the animal, and then, through the intracellular action of the enzyme MAO, facilitate conversion of the pro-drug, to an active chemotherapeutic metabolite that is effective to control, prevent, or facilitate destruction of one or more cancerous cells populations within the body of the patient undergoing treatment. In such embodiments, the method generally involves administration of at least a first MAO-activatable compound to the animal in an amount and time sufficient to alter the expression or modulate the activity of one or more hyperproliferative, cancerous cells. While the methods are likely to provide benefit for a variety of oncologically-related conditions, the concentration of such activated "warhead" chemotherapeutic agents in the mitochondria of cancer cells, this mitochondrial membrane potential-facilitating accumulation in the cancer cells, necessarily provides advantageous properties compared to conventional chemotherapeutic agents, in that it facilitates lower whole-body doses of the agent to the animal, and preferential facilitates activation of the chemotherapeutic agent by the activity of mitochondrial MAO enzymes in cancerous cells and/or tumorigenic tissues. Such is particularly contemplated to be desirable when localized destruction or inactivation of particular cancer cell/tumor populations within the body of an animal is sought.

In related aspects, the compounds and compositions of the present invention may be utilized to diminish the activity of, or bring about the destruction of particular types of cells within the body of an animal receiving such compositions, either in a targeted (i.e., localized), or a generalized (i.e., systemic) administration. In such embodiments, the method generally involves administration of at least a first inactive pro-drug compound in an amount and time sufficient to diminish or inhibit the activity of one or more types of tumor cells within the body of an animal selected to receive the treatment, wherein the action of one or more cellular monoamine oxidases results in the conversion of the inactive pro-drug into an active chemotherapeutic metabolite that is preferentially active in the mitochondria of such cells.

Accordingly, in light of the present teachings, pharmaceutical compositions can now be designed that comprise a "seeker" moiety linked to a "warhead" (directly, or by one or more chemical linkers) that are MAO-activatable.

Chemotherapeutic Compounds and Pharmaceutical Formulations Thereof

The compounds of the present invention, as well as composition comprising them may be employed in the practice of the invention as a single cancer treatment modality, or alternatively may be combined with one or more additional therapeutic, diagnostic, and/or prophylactic agents, including, without limitation, one or more proteins, peptides, polypeptides (including, without limitation, enzymes, antibodies, antigens, antigen binding fragments etc.); RNA molecules (including, without limitation, siRNAs, iRNAs, mRNAs, tRNAs, and catalytic RNAs, such as ribozymes, and the like), DNA molecules (including, without limitation, oligonucleotides, polynucleotides, genes, coding sequences (CDS), introns, exons, plasmids, cosmids, phagemids, baculovirus, vectors [including, without limitation, viral vectors, virions, viral particles and such like]); peptide nucleic acids, detection agents, imaging agents, contrast agents, detectable gas, radionuclides, or such like, and one or more additional chemotherapeutic agents, surgical intervention (e.g., tumor resection), radiotherapy, and the like, or any combination thereof as part of a multifactorial, or multifocal treatment plan for the affected patient.

The compositions disclosed herein may also further optionally include one or more additional active ingredients, including, without limitation, one or more anti-cancer agents, one or more anti-tumorigenic agents, one or more antineoplastic or cytotoxic agents, one or more transcription factors, immunomodulating agents, immunostimulating agents, neuroactive agents, antiinflammatory agents, chemotherapeutic agents, hormones, so called "trophic factors," cytokines, chemokines, receptor agonists or antagonists, or such like, or any combination thereof.

The chemotherapeutic formulations of the present invention may also further optionally include one or more additional components to aid, facilitate, or improve delivery of the pro-drug and/or active metabolite preferably to the mitochondria of cancerous cells, including, without limitation, one or more liposomes, particles, lipid complexes, and may further optionally include one or more binding agents, cell surface active agents, surfactants, lipid complexes, niosomes, ethosomes, transferosomes, phospholipids, sphingolipids, sphingosomes, or any combination thereof, and may optionally be provided within a pharmaceutical formulation that includes one or more nanoparticles, microparticles, nanocapsules, microcapsules, nanospheres, microspheres, or any combination thereof.

Preferably, the chemotherapeutic compounds of the present invention, as well as salts, analogs, and/or derivatives thereof will generally be formulated for systemic and/or localized administration to an animal, or to one or more cells or tissues thereof, and in particular, will be formulated for systemic and/or localized administration to a mammal, or to one or more cancerous cells, tumor tissues, or affected organs thereof. In certain embodiments, the compounds and methods disclosed herein will find particular use in the systemic and/or localized administration of one or more antineoplastic agents to one or more cells or tissues of a human being.

Preferably, drug-delivery formulations of the active compounds disclosed herein will be at least substantially stable at a pH from about 4.2 to about 8.2, and more preferably, will be substantially stable at a pH of from about 5 to about 7.5. Preferably, the active ingredient(s) and targeted drugs will be substantially active at physiological conditions of the animal into which they are being administered.

The present invention also provides for the use of one or more of the disclosed pharmaceutical compositions in the manufacture of a medicament for therapy and/or for the amelioration of one or more symptoms of a disease, disorder, dysfunction, or condition, and particularly for use in the manufacture of a medicament for treating, one or more diseases, dysfunctions, or disorders such as gliomal cancers and tumors in a mammal, and, in a human mammal in particular.

The present invention also provides for the use of one or more of the disclosed chemotherapeutics in the manufacture of a medicament for the treatment of cancer, and in particular, human gliomas. In certain embodiments, the invention also provides "seeker" compounds that may be linked to one or more novel or existing chemotherapeutic compositions to facilitate an improvement in the treatment or prognosis of a mammalian cancer, and a human glioma in particular.

Chemotherapeutic Methods

Another important aspect of the present invention concerns methods for using the disclosed MAO-activatable pro-drug compositions for treating or ameliorating the symptoms of disease, disorder, dysfunction, or deficiency in a mammal having, suspected of having, or at risk for developing such a condition, and in particular for those mammalian diagnosed with one or more gliomal cancers. Such methods generally involve administering to a mammal (and in particular, to a human in need thereof), one or more of the disclosed anticancer compositions, in an amount and for a time sufficient to treat (or, alternatively ameliorate one ore more symptoms of) gliomal cancers in an affected mammal.

In certain embodiments, the therapy described herein may be provided to the animal as a single treatment modality, as a single administration, or alternatively provided to the patient in multiple administrations over a period of from several hours to several days, from several days to several weeks, or even over a period of several weeks to several months or longer, as needed to treat the cancer. In some aspects, it may be desirable to continue the treatment throughout the lifetime of the patient. In other embodiments, it may be desirable to provide the therapy in combination with one or more existing, or conventional, treatment regimens.

Chemotherapeutic Kits

Kits including one or more of the disclosed chemotherapeutic compositions; and instructions for using the kit also represent preferred aspects of the present disclosure. Such kits may further include one or more of the disclosed anti-cancer compounds, either alone, or in combination with one or more additional therapeutic compounds, pharmaceuticals, and such like.

The kits of the invention may be packaged for commercial distribution, and may further optionally include one or more delivery devices adapted to deliver the chemotherapeutic composition(s) to an animal (e.g., syringes, injectables, and the like). Such kits typically include at least one vial, test tube, flask, bottle, syringe or other container, into which the pharmaceutical composition(s) may be placed, and preferably suitably aliquotted. Where a second pharmaceutical is also provided, the kit may also contain a second distinct container into which this second composition may be placed. Alternatively, the plurality of pharmaceutical compositions disclosed herein may be prepared in a single mixture, such as a suspension or solution, and may be packaged in a single container, such as a vial, flask, syringe, catheter, cannula, bottle, or other suitable single container.

The kits of the present invention may also typically include a retention mechanism adapted to contain or retain the vial(s) or other container(s) in close confinement for commercial sale, such as, e.g., injection or blow-molded plastic containers into which the desired vial(s) or other container(s) may be retained to minimize or prevent breakage, exposure to sunlight, or other undesirable factors, or to permit ready use of the composition(s) included within the kit.

Preparation of Medicaments

Another important aspect of the present invention concerns methods for using the disclosed chemotherapeutic agents, as well as pharmaceutical formulations including one or more of them, in the preparation of one or more medicaments for treating or ameliorating the symptoms of cancer in an animal, such as a vertebrate mammal.

Such use generally involves administration to an animal in need thereof one or more of the disclosed compositions, in an amount and for a time sufficient to prevent, treat, lessen, or cure the disease, disorder, dysfunction, condition, or deficiency in the affected animal, and/or to ameliorate one or more symptoms thereof.

Compositions including one or more of the disclosed pharmaceutical formulations that include at least one MAO-convertible chemotherapeutic composition also form an important part of the present invention. Particularly desirable, are those formulations that in addition to including one or more such chemotherapeutic agents, also further include at least a first pharmaceutically-acceptable excipient, making the compositions desirable for use in cancer therapy of a mammal, and in the treatment of humans, in particular.

Such formulations may optionally further include one or more additional active ingredients, detection reagents, vehicles, additives or adjuvants, radionuclides, gases, or fluorescent labels as may be suitable for administration to an animal. Such routes of administration are known to and may be selected by those of ordinary skill in the art, and include, without limitation, delivery devices including intramuscular, intravenous, intra-arterial, intrathecal, intracavitary, intraventricular, subcutaneous, or direct delivery, administration, and/or injection into an organ, tissue site, or population of cells in the recipient animal.

The invention also provides methods for providing a therapeutic or prophylactic amount of an MAO-activatable compound to at least a first population of cells or to one or more tissues within the body of a mammal, with the method generally including providing to a mammal in need thereof an effective amount of a anticancer composition as disclosed herein and for a time effective to provide the desired therapy and/or prophylaxis in the selected cells or tissue of the mammal.

Pharmaceutical Formulations

In certain embodiments, the present invention concerns formulation of one or more chemotherapeutic compounds in a pharmaceutically acceptable composition for administration to a cell or an animal, either alone, or in combination with one or more other modalities of diagnosis, prophylaxis and/or therapy. The formulation of pharmaceutically acceptable excipients and carrier solutions is well known to those of ordinary skill in the art, as is the development of suitable dosing and treatment regimens for using the particular compositions described herein in a variety of treatment regimens.

In certain circumstances it will be desirable to deliver the chemotherapeutic compositions disclosed herein in suitably-formulated pharmaceutical vehicles by one or more standard delivery devices, including, without limitation, subcutaneously, parenterally, intravenously, intramuscularly, intrathecally, orally, intraperitoneally, transdermally, topically, by oral or nasal inhalation, or by direct injection to one or more cells, tissues, or organs within or about the body of an animal.

The methods of administration may also include those modalities as described in U.S. Pat. Nos. 5,543,158; 5,641,515, and 5,399,363, each of which is specifically incorporated herein in its entirety by express reference thereto. Solutions of the active compounds as freebase or pharmacologically acceptable salts may be prepared in sterile water, and may be suitably mixed with one or more surfactants, such as hydroxypropylcellulose. Dispersions may also be prepared in glycerol, liquid polyethylene glycols, oils, or mixtures thereof. Under ordinary conditions of storage and use, these preparations contain a preservative to prevent the growth of microorganisms.

For administration of an injectable aqueous solution, without limitation, the solution may be suitably buffered, if necessary, and the liquid diluent first rendered isotonic with sufficient saline or glucose. These particular aqueous solutions are especially suitable for intravenous, intramuscular, subcutaneous, transdermal, subdermal, and/or intraperitoneal administration. In this regard, the compositions of the present invention may be formulated in one or more pharmaceutically acceptable vehicles, including for example sterile aqueous media, buffers, diluents, etc. For example, a given dosage of active ingredient(s) may be dissolved in a particular volume of an isotonic solution (e.g., an isotonic NaCl-based solution), and then injected at the proposed site of administration, or further diluted in a vehicle suitable for intravenous infusion (see, e.g., "*Remington's Pharmaceutical Sciences*" 15th Edition, pp. 1035-1038 and 1570-1580). While some variation in dosage will necessarily occur depending on the condition of the subject being treated, the extent of the treatment, and the site of administration, the person responsible for administration will nevertheless be able to determine the correct dosing regimens appropriate for the individual subject using ordinary knowledge in the medical and pharmaceutical arts.

Sterile injectable compositions may be prepared by incorporating the disclosed drug delivery vehicles in the required amount in the appropriate solvent with several of the other ingredients enumerated above, as required, followed by filtered sterilization. Generally, dispersions can be prepared by incorporating the selected sterilized active ingredient(s) into a sterile vehicle that contains the basic dispersion medium and the required other ingredients from those enumerated above. The compositions disclosed herein may also be formulated in a neutral or salt form. Pharmaceutically-acceptable salts include the acid addition salts (formed with the free amino groups of the protein), and which are formed with inorganic acids such as, without limitation, hydrochloric or phosphoric acids, or organic acids such as, without limitation, acetic, oxalic, tartaric, mandelic, and the like. Salts formed with the free carboxyl groups can also be derived from inorganic bases such as, without limitation, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation, and in such amount as is effective for the intended application. The formulations are readily administered in a variety of dosage forms such as injectable solutions, topical preparations, oral formulations, including sustain-release capsules, hydrogels, colloids, viscous gels, transdermal reagents, intranasal and inhalation formulations, and the like.

The amount, dosage regimen, formulation, and administration of the chemotherapeutic compositions disclosed herein will be within the purview of the ordinary-skilled artisan having benefit of the present teaching. It is likely, however, that the administration of a therapeutically-effective (i.e., a pharmaceutically-effective) amount of the disclosed anti-cancer compositions may be achieved by a single administration, such as, without limitation, a single injection of a sufficient quantity of the delivered agent to provide the desired benefit to the patient undergoing such a procedure. Alternatively, in some circumstances, it may be desirable to provide multiple, or successive administrations of the MAO-activatable, anti-cancer compositions disclosed herein, either over a relatively short, or even a relatively prolonged period, as may be determined by the medical practitioner overseeing the administration of such compositions to the selected individual.

Typically, formulations of one or more of the active ingredients described herein will contain at least a chemotherapeutically-effective amount of the active agent(s). Preferably, the formulation may contain at least about 0.001% of each active ingredient, preferably at least about 0.01% of the active ingredient, although the percentage of the active ingredient(s) may, of course, be varied, and may conveniently be present in amounts from about 0.01 to about 90 weight % or volume %, or from about 0.1 to about 80 weight % or volume %, or more preferably, from about 0.2 to about 60 weight % or volume %, based upon the total formulation. Naturally, the amount of active compound(s) in each composition may be prepared in such a way that a suitable dosage will be obtained in any given unit dose of the compound. Factors such as solubility, bioavailability, biological $t_{1/2}$, route of administration, product shelf life, as well as other pharmacological considerations will be contemplated by one of ordinary skill in the art of preparing such pharmaceutical formulations, and as such, a variety of dosages and treatment regimens may be desirable.

Administration of the chemotherapeutic compositions disclosed herein may be administered by any effective method, including, without limitation, by parenteral, intravenous, intramuscular, or even intraperitoneal administration as described, for example, in U.S. Pat. Nos. 5,543,158, 5,641,515 and 5,399,363 (each of which is specifically incorporated herein in its entirety by express reference thereto). Solutions of the active compounds as free-base or pharmacologically acceptable salts may be prepared in water suitably mixed with a surfactant, such as hydroxypropylcellulose, or other similar fashion. The pharmaceutical forms adapted for injectable administration include sterile aqueous solutions or dispersions, and sterile powders for the extemporaneous preparation of sterile injectable solutions or dispersions including without limitation those described in U.S. Pat. No. 5,466,468 (which is specifically incorporated herein in its entirety by express reference thereto). In all cases, the form must be sterile and must be fluid to the extent that easy syringability exists. It must be at least sufficiently stable under the conditions of manufacture and storage, and must be preserved against the contaminating action of microorganisms, such as viruses, bacteria, fungi, and such like.

The carrier(s) can be a solvent or dispersion medium including, without limitation, water, ethanol, polyol (e.g., glycerol, propylene glycol, and liquid polyethylene glycol, and the like, or a combination thereof), one or more vegetable oils, or any combination thereof, although additional pharmaceutically-acceptable components may be included.

Proper fluidity of the pharmaceutical formulations disclosed herein may be maintained, for example, by the use of a coating, such as e.g., a lecithin, by the maintenance of the required particle size in the case of dispersion, by the use of a surfactant, or any combination of these techniques. The inhibition or prevention of the action of microorganisms can be brought about by one or more antibacterial or antifungal agents, for example, without limitation, a paraben, chlorobutanol, phenol, sorbic acid, thimerosal, or the like. In many cases, it will be preferable to include an isotonic agent, for example, without limitation, one or more sugars or sodium chloride, or any combination thereof. Prolonged absorption of the injectable compositions can be brought about by the use in the compositions of agents delaying absorption, for example without limitation, aluminum monostearate, gelatin, or a combination thereof.

While systemic administration is contemplated to be effective in many embodiments of the invention, it is also contemplated that formulations of the disclosed drug delivery compositions may be suitable for direct injection into one or more organs, tissues, or cell types in the body. Administration of the disclosed compositions may be conducted using suitable means, including those known to the one of ordinary skill in the relevant medical arts. For example, the chemotherapeutic agents disclosed herein may be administered using any method as conventionally employed in the medical arts. In particular embodiments, the disclosed chemotherapeutic agents, and/or their pro-drug forms, may be formulated using one or more pharmaceutical buffers, vehicles, or diluents, and intended for administration to a mammal through a suitable route.

The pharmaceutical formulations disclosed herein are not in any way limited to use only in humans, or even to primates, or mammals. In certain embodiments, the methods and compositions disclosed herein may be employed using avian, amphibian, reptilian, or other animal species. In preferred embodiments, however, the compositions of the present invention are preferably formulated for administration to a mammal, and in particular, to humans, in a variety of diagnostic, therapeutic, and/or prophylactic regimens. The compositions disclosed herein may also be provided in formulations that are acceptable for veterinary administration, including, without limitation, to selected livestock, exotic or domesticated animals, companion animals (including pets and such like), non-human primates, as well as zoological or otherwise captive specimens, and such like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates. The following drawings form part of the present specification and are included to demonstrate certain aspects of the present invention.

The invention may be better understood by reference to the following description taken in conjunction with the accompanying drawings, in which like reference numerals identify like elements, and in which:

FIG. 1 illustrates how MPTP is initially oxidized by MAO, with a hydrogen atom (from the $C_6$ position on the tetrahydropyridine) and an electron from the amine to form 1-methyl-4-phenyl-2,3-dihydropyridin-1-ium (MPDP$^+$);

FIG. 2A and FIG. 2B illustrate exemplary mitochondrial-destroying warhead delivery compounds useful in the practice of the present invention. In particular, MP-MUS (N,N-bis(2-chloroethyl)-2-(1-methyl-1,2,3,6-tetrahydropyridin-4-yl)propanamide)/P+-MUS (I) (4-(1-[bis (2-chloroethyl) carbamoyl]ethyl)-1-methylpyridin-1-ium) are illustrated;

Figure 2B:
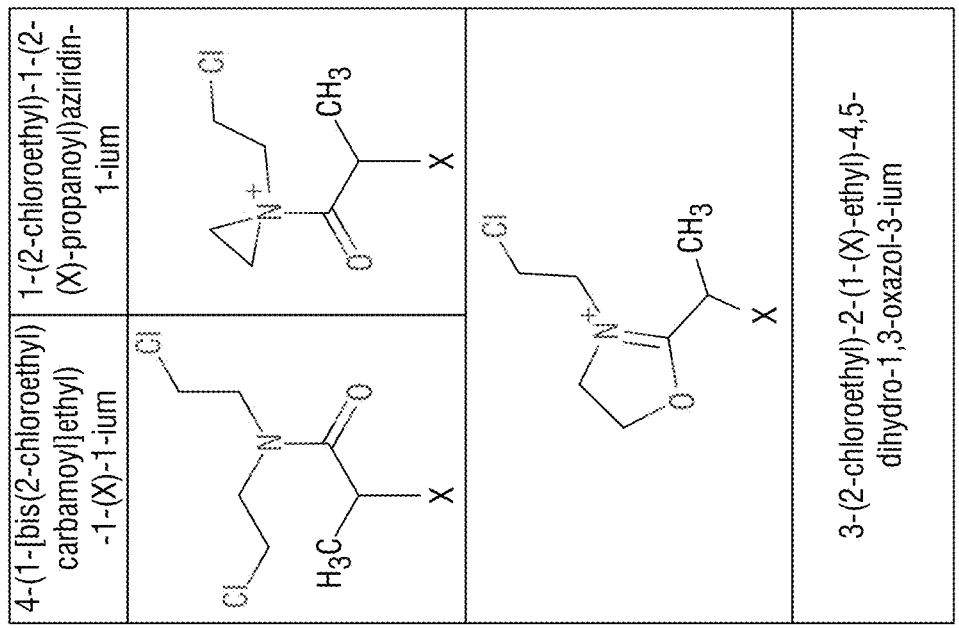
Figure 2A:
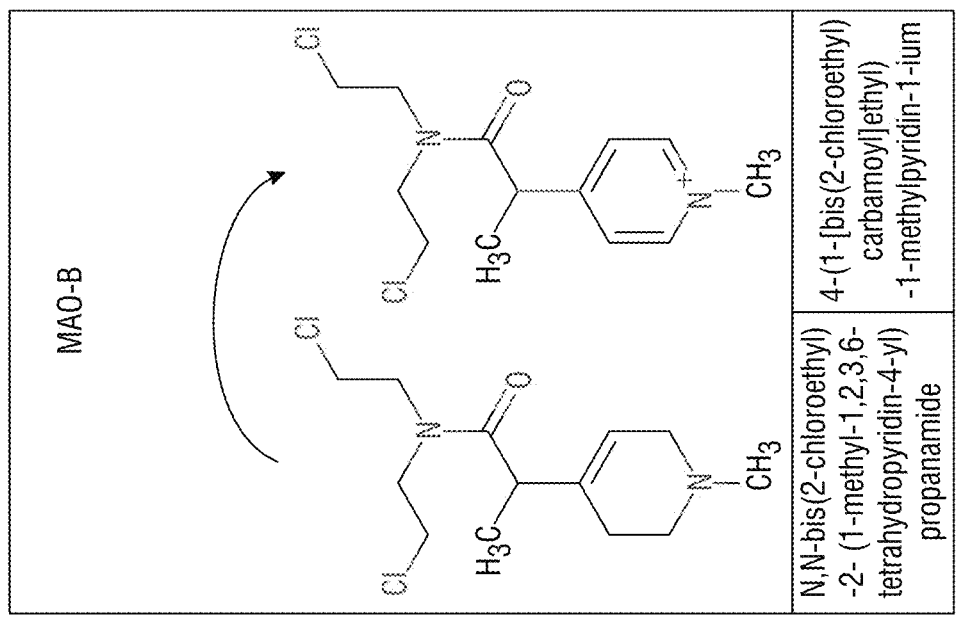
Figure 6A:
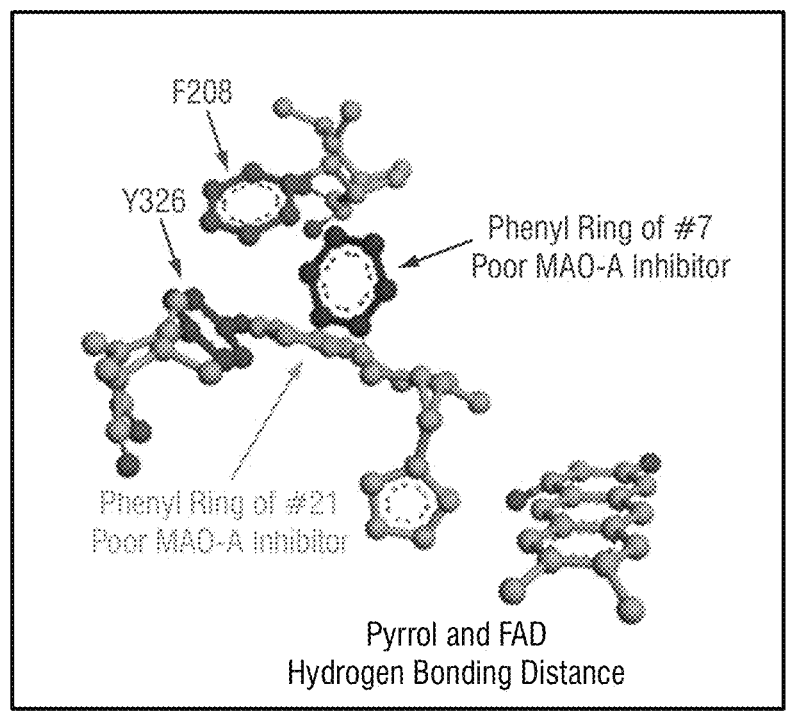
Figure 6B:
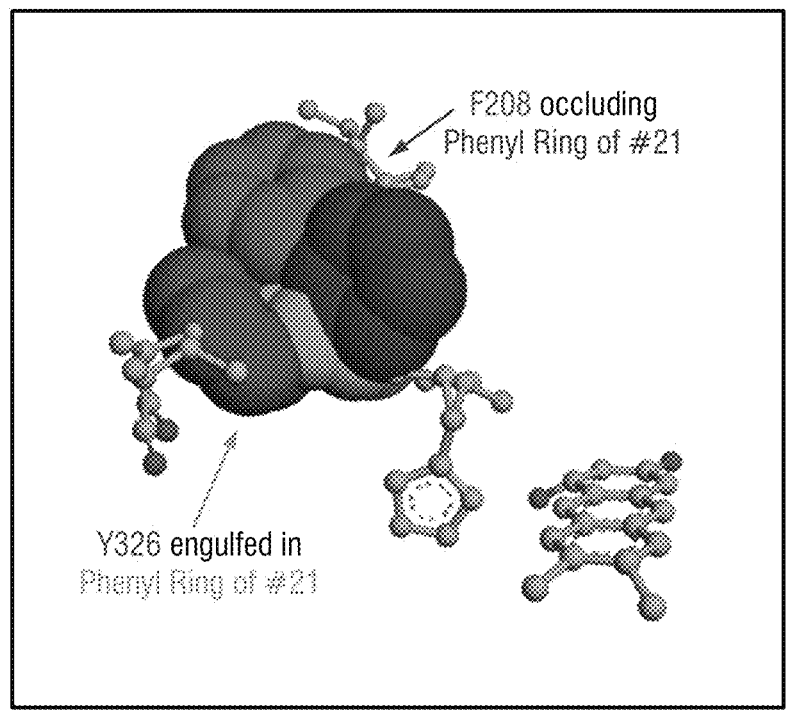
Figure 7:
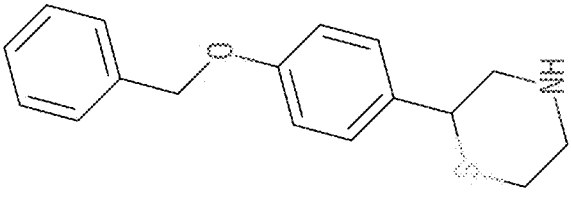
Figure 8A:
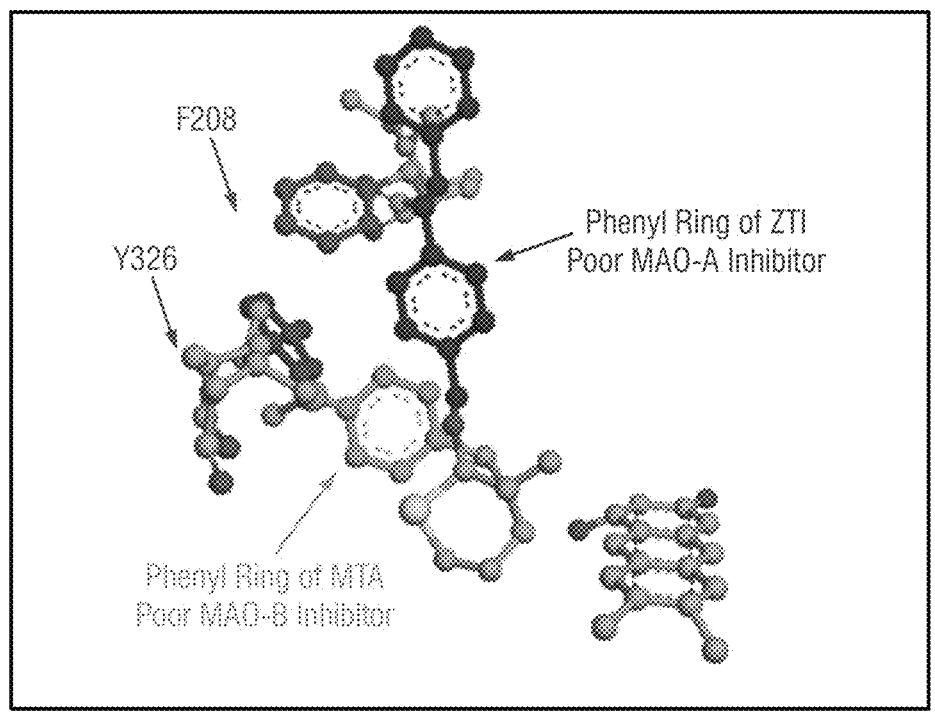
Figure 8B:
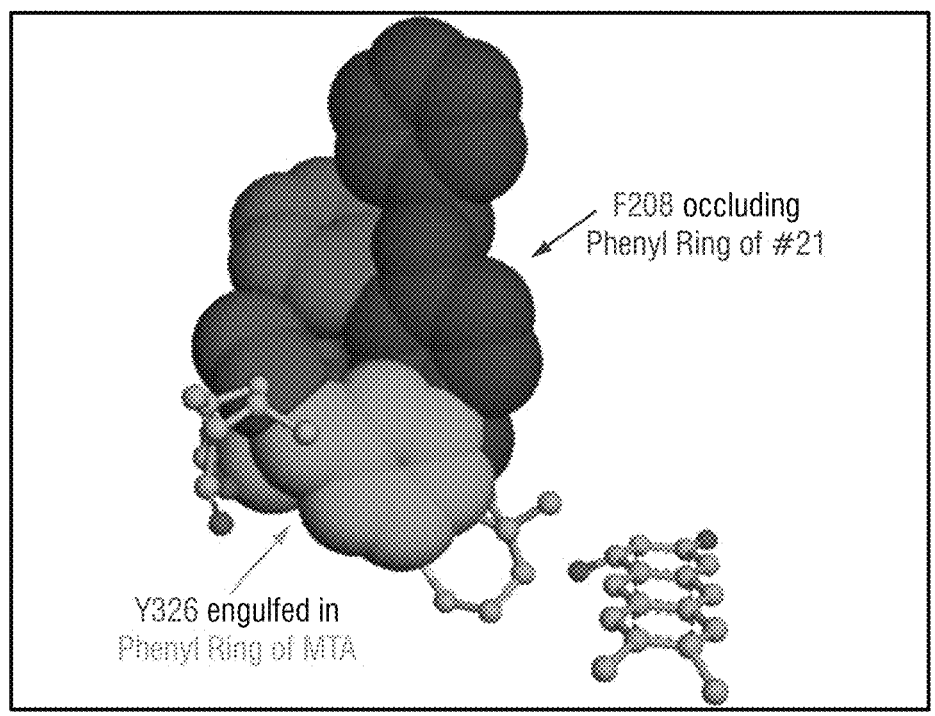
Figure 10:
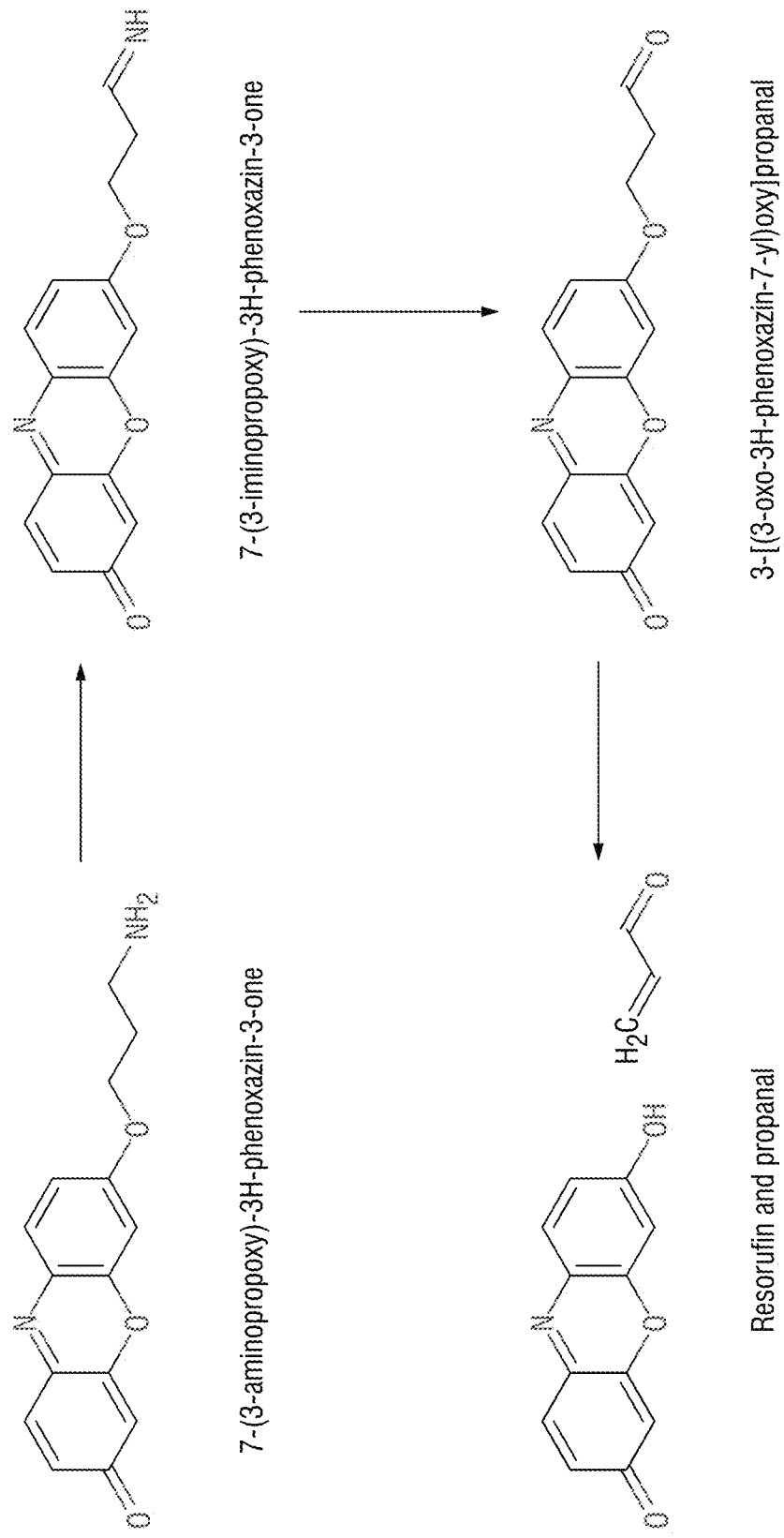
Figure 11A:
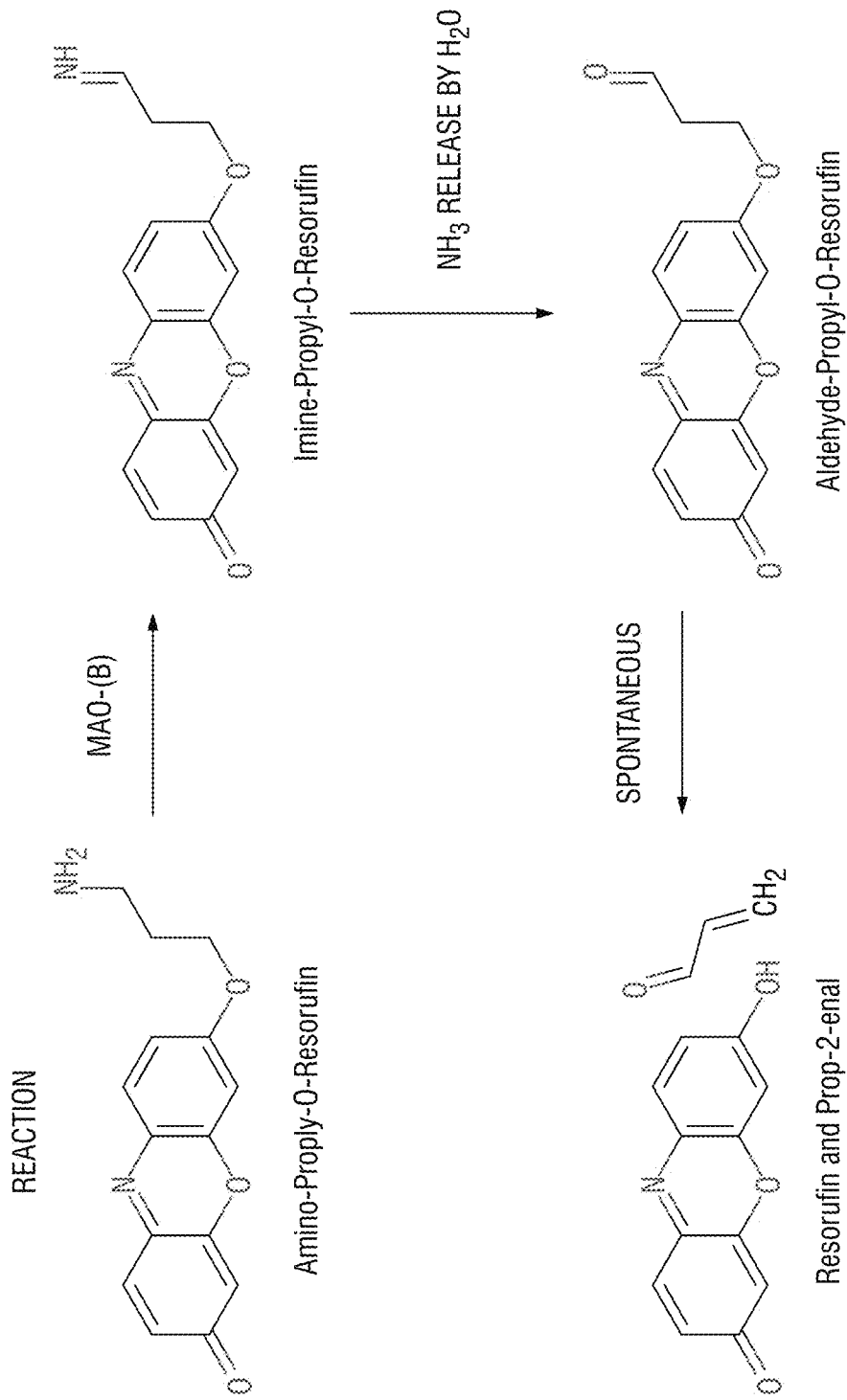
Figure 11B:
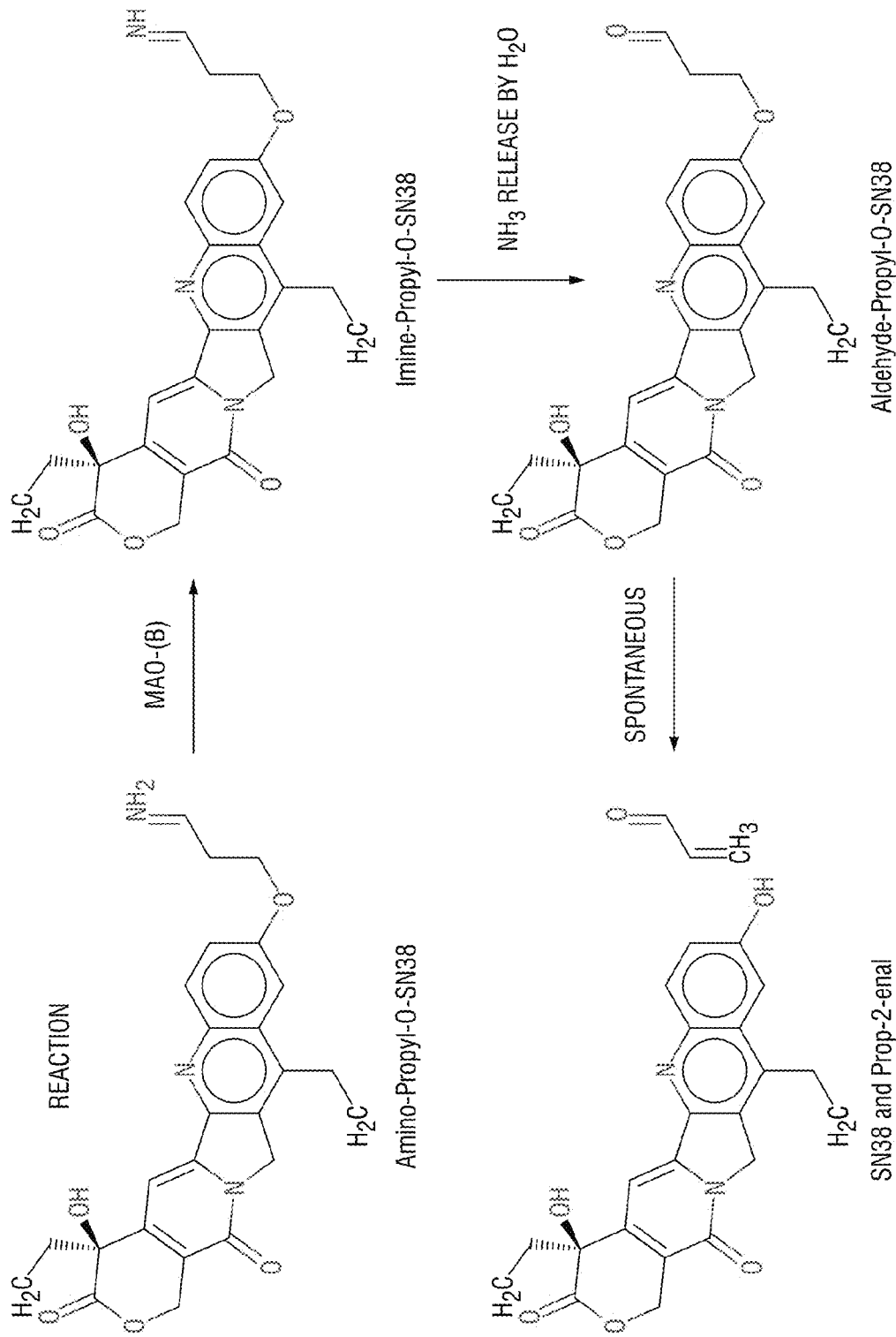
Figure 11C:
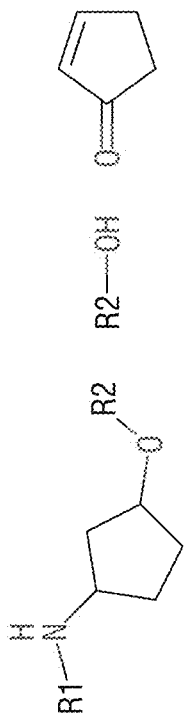
Figure 11E:
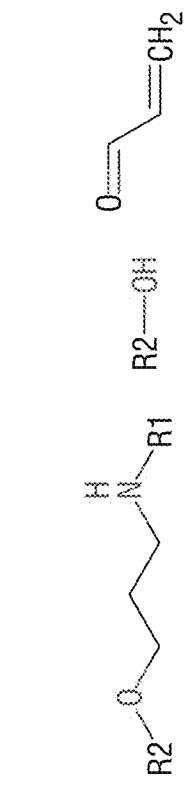
Figure 11D:
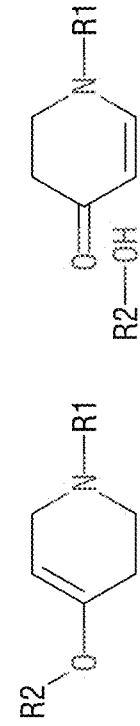
Figure 11F:
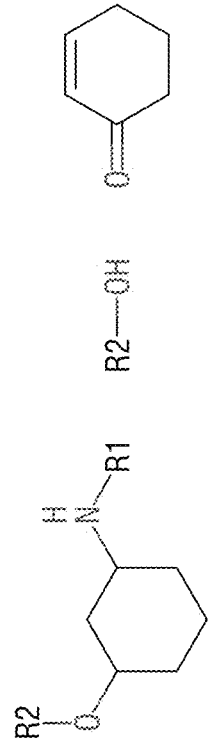
Figure 11G:
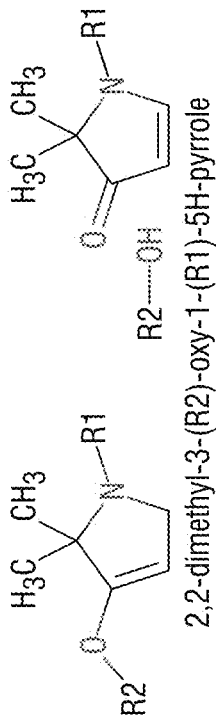
Figure 11H:
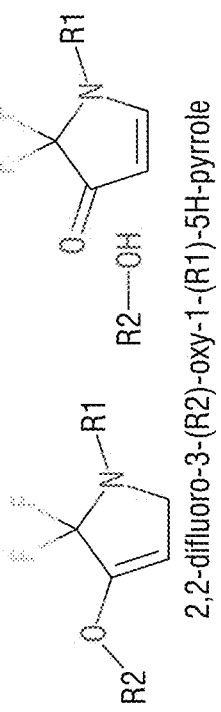
Figure 12:
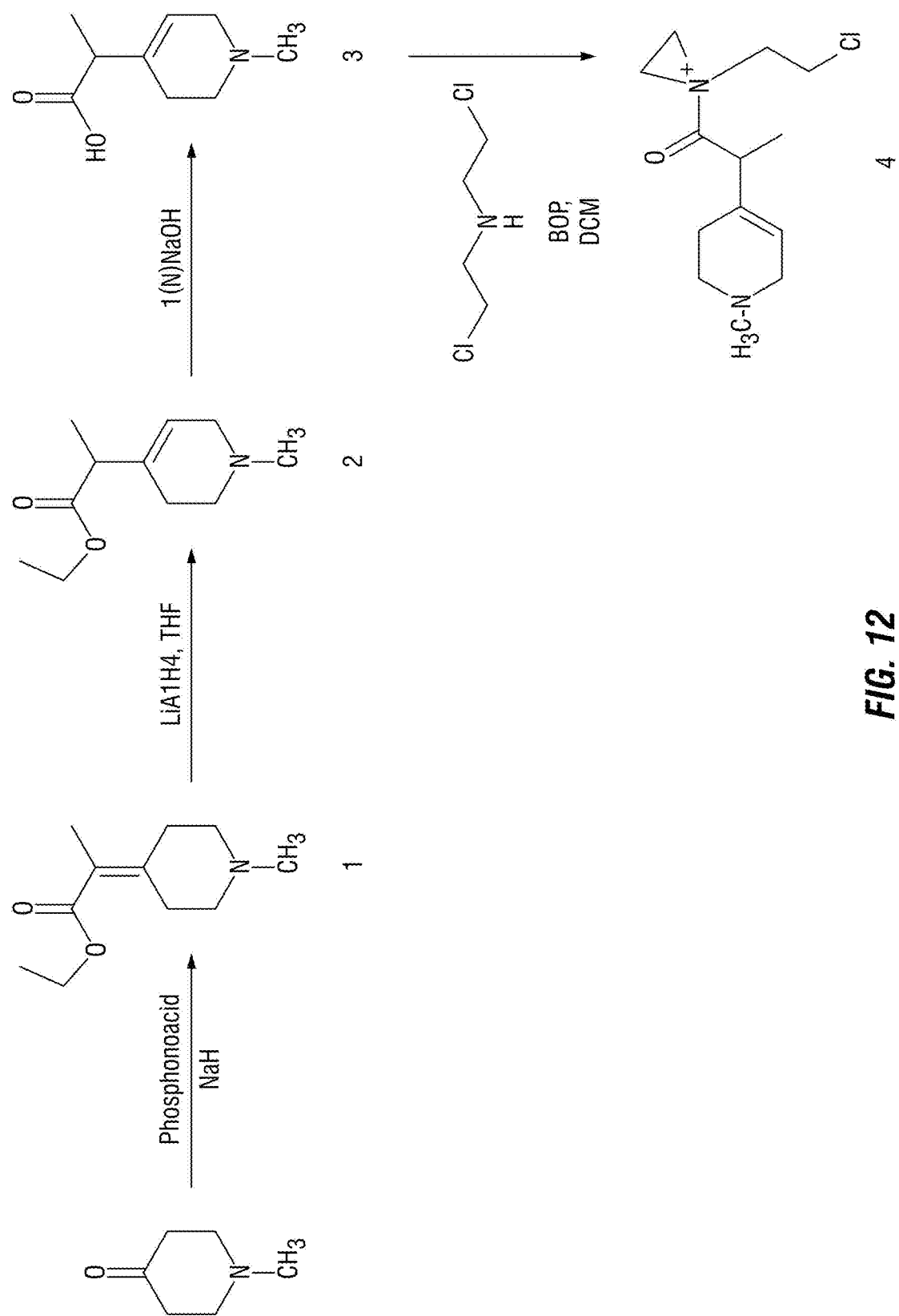
Figure 13A:
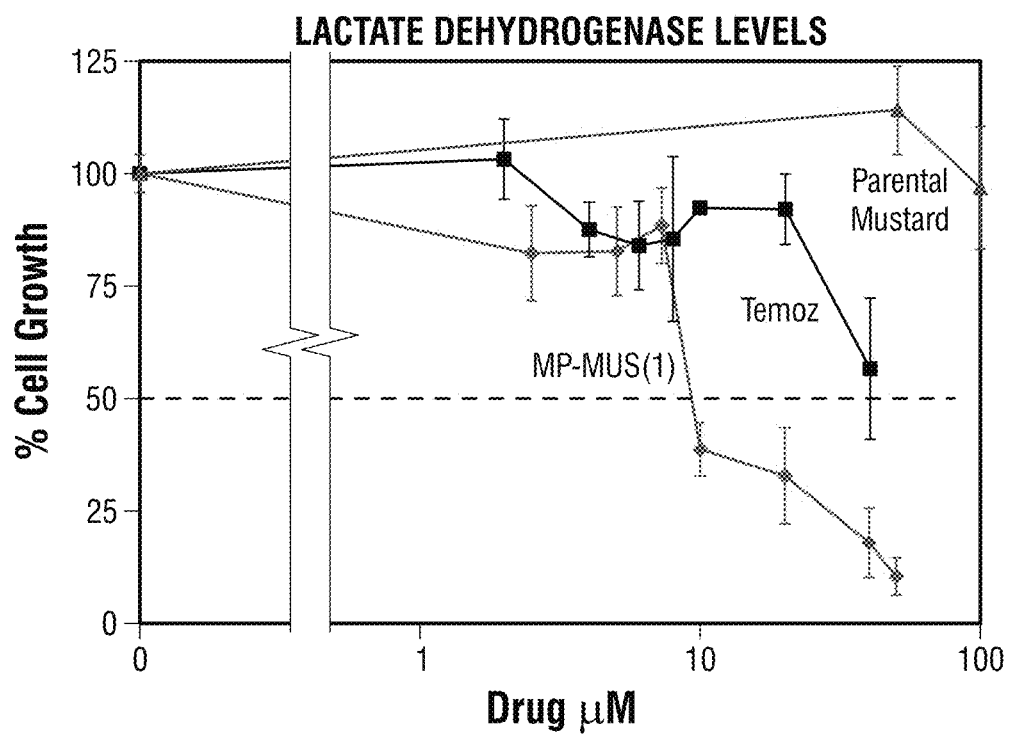
Figure 13B:
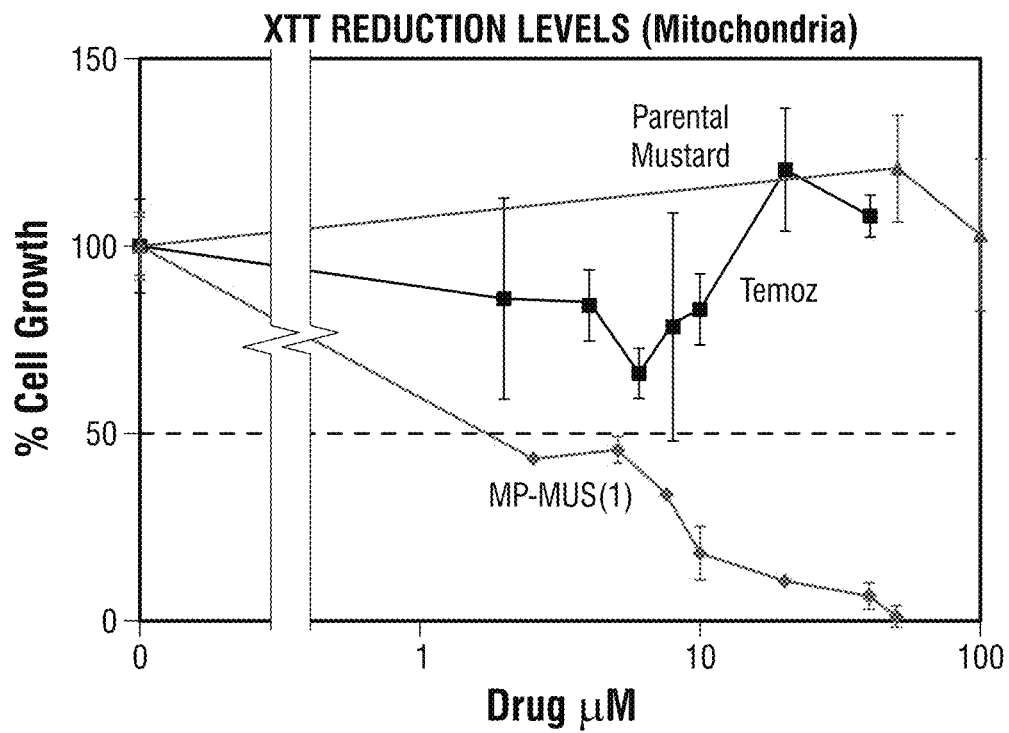
Figure 14A:
Figure 14B:
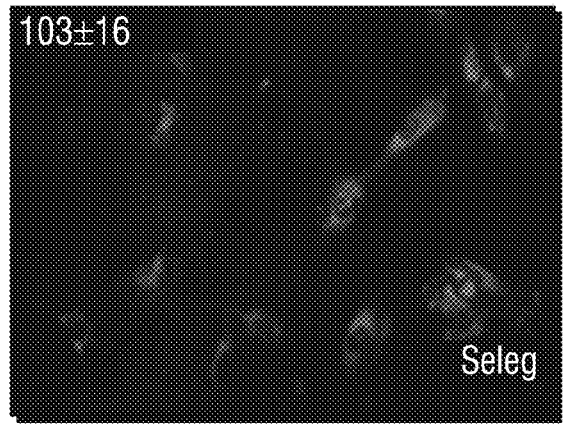
Figure 14C:
Figure 14D:
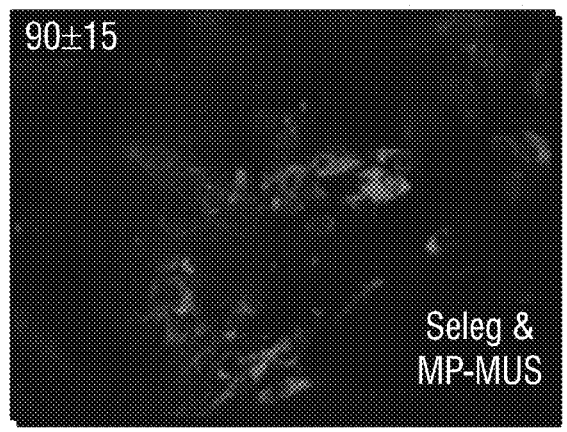
Figure 15A:
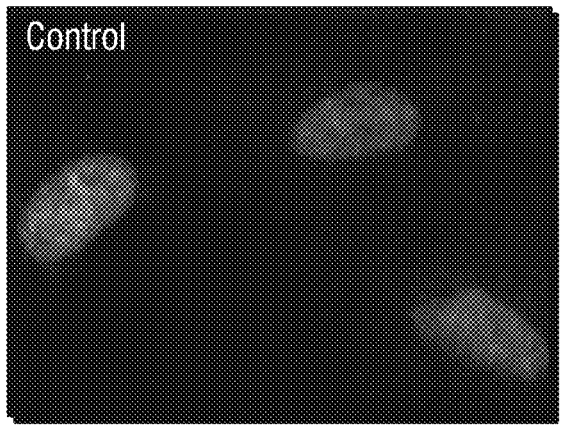
Figure 15B:
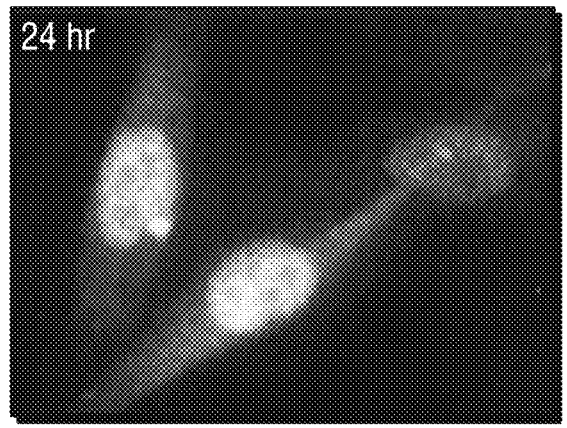
Figure 15C:
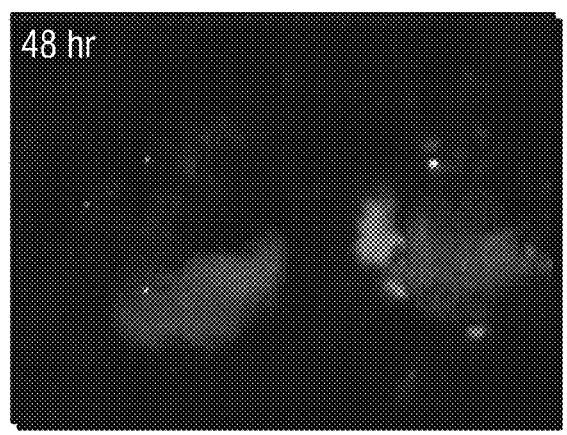
Figure 16A:
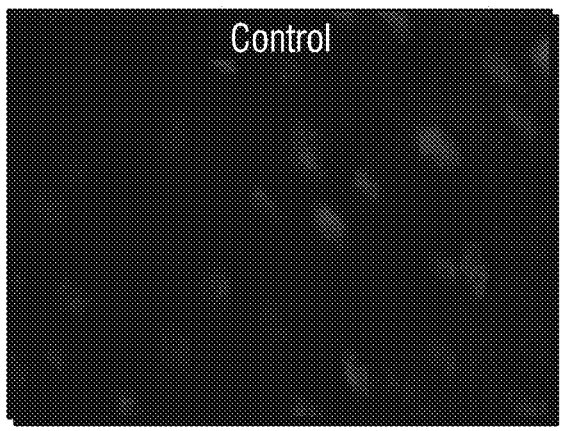
Figure 16B:
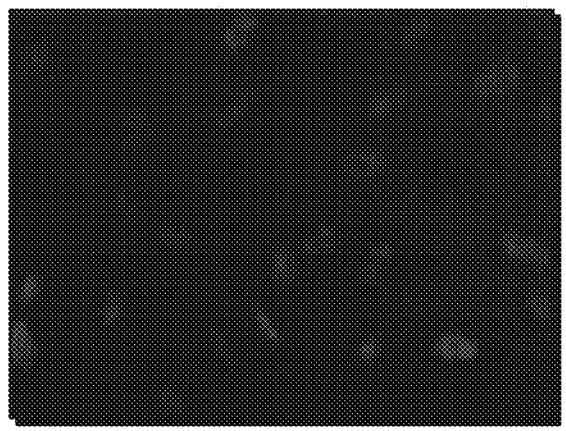
Figure 16C:
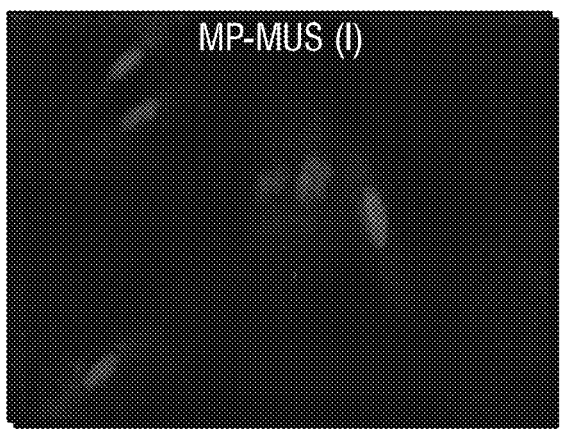
Figure 16D:
Figure 16E:
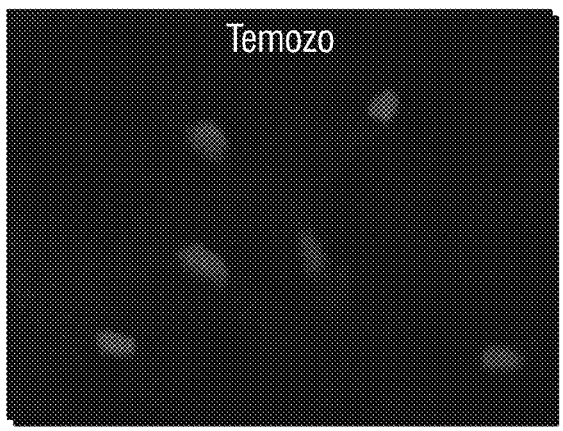
Figure 16F:
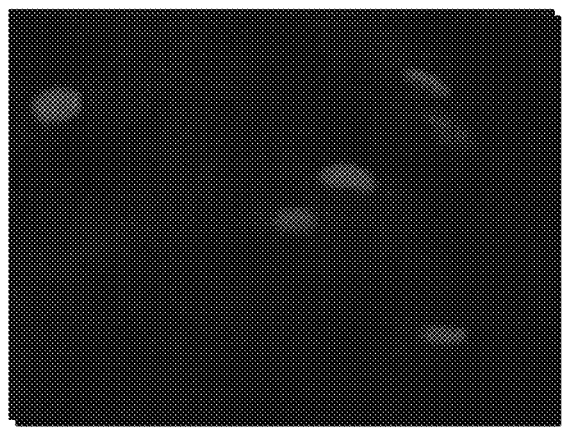
Figure 17A:
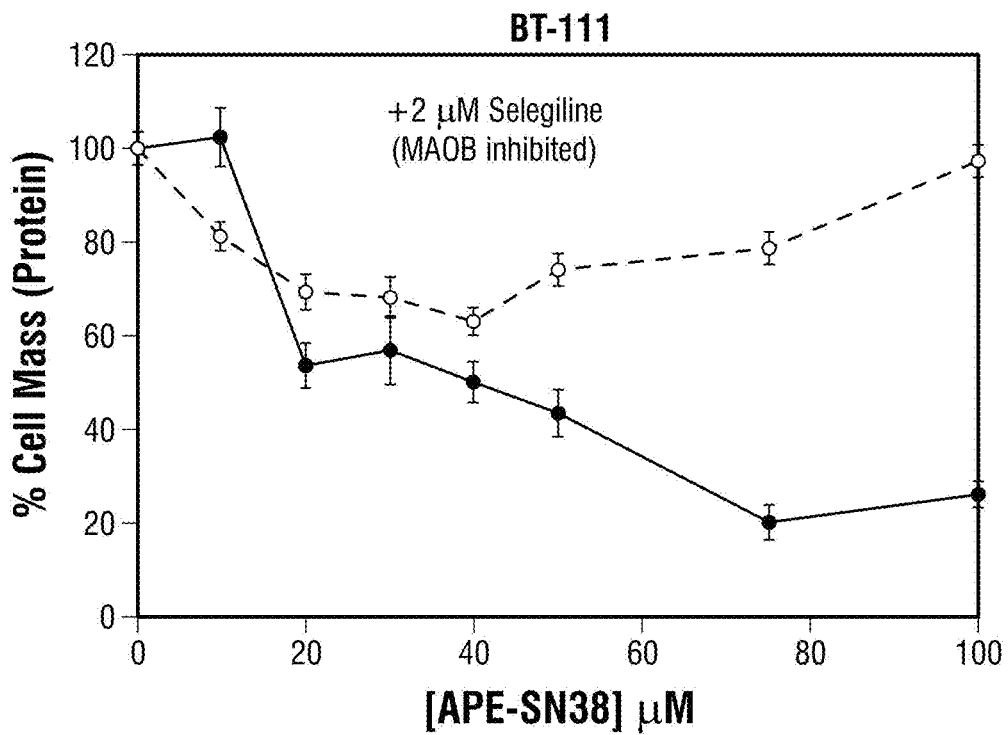
Figure 17B:
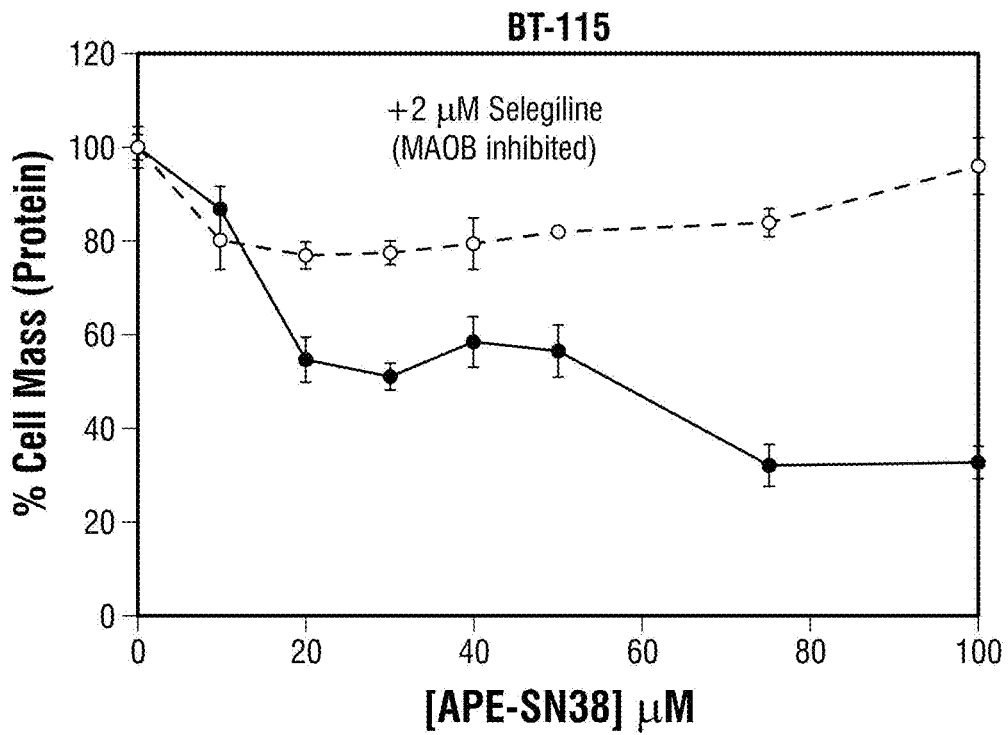
Figure 18A:
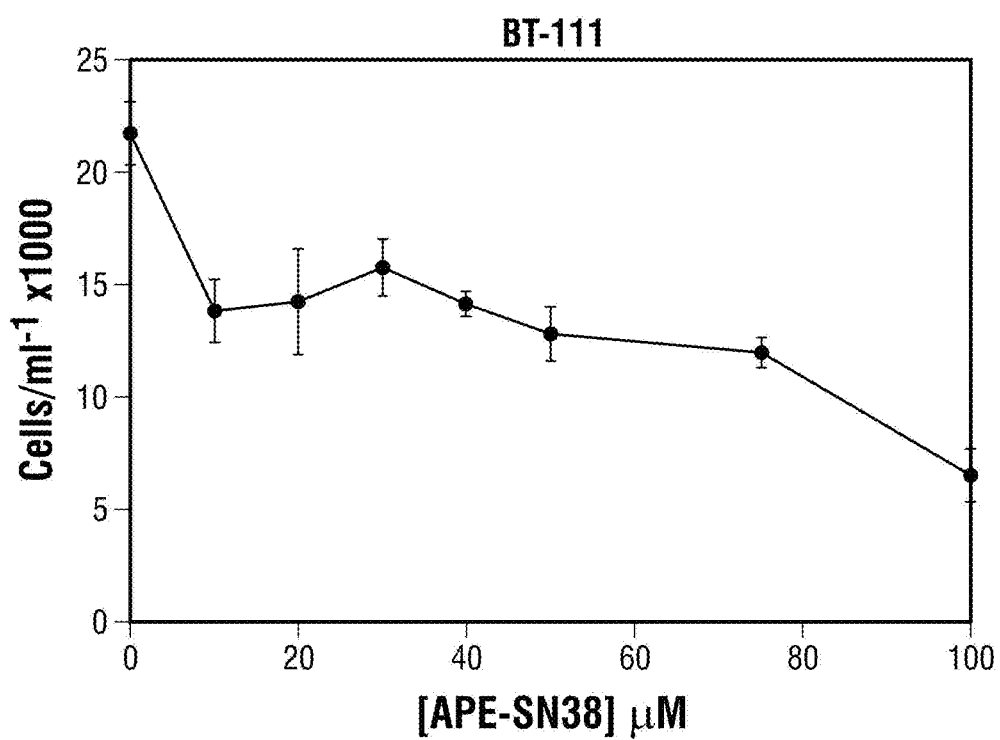
Figure 18B:
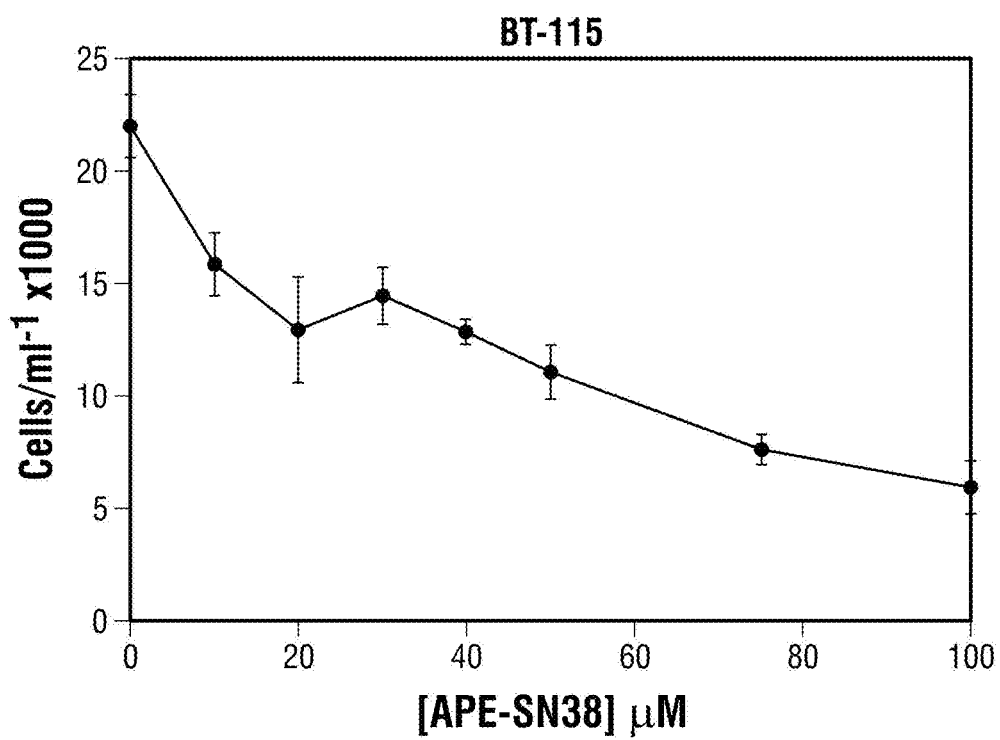
Figure 19:
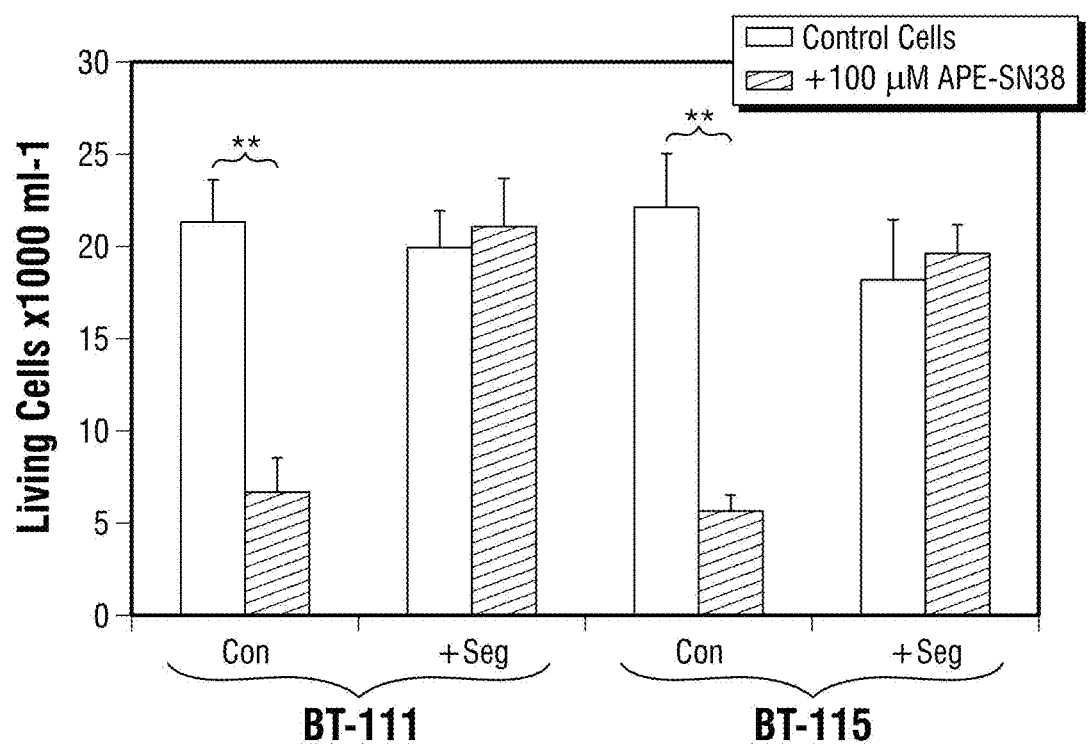
Figure 20A:
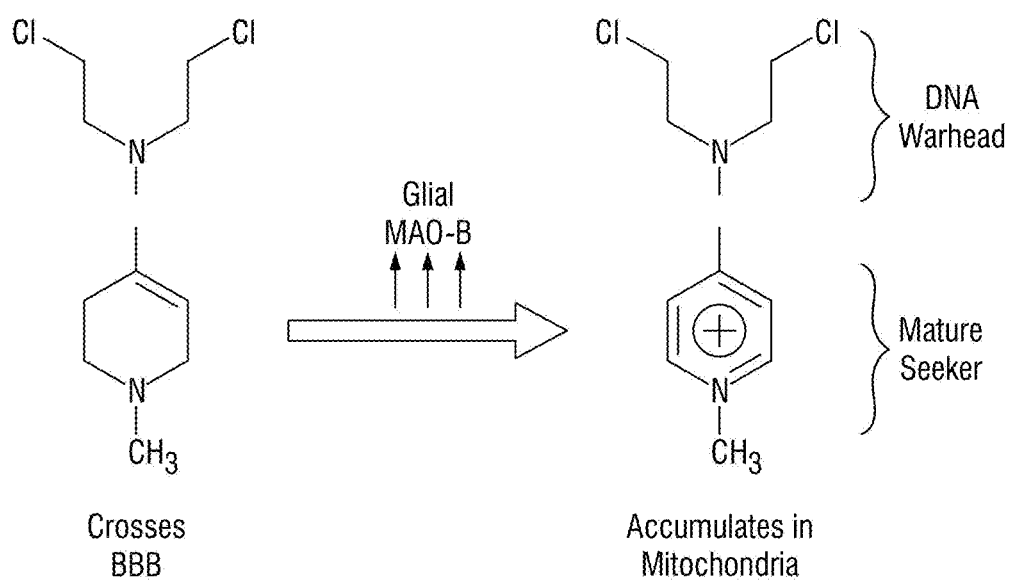
Figure 20B:
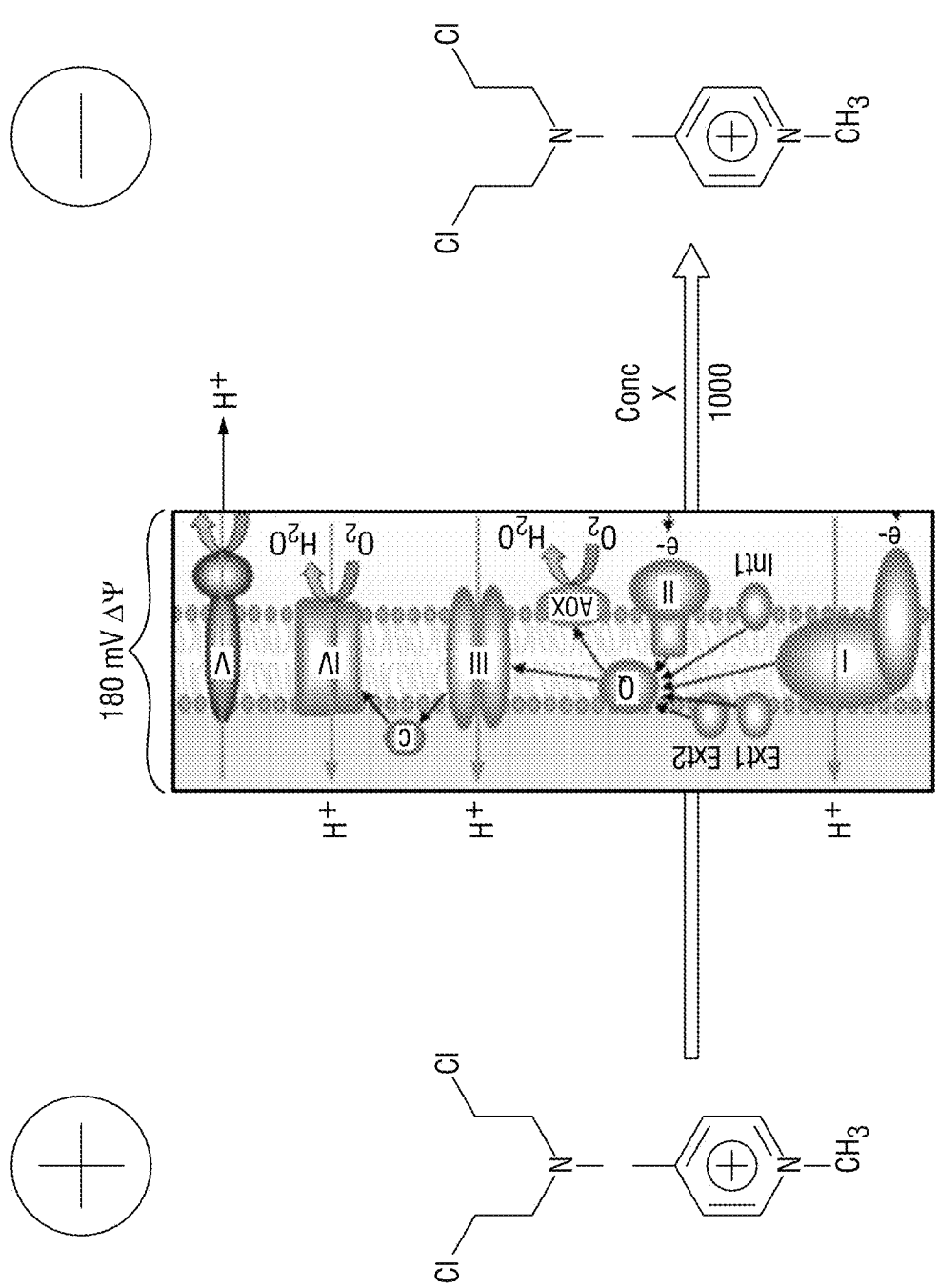
Figure 21:
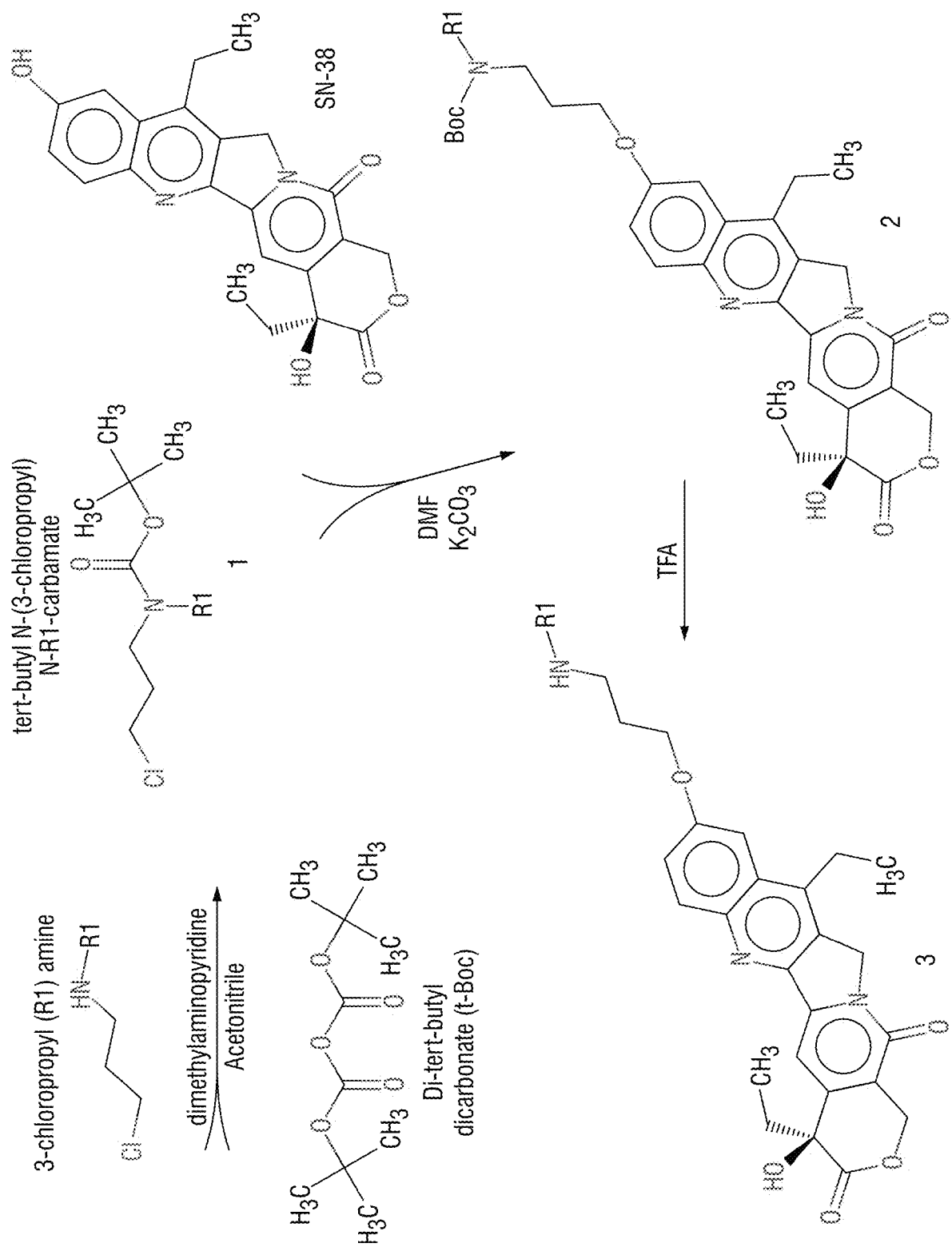
Figure 22:
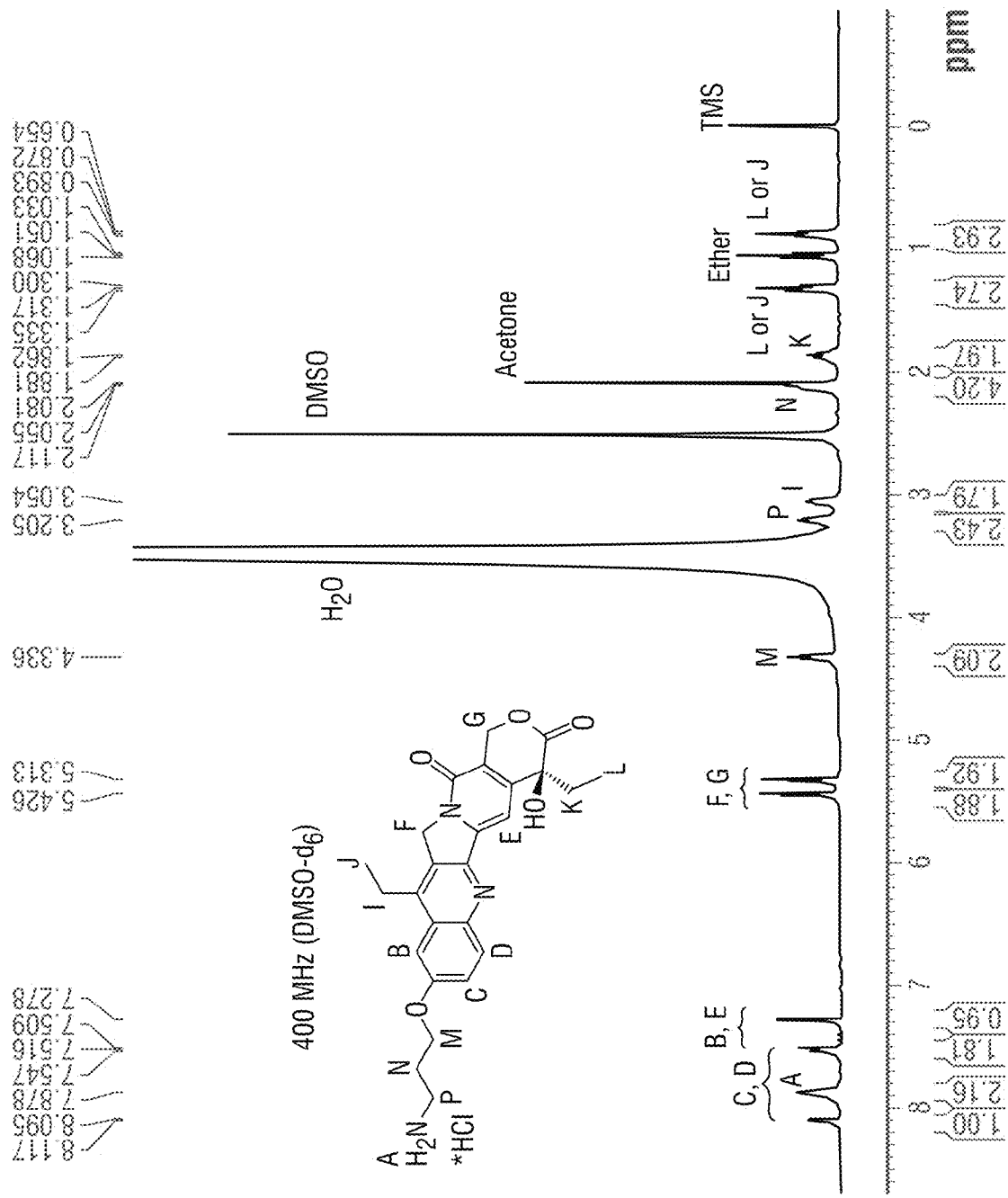
Figure 23:
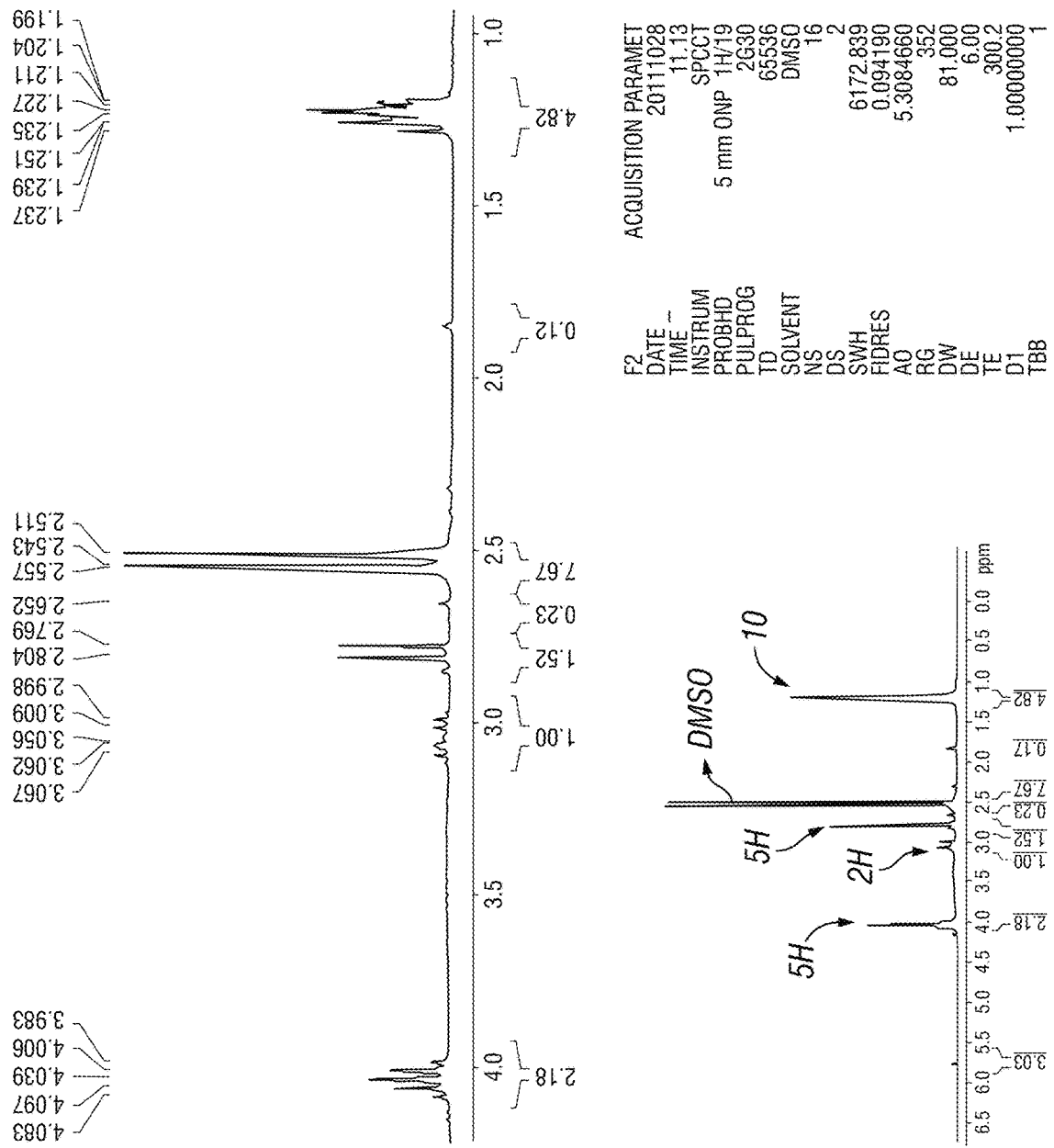
Figure 24:
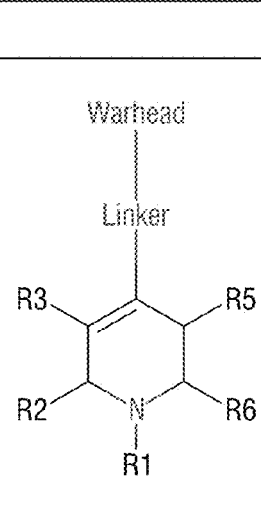
Figure 25:
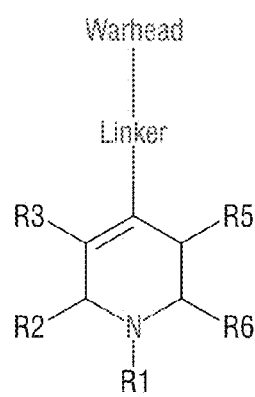
Figure 28A:
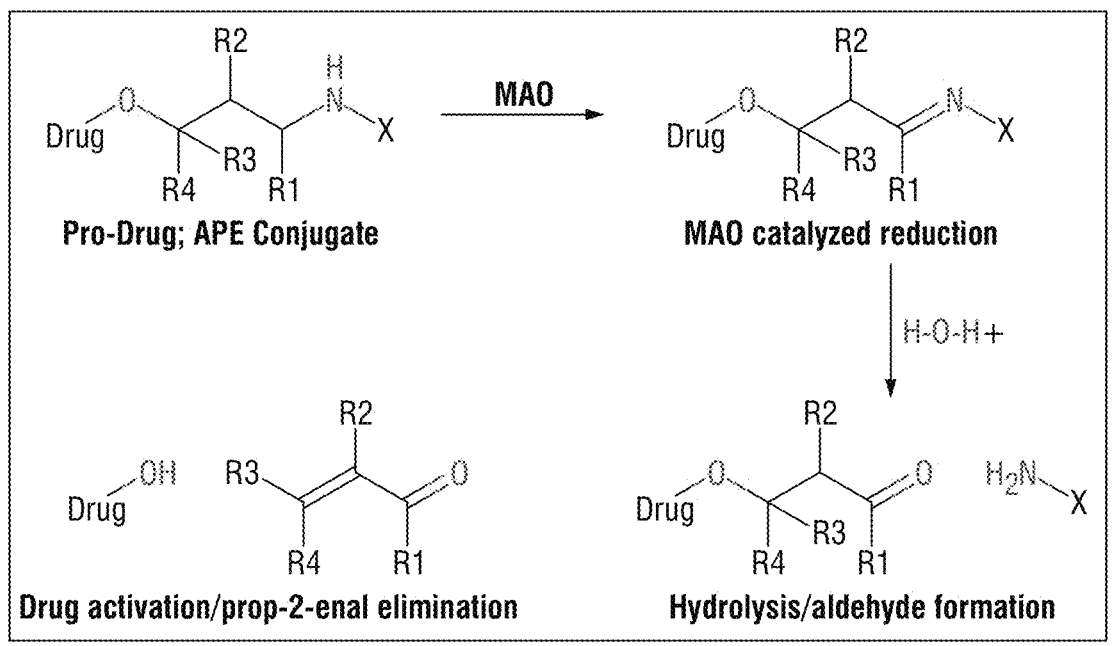
Figure 28B:
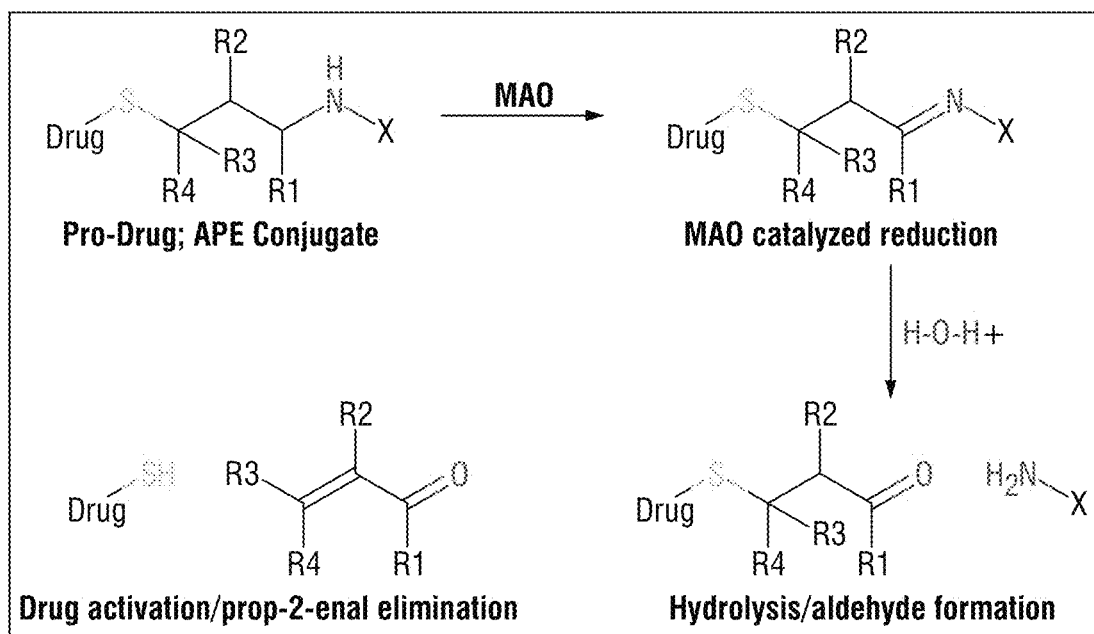
Figure 29A:
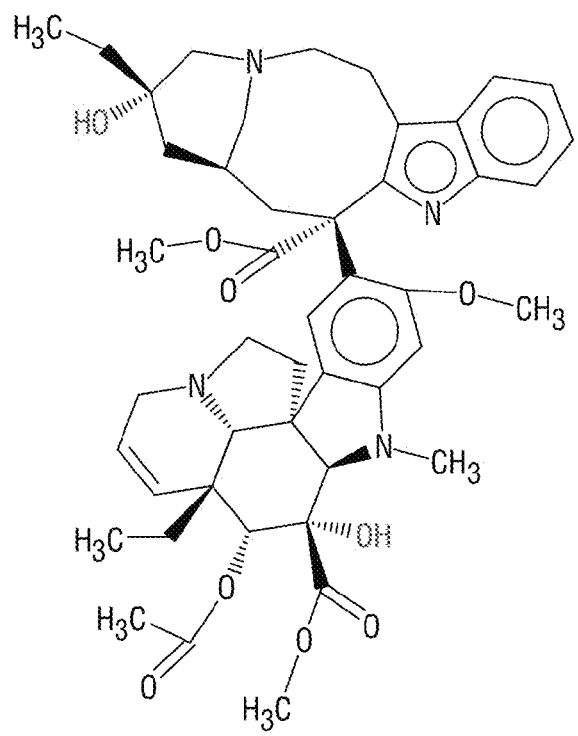
Figure 29B:
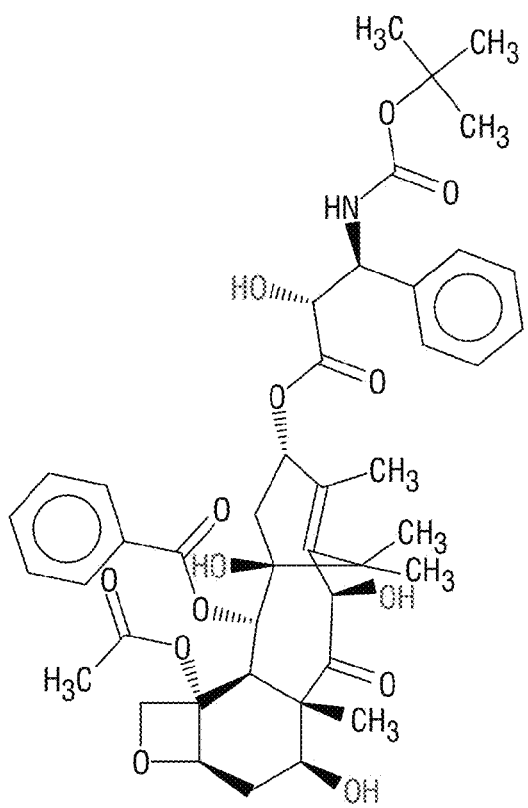
Figure 29C:
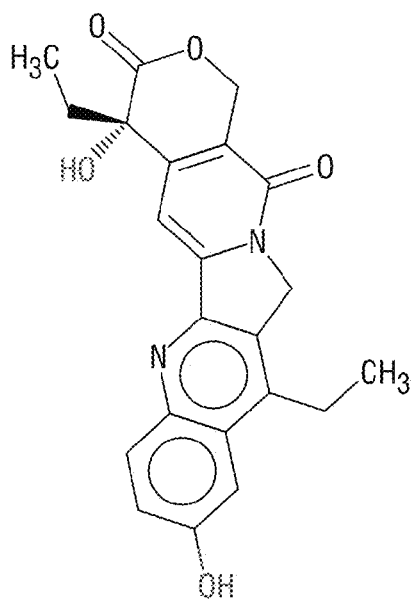
Figure 29D:
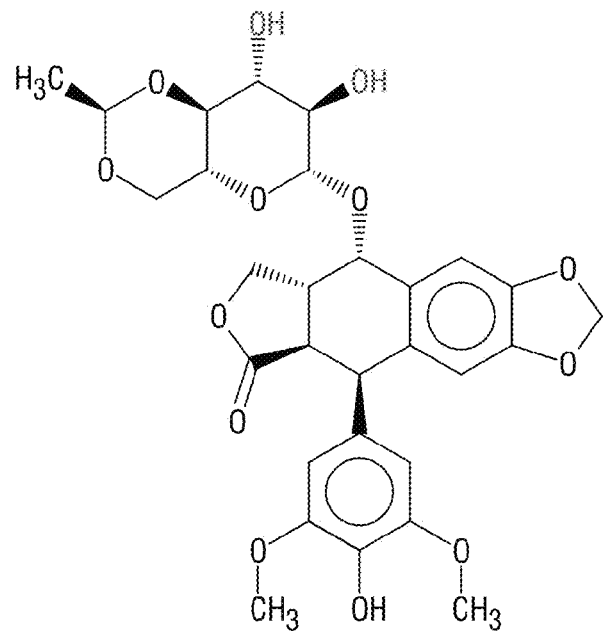
Figure 31A:
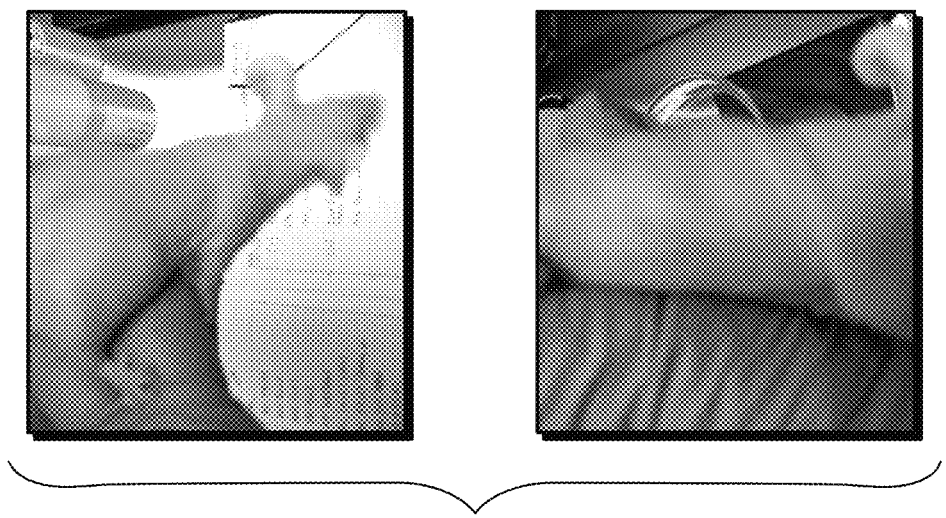
Figure 31B:
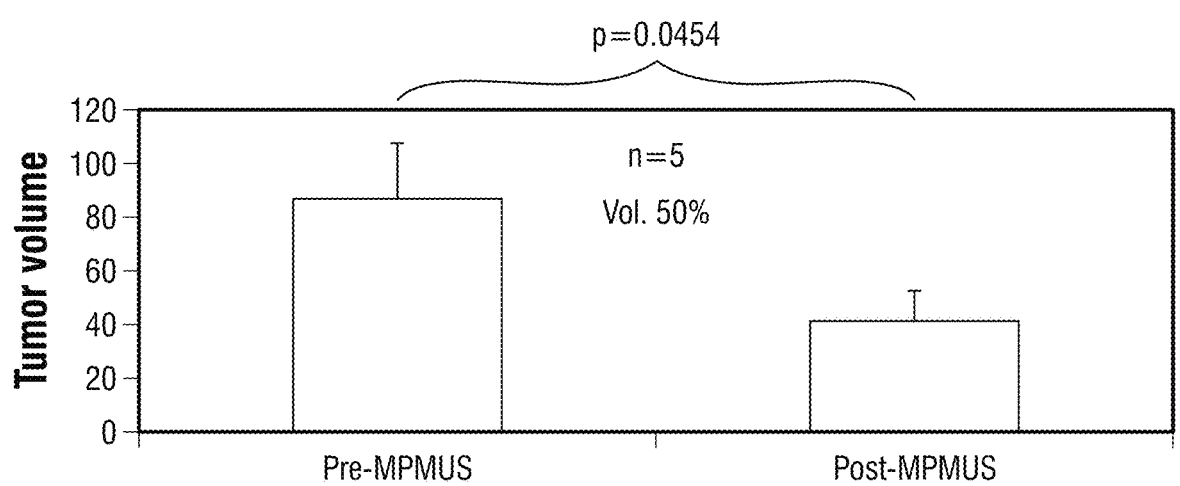
Figure 32:
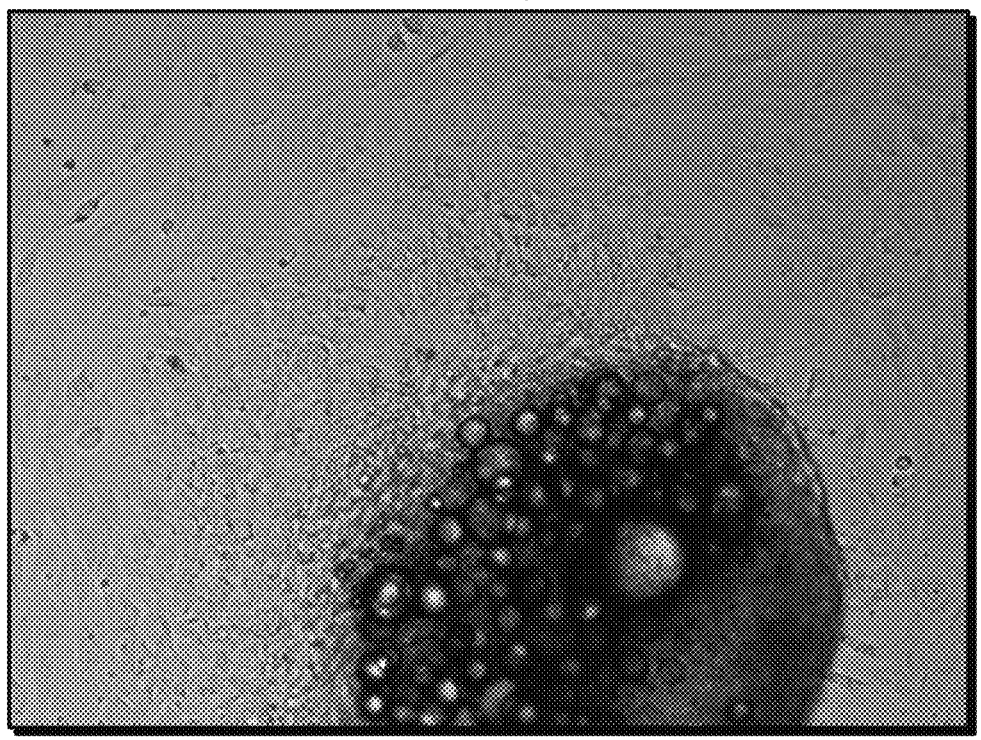
Figure 33A:
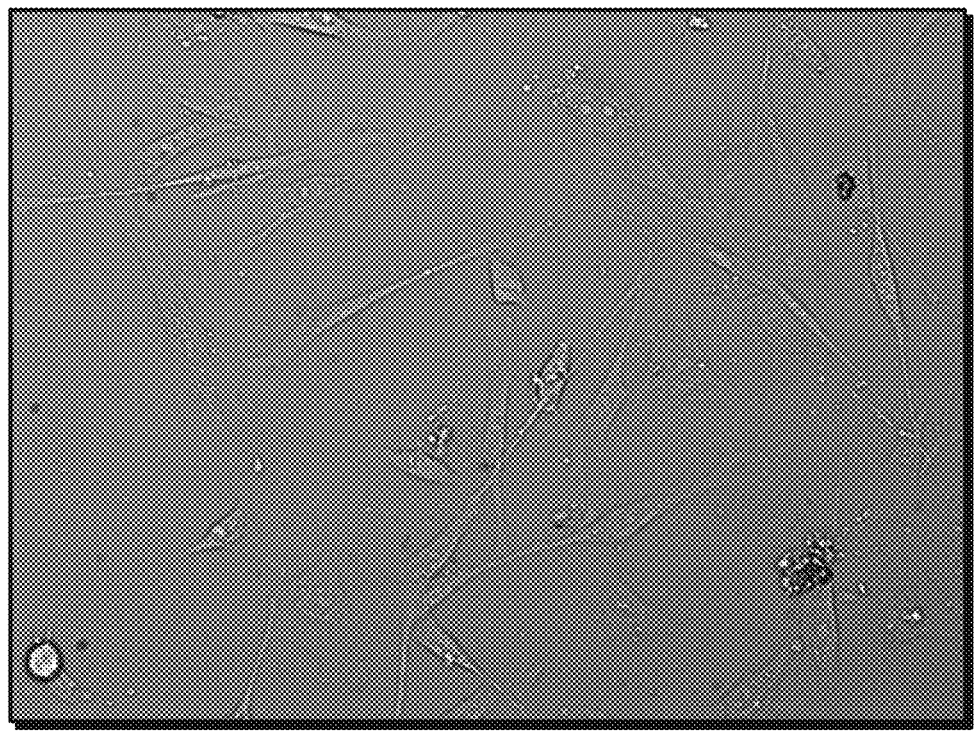
Figure 33B:
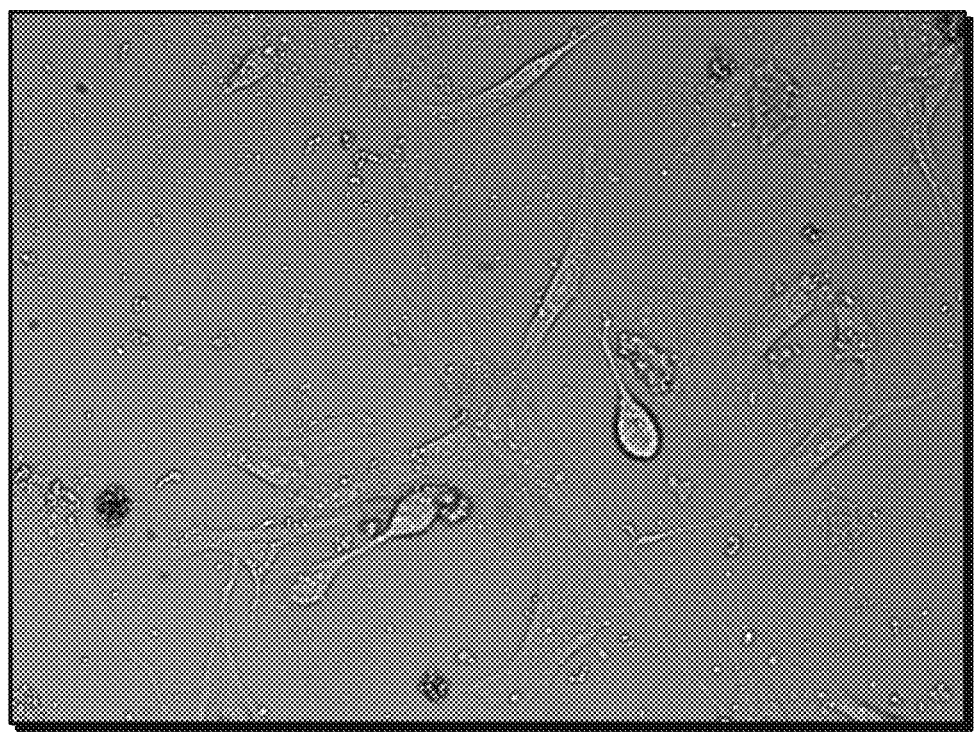
Figure 34:
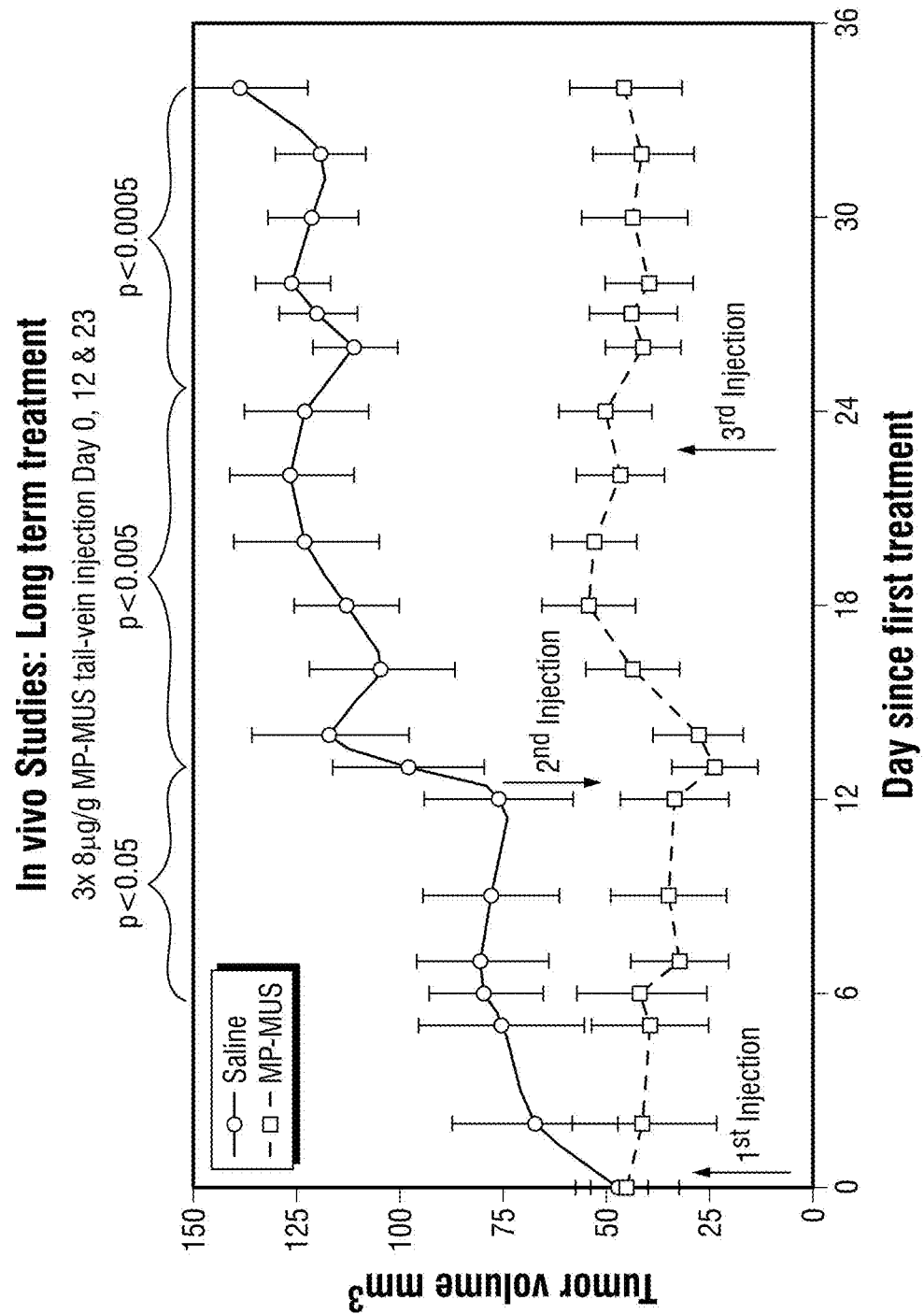
Figure 35:
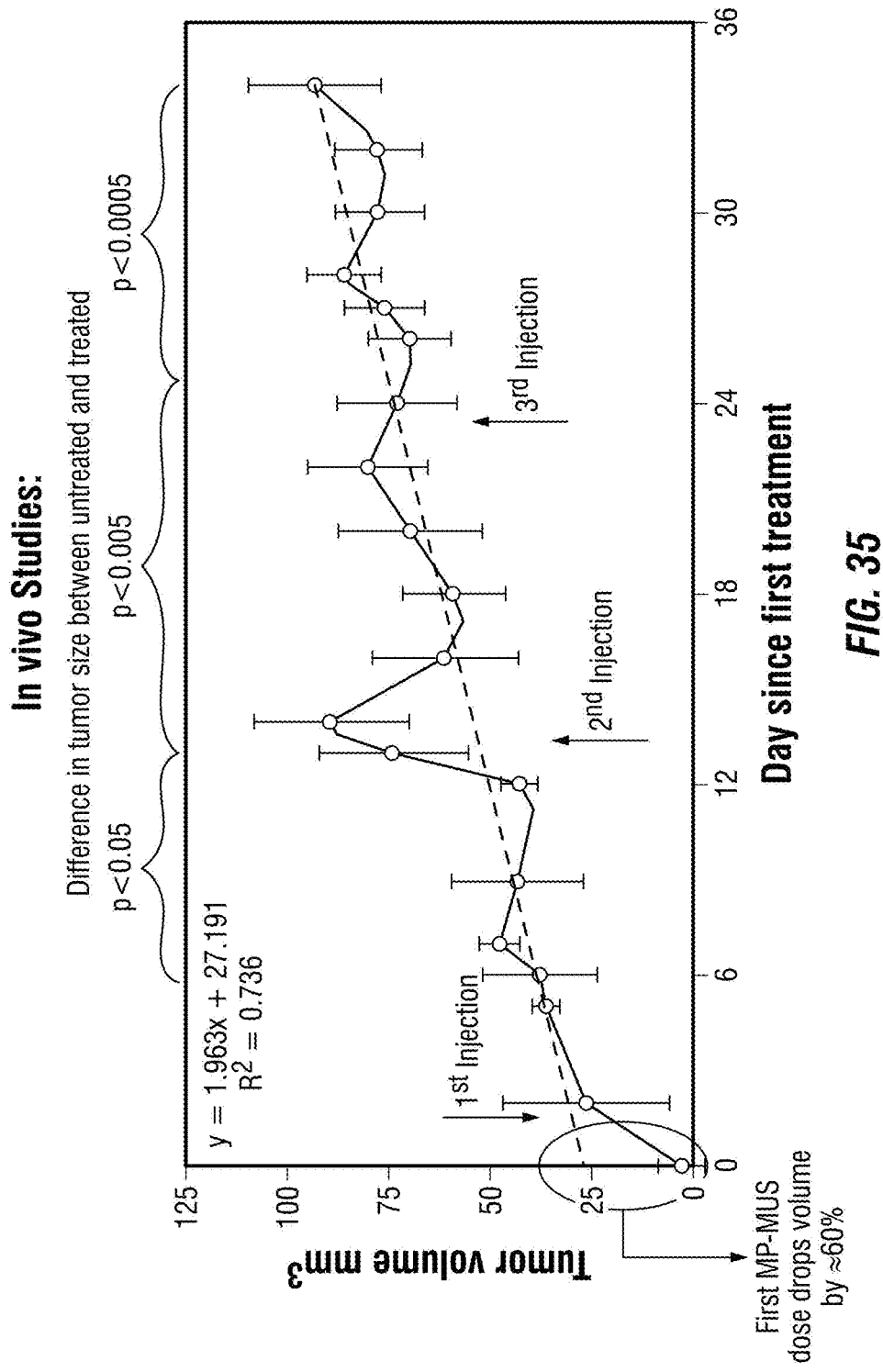
Figure 36:
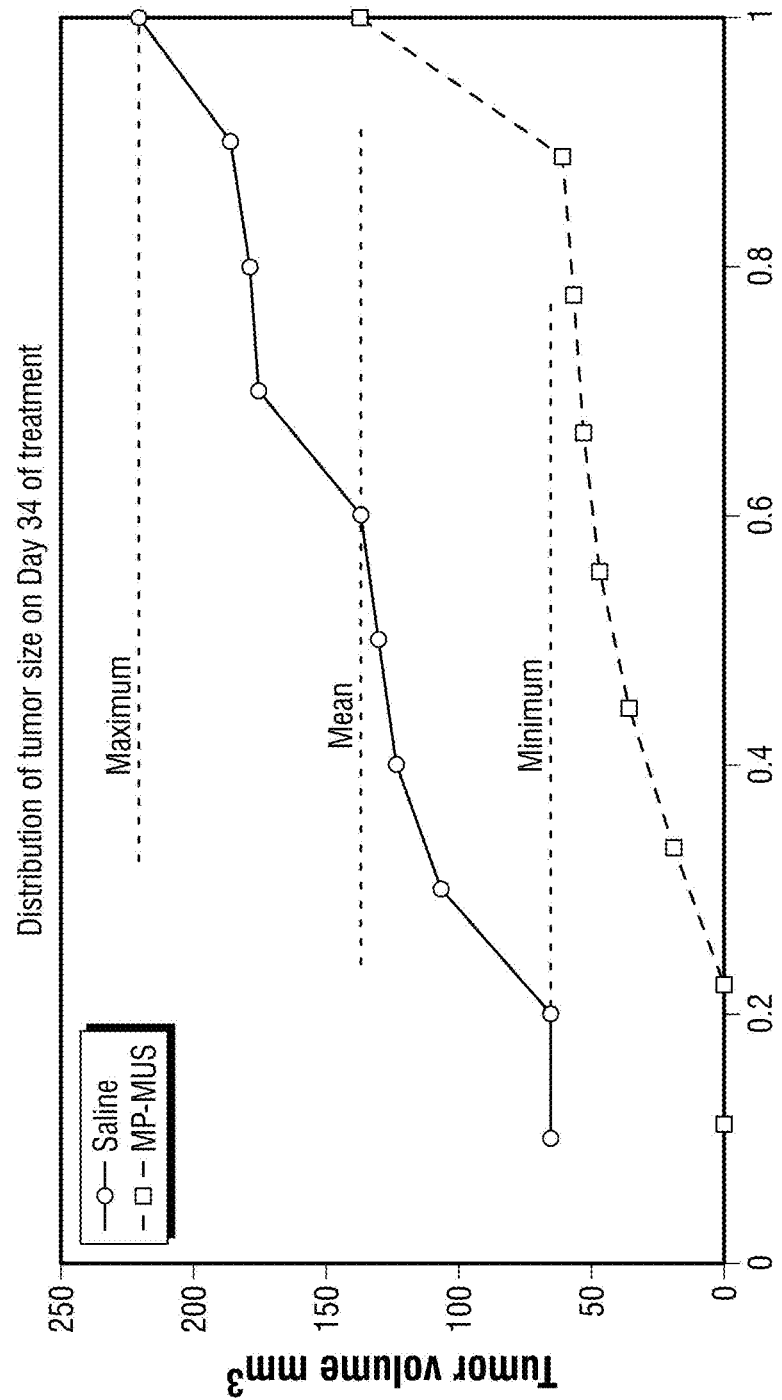
Figure 37:
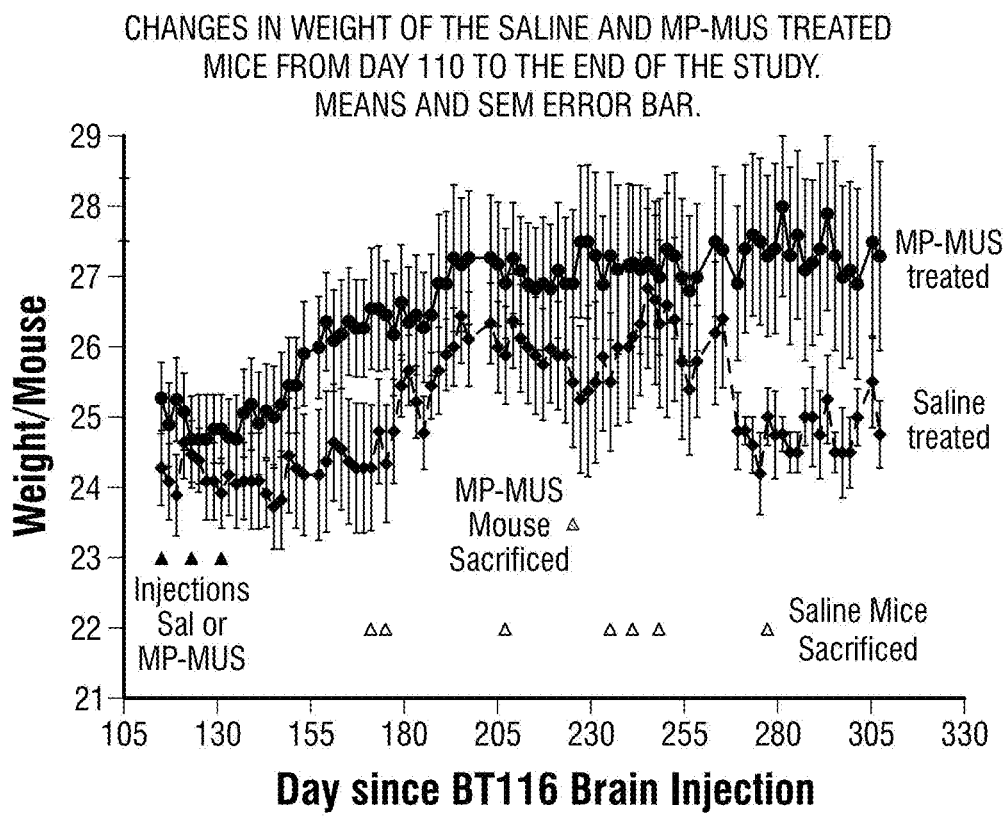
Figure 38:
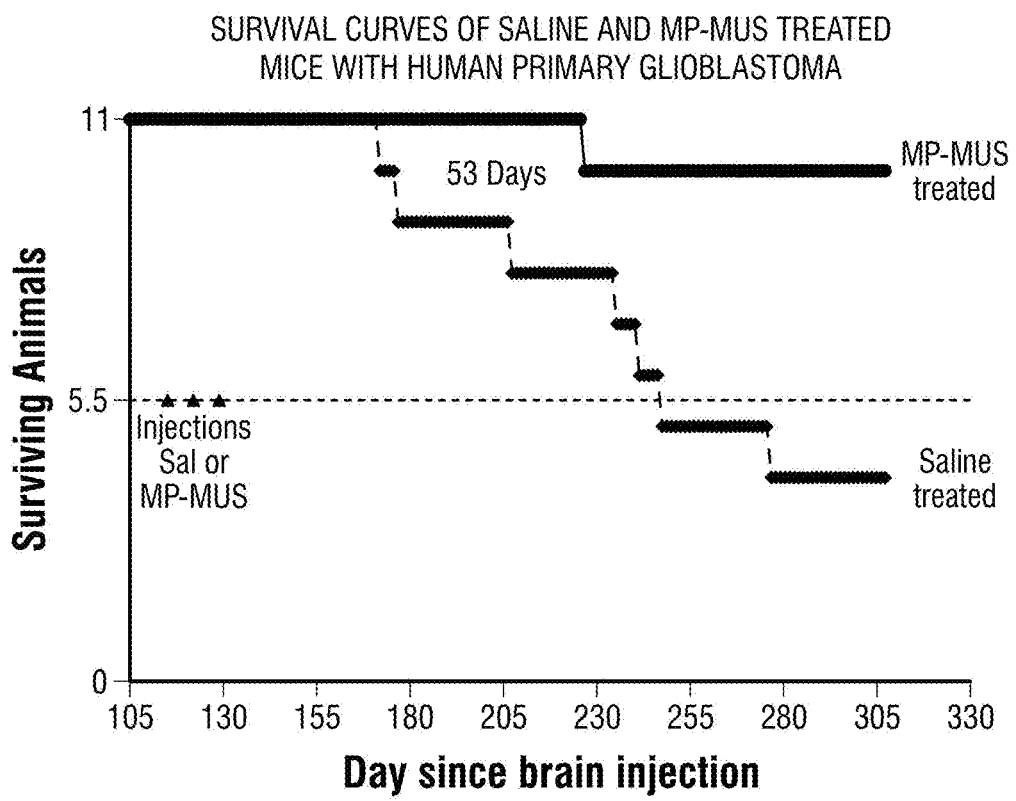
Figure 41A:
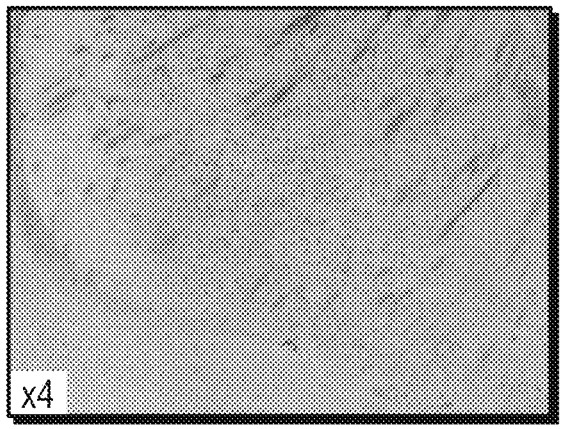
Figure 41B:
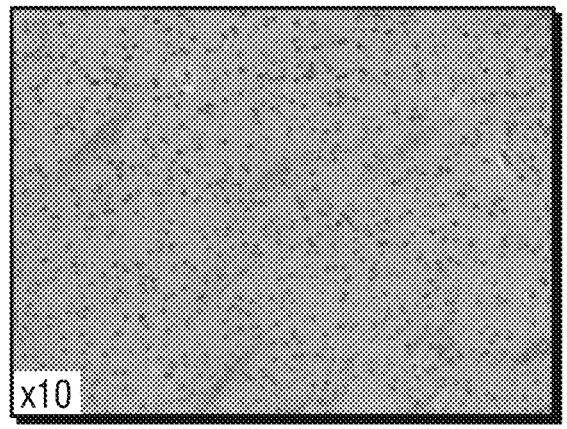
Figure 41C:
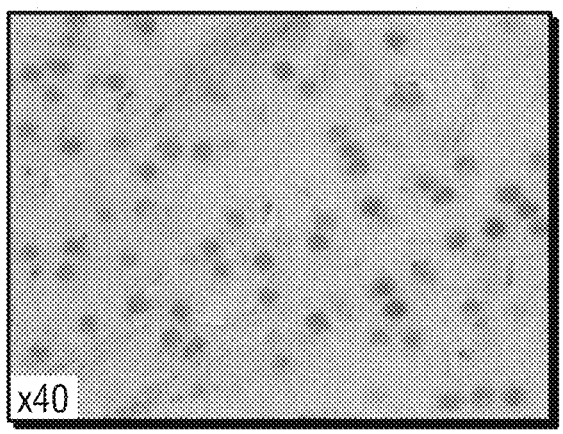
Figure 41D:
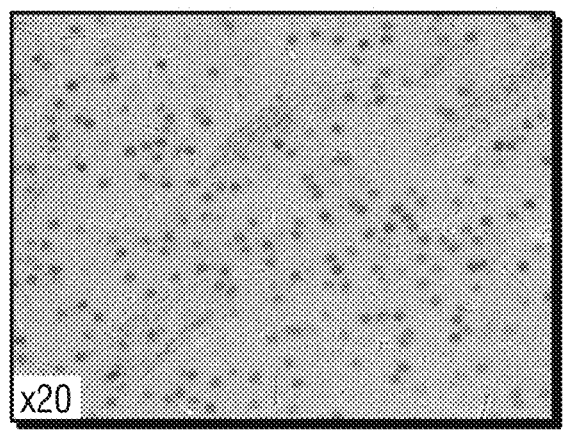
Figure 42A:
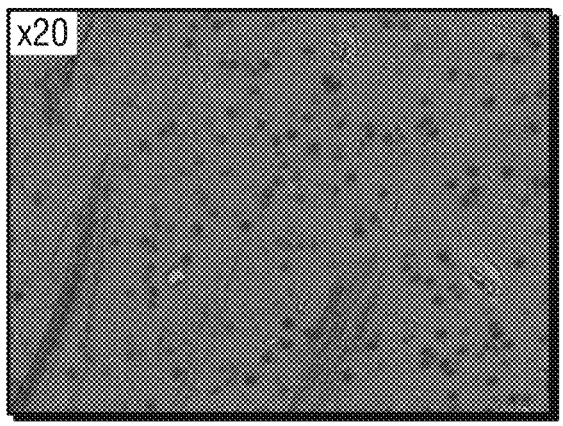
Figure 42B:
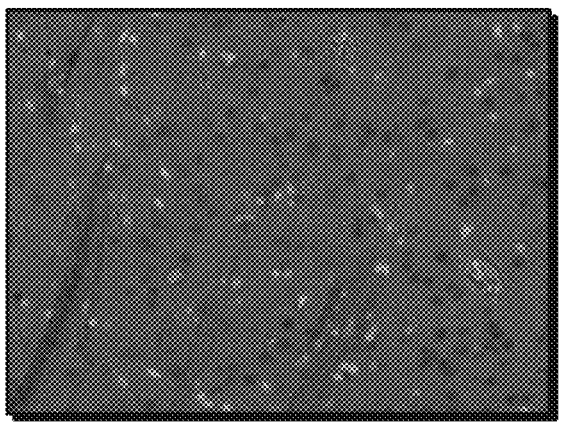
Figure 42C:
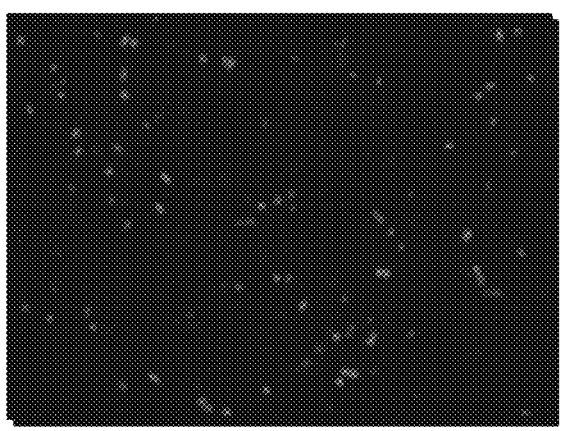
Figure 42D:
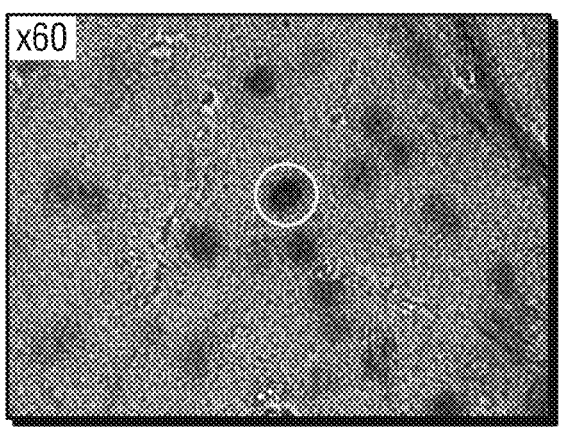
Figure 42E:
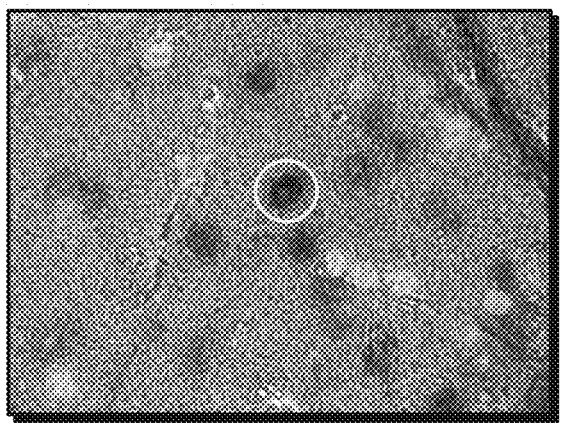
Figure 42F:
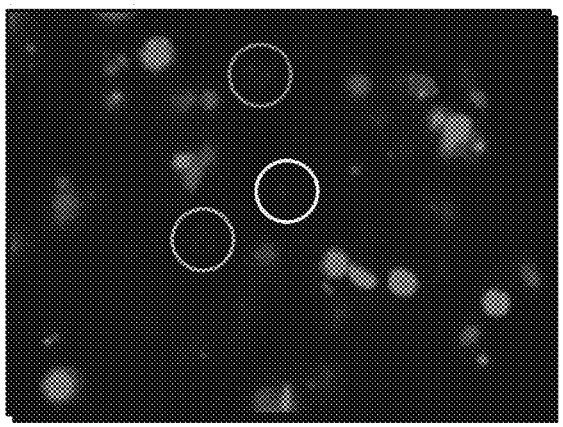
Figure 43A:
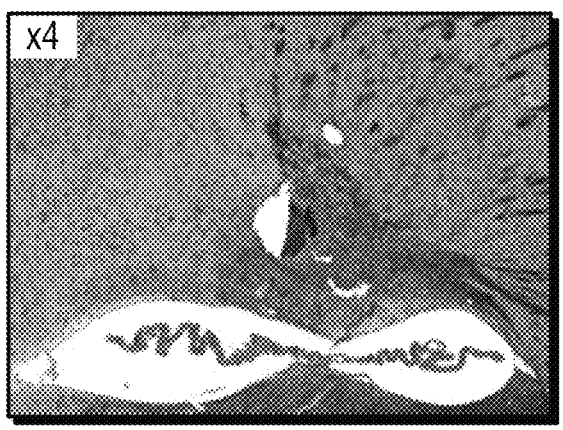
Figure 43B:
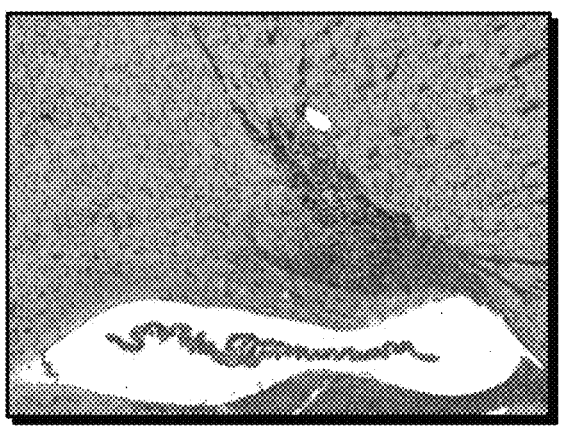
Figure 43C:
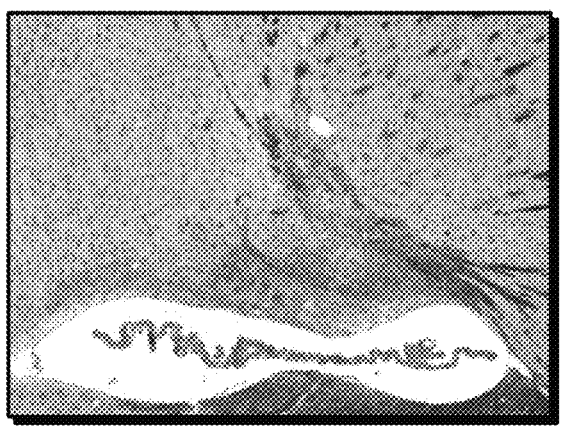
Figure 43D:
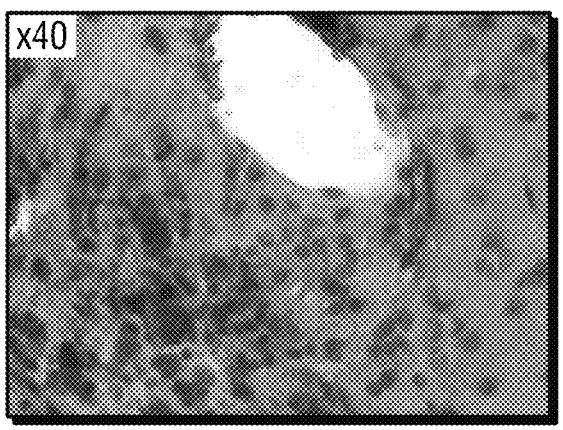
Figure 43E:
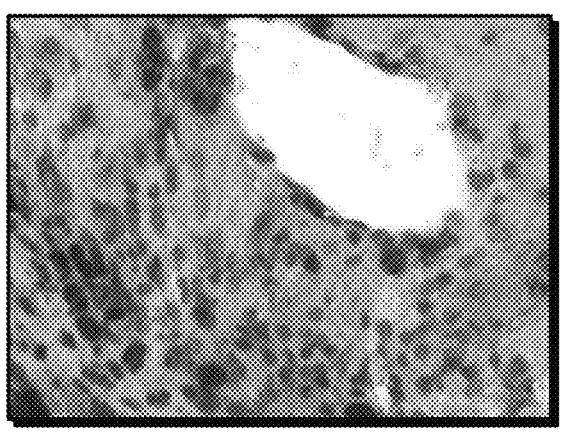
Figure 43F:
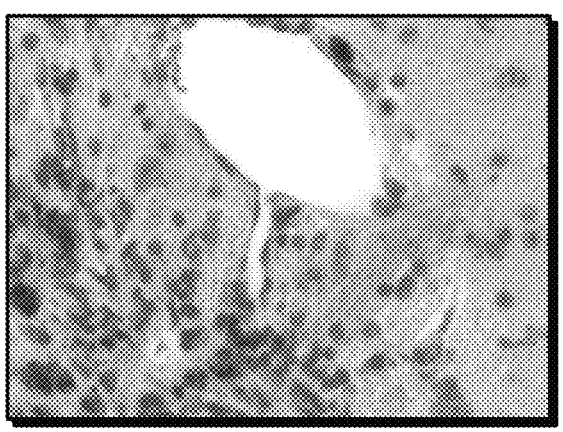
Figure 45A:
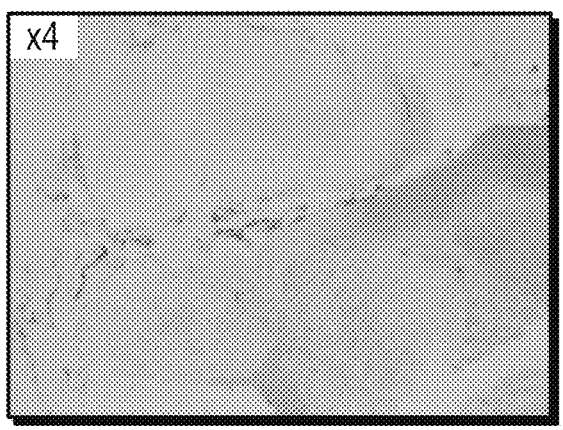
Figure 45B:
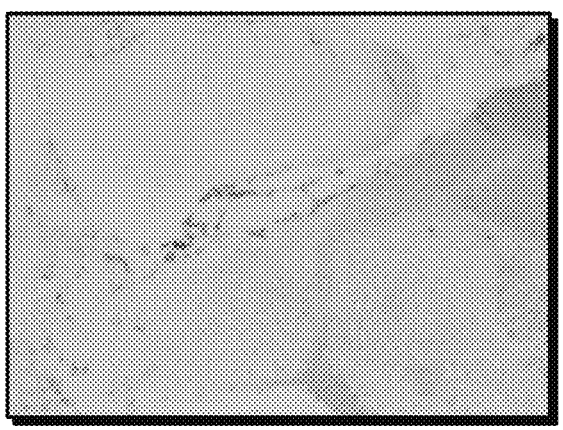
Figure 45C:
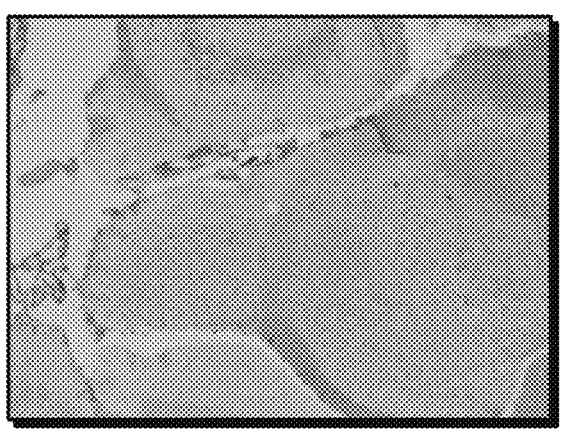
Figure 45D:
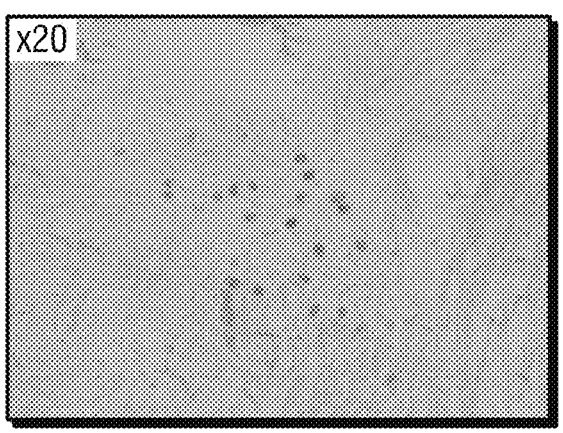
Figure 45E:
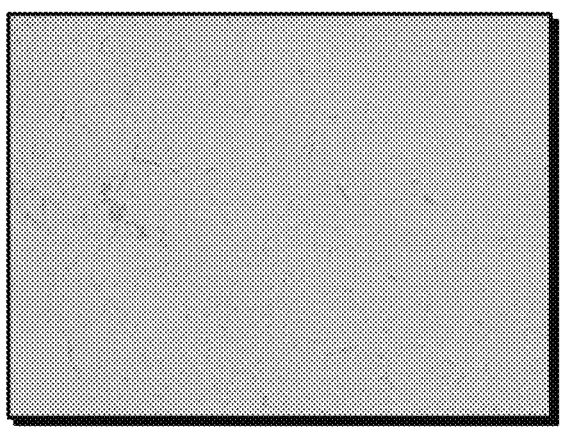
Figure 45F:
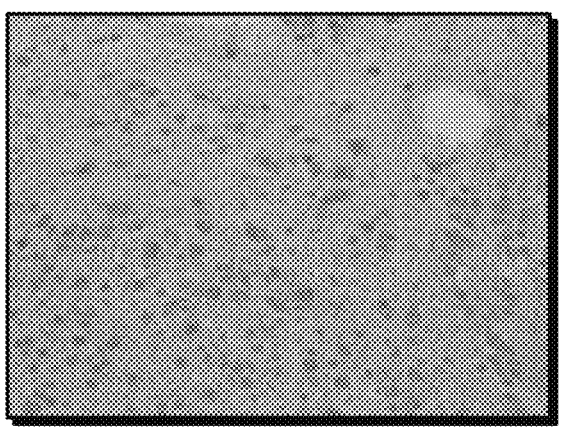
Figure 46A:
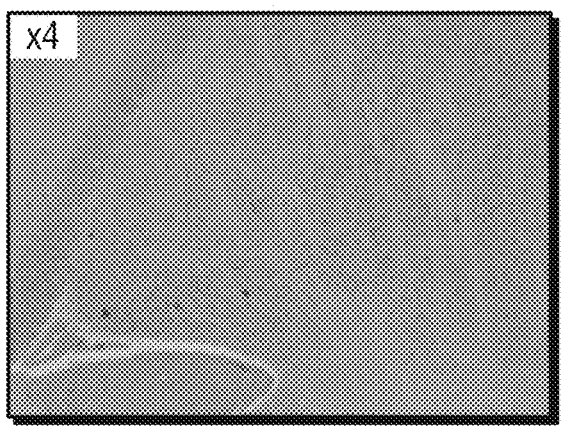
Figure 46B:
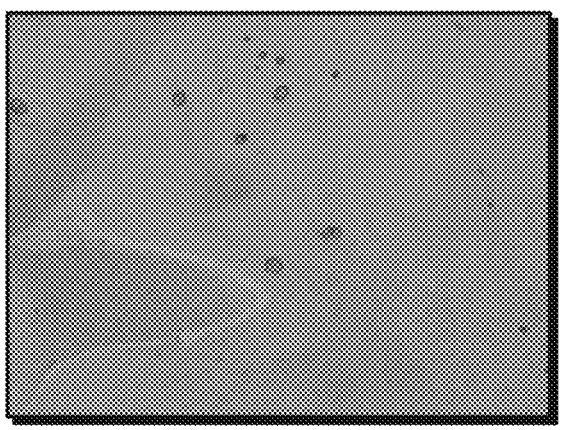
Figure 46C:
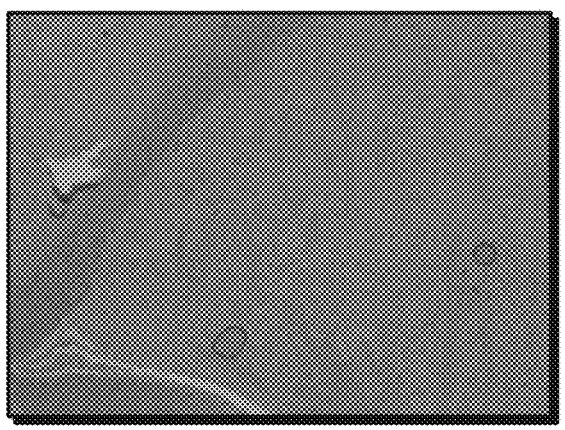
Figure 46D:
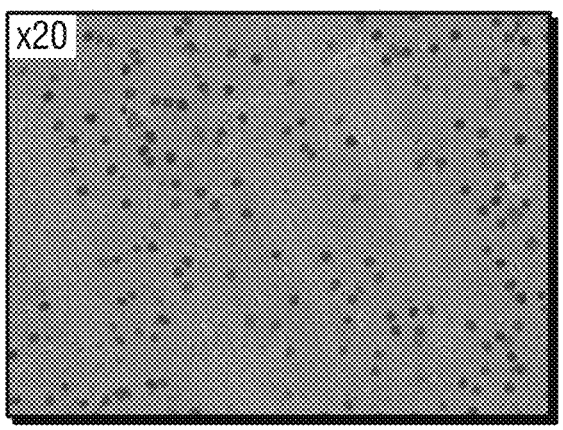
Figure 46E:
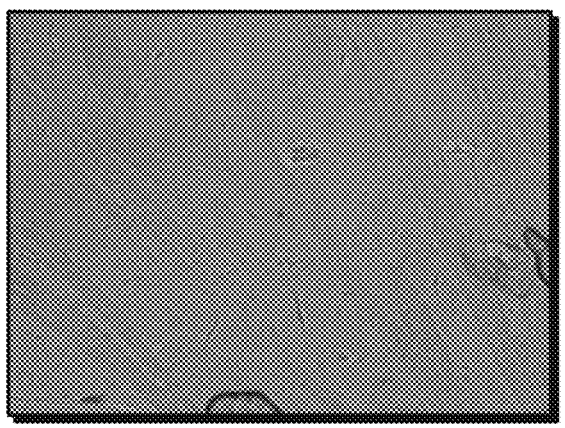
Figure 46F:
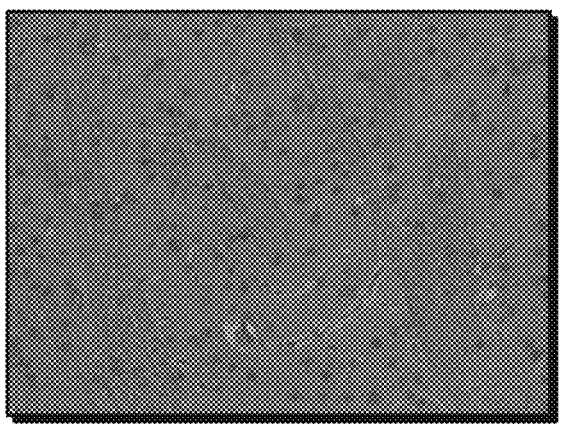

FIG. 3 illustrates the difference in the amino acid sequences of human MAO-A and MAO-B. The aligned amino acid sequence of human MAO-A is shown in red and MAO-B in blue. Residues which alter the specificity of the two enzymes with respect to substrates and inhibitors are shown underlined and highlighted in yellow. The linking 'handcuffs' show that amino acid pairs in the two structures occupy similar positions within the channels of the two enzymes. The loops that partly occlude access to the channels, 'A' F112-T130 and 'B' F103-T122, are outlined in gray. FIG. 2A and FIG. 2B show the in silico modeling of MAO substrate specificity. FIG. 2A I and II show the structures of 'perfect' substituted MPTP analogues that have high MAO-A I) or MAO-B II) specificity, with enzyme pocket contours. FIG. 2A shows MP-MUS (I) and FIG. 2B shows the compound when docked within the MAO-B pocket;

FIG. 4A, FIG. 4B, FIG. 4C, and FIG. 4D show the difference in the substrate channels of the two enzymes. The overlay of the know inhibitors of MAO-A and MAO-B informs one of the approximate size, shape and electrodensity of putative, rationally designed substrates that may serve as pro-Drugs with high MAO-B/MAO-A activities. In FIG. 4A, FIG. 4B, and FIG. 4C the spacing filling overlaid specific inhibitors are labeled red for MAO-A and blue or MAO-B, as are important residues that line the two substrate channels. FIG. 4A and FIG. 4B show that the entry of substrates into the reaction site (FAD) is different in the two enzymes, with two different channels. The 'A' channel is blocked by Y323 in MAO-B and the 'B' channel is blocked by F208 in MAO-A. Access to the 'B' channels is further restricted by F193 in the MAO-A structure. FIG. 4C shows an overlay of different restricting amino acids, with a space-filling overlay of the MAO-A inhibitor, clorgiline, and the MAO-B inhibitor LDAO. The base of channel of MAO-B is more hydrophobic, partially due to the presence of C172 and T314, whereas in the presence of residues N181/C323 increase hydrogen bonding and halogen interaction, in MAO-A. The final panel FIG. 4D shows the overlaid MAO-A- and MAO-B-specific inhibitor space fitting atoms, that fill the two channels; from three views;

FIG. 5 shows the inhibition constant ($K_i$ in µM) of MAO-A and MAO-B, and the inhibition ratio for a series of related pyrrols;

FIG. 6A and FIG. 6B show the fitting of two pyrrole-based inhibitors fitted into the 'A' (FIG. 6A) and 'B' (FIG. 6B) channels of the two enzymes. The overlay of these two MAO-specific inhibitors of MAO-A and MAO-B informs one of the size, shape and charge distributions of small molecules that fit preferentially into the reaction pocket of either MAO-A or MAO-B;

FIG. 7 illustrates the inhibitor structures and $K_i$ constants found in a study (see Fierro et al., 2007) performed on human recombinant MAO, looking at competitive inhibition using variations of a core phenylamine structure;

FIG. 8A and FIG. 8B show the fitting of two phenylamine-based inhibitors fitted into the 'A' (FIG. 8A) and 'B' (FIG. 8B) channels of the two enzymes. The overlay of these two MAO-specific inhibitors of MAO-A and MAO-B informs one of the size, shape and charge distributions of small molecules that fit preferentially into the reaction pocket of either MAO-A or MAO-B;

FIG. 9A, FIG. 9B, FIG. 9C, FIG. 9D, FIG. 9E, FIG. 9F, FIG. 9G, FIG. 9H, FIG. 9I, FIG. 9J, FIG. 9K, FIG. 9L and FIG. 9M illustrate the ability MAO-A/B to oxidize the primary or secondary amine of a propylamine ester to form an alcohol. The first twelve panels illustrate how seven different MAO-B inhibitors map the interior space of the MAO-B channel, and show the basic dimensions of linker moieties. FIG. 9M is a model of the size and volume of MAO-B substrate channel and pocket; which is approximately 20 Å in length, approximately 6 Å wide, and up to 3.5 Å thick;

FIG. 10 shows the MAO-catalyzed oxidation of resorufin-aminopropyl ether to resorufin;

FIG. 11A, FIG. 11B, FIG. 11C, FIG. 11D, FIG. 11E, FIG. 11F, FIG. 11G, and FIG. 11H show the published mechanism for cleavage of the ether bond between propylamine and the fluorophore resorufin (Albers et al., 2007) (FIG. 11A). In FIG. 11B the same chemistry is shown for the conversion of pro-Drug APE-SN38 into the active SN38 drug. A number of structural forms of propylamine can be used for the same reaction, the minimal form FIG. 11C, and five and six membered ring versions, FIG. 11D and FIG. 11E. FIG. 11F is included for the sake of completeness and shows how oxidation by MAO of a 1,2,3,6-tetrahydropyridine ring can also cleave a 4-oxy/4-thio or 4-amino linkages, as described previously in PCT Intl. Pat. Appl. Publ. No. WO 98/22110. Five membered pyrrol rings that utilize a vinyl ether (or thioether or amine) can also serve as MAO-B cleavable substrates, if denuded of α-hydrogens at the $C_2$-position. FIG. 11G and FIG. 11H show how 2,2-difluoro or 2,2-dimethyl-3-($R_2$)-oxy-1-($R_1$)-5H-pyrroles are converted into their ketones, being converted first to the pyrrol-1-ium by MAO, and then undergoing hydrolysis to generate the alcohol and ketone pairs;

FIG. 12 shows the MAO-catalyzed oxidation of resorufin-aminopropyl ether to resorufin;

FIG. 13A and FIG. 13B show the comparison of cellular toxicity of MP-MUS(I), temozolomide and parental mustard at 24 hrs. Shown are the effects of MP-MUS(I), temozolomide, and the parental nitrogen mustard on the growth of BT-111 cells, using two orthodox techniques (n=3, ±1 Std. Deviation). FIG. 13A shows LDH growth and FIG. 13B shows mitochondrial XTT reduction;

FIG. 14A, FIG. 14B, FIG. 14C, and FIG. 14D demonstrate that the mitochondrial membrane potential was reduced by more than a third in the presence of 12 µM MP MUS(I) for 24 hours. 90% of the signal was conserved when cells were co-incubated with the MAO-B inhibitor Segiline, implicating prodrug maturation as a likely targeting mechanism;

FIG. 15A, FIG. 15B and FIG. 15C demonstrate that MP-MUS(I) altered mitochondrial protein levels in glioma cells;

FIG. 16A, FIG. 16B, FIG. 16C, FIG. 16D, FIG. 16E and FIG. 16F show illustrative embodiments of the invention, and in particular, the measurement and quantitation of DNA breaks in BT-111 cells;

FIG. 17A and FIG. 17B show the % Cell protein in two cultures of primary GBM exposed to APE-SN38, in the absence and presence of 2 µM selegiline. Selegiline-treated cells, ○, were measured in three wells at each concentration, and cells treated with only APE-SN38, ●, were measured in six wells. Error bars are the SEM at each APE-SN38 concentration. Protein was measured using the BCA/SDS method [Bicinchoninic acid (BCA) Protein Assay Kit with 0.1% sodium dodecyl sulfate detergent (Cat #23235, Thermo Fisher Scientific, Inc., Rockford, Ill., USA)];

FIG. 18A and FIG. 18B show the % Cell protein in two cultures of primary GBM exposed to [APE-SN38], in the absence and presence of 2 µM selegiline. Selegiline-treated cells, ○, were measured in three wells at each concentration, and cells treated with only APE-SN38, ●, were measured in six wells. Error bars are the SEM at each APE-SN38 concentration. Protein was measured using the BCA/SDS method described in the legend of FIG. 17A and FIG. 17B;

FIG. 19 shows selegiline protected BT-111 and BT115 GBM cultures from cell death;

FIG. 20A and FIG. 20B show schematic representations of the conversion of MP-MUS to the active charged form, which crosses the mitochondrial membrane and the resulting 1000-fold concentration within the mitochondria;

FIG. 21 shows an illustrative schematic synthesis of APE-SN38;

FIG. 22 shows the nuclear magnetic resonance (nmr) spectrum for APE-SN38;

FIG. 23 shows the nmr spectrum for MP-MUS;

FIG. 24 shows an overview of an entire "family" of MP-MUS-based multicomponent compounds useful in the practice of the present invention;

FIG. 25 illustrates exemplary combination/permutational variants of MP-MUS multicomponent compounds including those with substitutions of the tetrahydropyridine ring, wherein $R_1$, $R_2$, $R_3$, $R_5$, and $R_6$ can include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, —$C(=O)O\ R_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$, and —$S(=O)_2OR_a$. In addition, each of the substituents listed above may be further substituted with one or more of the above substituents, such that the substituent comprises a substituted alky, substituted aryl, substituted arylalkyl, substituted heterocycle, or substituted heterocyclealkyl. $R_a$ and $R_b$ in this context may be the same or different and, independently, hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl;

FIG. 26A, FIG. 26B, FIG. 26C, FIG. 26D, FIG. 26E, FIG. 26F, FIG. 26G, FIG. 26H, FIG. 26I and FIG. 26J illustrate exemplary combination/permutational variants of the linkers in MP-MUS bifunctional compounds in accordance with one aspect of the present invention;

FIG. 27 illustrates an exemplary N-substituted 3-chloropropyl amine for conversion of drugs into MAO-sensitive pro-drugs in accordance with one aspect of the present invention. Essentially any conventional drug, which has an active alcohol or thiol can be converted into a pro-drug that can only become converted into the active drug form following the enzymatic action of MAO on the resulting ether or thioether. The size/hydrophobicity of the bottom of the substrate binding pockets of MAO-A and MAO-B will confer selectivity towards the substrates;

FIG. 28A and FIG. 28B show illustrative N-substituted 3 chloropropyl amines for use in the conversion of selected therapeutic compounds into MAO-sensitive pro-drugs suitable for use in the practice of the present invention. FIG. 28A shows illustrative alcohols, while FIG. 28B shows illustrative thiols; Substituents $R_1$, $R_2$ and $R_3$ include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$ and —$S(=O)_2OR_a$;

FIG. 29A, FIG. 29B, FIG. 29C and FIG. 29D show illustrative existing chemotherapeutic drugs that can be converted to MAO-sensitive pro-drugs in accordance with the methods of the present invention;

FIG. 30 shows MAO-A and MAO-B activity of various MPTP derivatives useful in the practice of the present invention with 9 different substituents at the 2'-position of phenyl ring of MPTP, and how the substitutions effect the kinetics of the two enzymes;

FIG. 31A and FIG. 31B show the effects of 24-hr MP-MUS treatment. A statistically-significant drop in tumor volume, about 50%, was observed;

FIG. 32 shows that the lumps are tumor. The lumps were extracted and minced, placed in cell culture media, one observes a little bit of the lump is full of GBM, which grow out of the lump onto the bottom of the cell culture well;

FIG. 33A and FIG. 33B show GBM from untreated and MP-MUS treated tumors. While the untreated cells appeared just like parental BT111, the MP-MUS-treated cells were in poor condition, as evidenced by a lot of cell debris (even though they had already been washed);

FIG. 34 shows the plot of tumor size in the treated and untreated mice, error bars are SEM. Statistical difference in on the top, first $p<0.05$, the $p<0.005$, and finally $p<0.0005$;

FIG. 35 show a different plot (untreated minus treated average) of the data. The shape of the curve suggests that the tumor shrunk by 60% after the first injection, then growth in MP-MUS cells was less than 50% the untreated rate;

FIG. 36 shows the distribution in tumor size in the two mouse populations. Two mice were cured, and all MP-MUS-treated mice were below the mean size of the untreated animals. 90% of the treated mice tumors are less that the smallest untreated tumor. The distribution of the untreated mice is Gaussian (i.e., normal), but the biggest one in the MP-MUS treated makes it non-Gaussian;

FIG. 37 is a chart of the changes in weight of the saline and MP-MUS treated mice from Day 110 to the end of the study. The mice from the two groups (n=11) were periodically weighed from the day of the first MP-MUS/Saline tail-vein injection, after being randomized on Day 100. The days on which animals had to be sacrificed are shown by the arrows. Statistical significance, allowing for the 0.7 gram difference between the two groups over the injection period, occurs at the $p<0.01$ level between Day 145 and 155, depending on manner of calculation;

FIG. 38 is a chart of the survival curves of Saline and MP-MUS treated mice with human primary glioblastoma. The mice from the two n=11 groups were periodically and were sacrificed when they had severe neurological symptoms or suffered very rapid weight loss. 50% of Saline treated animals died before Day 250, whereas only one animal in the MP-MUS treated group died;

FIG. 39 is an illustration of the methodology for the unambiguous demonstration of human cancer cells in SCID mouse brain. †Note bald patches on 4 Saline treated mice, arrowed, compared with the well groomed MP-MUS treated mice. *The Human Vimentin epitope that is recognized by the mouse V9 antibody is labile with respect to peroxide. We used the mildest conditions that would remove the majority of endogenous and added peroxidase activity, but not destroy the human vimentin. For Vector Mouse Anti-Vimentin clone V9 and Santa Cruz Mouse anti-EGFR clone 528 the procedure was performed as shown. For CD3-ε, an extra step was used. CD3-ε was bound using an Arminian Hamster anti-CD3 epsilon antibody [145-2C11] conjugated with FITC, at a 1:10 dilution, for 1 hour. This was developed using a mouse anti-FITC antibody, Sigma clone FL-D6, at 1:100 dilution, for 1 hour. *Either a HRP-linked horse anti-Mouse antibody to develop DAB or the HiDef™ HRP-polymer system was used, the latter of which gave better signal-to-noise ratio, but has a disadvantage of detecting some levels of endogenous IgG in SCID mice;

FIG. 40A, FIG. 40B, and FIG. 40C show the unambiguous demonstration of human cancer cells in Saline #7 treated SCID mouse brain; left (non-injected) hemisphere ×4 Magnification. Saline #7 survived until the end of the trial at Day 307;

FIG. 41A, FIG. 41B, FIG. 41C, and FIG. 41D are four images from the study showing unambiguous demonstration of human cancer cells in Saline #7 treated SCID mouse brain; left (non-injected) hemisphere, of anti-(human) Vimentin labeling of the Saline #7 mouse brain at four different magnifications, showing single cell infiltration into the frontal brain, having entered from the right hemisphere via the corpus collusum; Infiltration of human primary glioma from right hand side injection site to left hemisphere. Glioma labeled using anti-vimentin (V9) and visualized using DAB;

FIG. 42A, FIG. 42B, FIG. 42C, FIG. 42D, FIG. 42E, FIG. 42F, FIG. 42G, FIG. 42H, FIG. 42I, FIG. 42J, FIG. 42K, and FIG. 42L show the unambiguous demonstration of human cancer cells in Saline #9 treated SCID mouse brain; left (non-injected) hemisphere; DAPI nuclear staining was co-localized with DAB staining of both antigens. The levels of DAPI fluorescence were attenuated by the presence of DAB-precipitate and so the nuclei gave a much poorer DAPI signal than did the nuclei of unlabeled cells. The arrows and circles indicate the colocalization of DAB staining and DAPI nuclear fluorescence. It is evident that there are bright nuclei, where there is no DAB staining, but the labeling with vimentin and with CD3-ε, shows cells with nuclei;

FIG. 43A, FIG. 43B, FIG. 43C, FIG. 43D, FIG. 43E, and FIG. 43F illustrate that a high level of Vimentin positive cells and CD3-ε cells are co-localized near the gliomal injection site. The Hematoxylin labels nucli blue and a high cell density are apparent in all images. Human derived cells and cells of the mouse immune system are mingled. Only a fraction of the gliomal cells were positive for the tyrosine kinase receptor, epidermal growth factor receptor (EGFR) and these are found farthest from the blood vessel;

FIG. 44A, FIG. 44B, FIG. 44C, FIG. 44D is tissue histology that shows Human cancer cells in Saline #4 treated SCID mouse brain; Right hemisphere injection point. Nuclei labeled with Hematoxylin; Slides 14 and 17 are 3×5 μm apart and underwent the same labeling procedure except for omission of primary antibody. Here the brain was sectioned sagittally, rather than axially, but labeling of Vimentin was present in tissue that is both cancerous and apparently necrotic;

FIG. 45A, FIG. 45B, FIG. 45C, FIG. 45D, FIG. 45E, and FIG. 45F is tissue histology that show Possible human cancer cells in MP-MUS #1 mouse brain; Right hemisphere; and FIG. 46A, FIG. 46B, FIG. 46C, FIG. 46D, FIG. 46E, and FIG. 46F is tissue histology that show possible human cancer cells in MP-MUS #1 mouse brain; Right hemisphere.

DESCRIPTION OF AMINO ACID SEQUENCES

```
SEQ ID NO: 1 is the amino acid sequence of the
human MAO-B polypeptide:
MSNKCDVVVVGGGISGMAAAKLLHDSGLNVVVLEARDRVGGRTYTLRNQK

VKYVDLGGSYVGPTQNRILRLAKELGLETYKVNEVERLIHHVKGKSYPFR

GPFPPVWNPITYLDHNNFWRTMDDMGREIPSDAPWKAPLAEEWDNMTMKE

LLDKLCWTESAKQLATLFVNLCVTAETHEVSALWFLWYVKQCGTTRIIST

TNGGQERKFVGGSGQVSERIMDLLGDRVKLERPVIYIDQTRENVLVETLN

HEMYEAKYVISAIPPTLGMKIHFNPPLPMMRNQMITRVPLGSVIKCIVYY

KEPFWRKKDYCGTMIIDGEEAPVAYTLDDTKPEGNYAAIMGFILAHKARK

LARLTKEERLKKLCELYAKVLGSLEALEPVHYEEKNWCEEQYSGGCYTTY
```

-continued

```
FPPGILTQYGRVLRQPVDRIYFAGTETATHWSGYMEGAVEAGERAAREIL

HAMGKIPEDEIWQSEPESVDVPAQPITTTFLERHLPSVPGLLRLIGLTTI

FSATALGFLAHKRGLLVRV
```
and

SEQ ID NO: 2 is the amino acid sequence of the human MAO-A polypeptide:
```
MENQEKASIAGHMFDVVVIGGGISGLSAAKLLTEYGVSVLVLEARDRVGG

RTYTIRNEHVDYVDVGGAYVGPTQNRILRLSKELGIETYKVNVSERLVQY

VKGKTYPFRGAFPPVWNPIAYLDYNNLWRTIDNMGKEIPTDAPWEAQHAD

KWDKMTMKELIDKICWTKTARRFAYLFVNINVTSEPHEVSALWFLWYVKQ

CGGTTRIFSVTNGGQERKFVGGSGQVSERIMDLLGDQVKLNHPVTHVDQS

SDNIIIETLNHEHYECKYVINAIPPTLTAKIHFRPELPAERNQLIQRLPM

GAVIKCMMYYKEAFWKKKDYCGCMIIEDEDAPISITLDDTKPDGSLPAIM

GFILARKADRLAKLHKEIRKKKICELYAKVLGSQEALHPVHYEEKNWCEE

QYSGGCYTAYFPPGIMTQYGRVIRQPVGRIFFAGTETATKWSGYMEGAVE

AGERAAREVLNGLGKVTEKDIWVQEPESKDVPAVEITHTFWERNLPSVSG

LLKIIGFSTSVTALGFVLYKYKLLPRS
```

Description of Illustrative Embodiments

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

The MAO binding was modeled for the two molecules; MTA which is >1000 times better at inhibiting hMAO-A than hMAO-B, and ZIT which is >1000 times better at inhibiting hMAO-B than hMAO-A. In FIG. 4A and FIG. 4B, it is shown that modeling the two compounds in the pockets of MAO-A/B indicates that F208 and Y323 control access to the FAD reaction site.

These two studies from Regina and Fierro indicate that it possible to design small molecules that can bind to the channels of MAO-A or MAO-B, with high specificity, and that compounds that specific for MAO-A ten to be 'short and fat', whereas those for MAO-B are longer and thinner.

Exogenous MAO-B-Specific Substrates

Propyl-Amine-Ethers and Variants Thereof

FIG. 8A shows the published mechanism for cleavage of the ether bond between propylamine and the fluorophore resorufin (Albers et al., 2007). In FIG. 8B the same chemistry is shown for the conversion of pro-Drug APE-SN38 into the active SN38 drug. A number of structural forms of propylamine can be used for the same reaction, the minimal form FIG. 8C, and five and six membered ring versions (FIG. 8D and FIG. 8E). FIG. 8F is included for the sake of completeness, and shows how oxidation by MAO of a 1,2,3,6-tetrahydropyridine ring can also cleave a 4-oxy/4-thio or 4-amino linkaged, as was previously demonstrated in PCT Intl. Pat. Appl. Publ. No. WO 98/22110. Five membered pyrrol rings that utilize a vinyl ether (or thioether or amine) can also serve as MAO-B cleavable substrates, if denuded of the α-hydrogens at the $C_2$ position. FIG. 8G and FIG. 8H show how 2,2-difluoro- or 2,2-dimethyl-3-($R_2$)-oxy-1-($R_1$)-5H-pyrroles are converted into their respective ketones—being converted first to the pyrrol-1-ium by MAO, and then undergoing hydrolysis to generate the alcohol and ketone pairs.

As MAO-B is upregulated in glioma, the invention uses the enzymatic action of this enzyme to catalyze the conversion of nominally non-toxic pro-Drugs into active chemotherapeutic molecules. Two major types of pro-Drug compounds are considered to be particularly useful in the practice of the invention, both of which are converted into active forms by gliomal MAO-B, but which have different properties:

Firstly, pro-Drugs based on the ability of neutral 1,2,3,6-tetrahydropyridines to be converted into cationic pyridinium species and that the generated species will then partition into the mitochondria, driven by the mitochondrial membrane potential, and so will accumulate within this cellular compartment. A typical mitochondrial membrane potential is in the order of 180 mV, and so will drive a steady state concentration gradient of 1:1000, outside:inside mitochondria, of a lipophilic cation.

Secondly, inactive pro-Drugs can be generated from active chemotherapeutic drug compounds, or compounds which are cellular toxins, by the formation of amino-propyl-esters or amino-propyl-thioesters or amino-propyl-amines. The reaction of these pro-Drugs by MAO-B will then liberate the active, parental, cellular toxin.

Linker/warhead size and volume. A review of the crystal structures of MAO-B, co-crystallized with specific inhibitors, permitted elucidation of the general nature of linking moieties that will fit the MAO-B substrate channel. FIG. 9A, FIG. 9B, FIG. 9C, FIG. 9D, FIG. 9E, FIG. 9F, FIG. 9G, FIG. 9H, FIG. 9I, FIG. 9J, FIG. 9K, and FIG. 9L, show how seven different MAO-B inhibitors map the interior space of the MAO-B channel, and illustrate the basic dimensions of linker moieties.

These figures also demonstrate that structure (2), MP-MUS, fits within the overlaid specific MAO-B inhibitor structures. Based on the analysis of human MAO-B inhibitor size and volume, it was possible to model the size and volume of MAO-B substrate channel and pocket; which is approximately 20 Å in length, approximately 6 Å wide and up to 3.5 Å thick (FIG. 9M).

A MAO-B-sensitive form of the camptothecin, SN38, and the active drug compound are shown as structures (4) and (5).

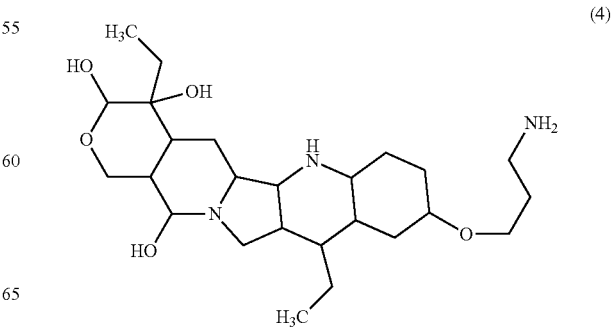

(4)

(5)

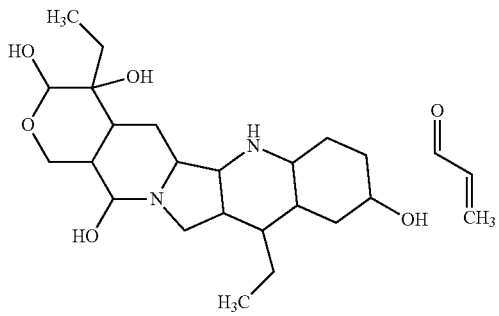

In these figures, APE-SN38, is shown to fit within the overlaid specific MAO-B inhibitor structures. Based on the analysis of human MAO-B inhibitor size and volume, it was possible to model the size and volume of MAO-B substrate channel and pocket; with camptothecin core of 18 Å×5 Å by 2.5 Å being accommodated. Also shown is the overlay of both MP-MUS and APE-SN38, color-coded, within the MAO-B enzyme, along with all seven inhibitors.

Design Criteria for Glioma-Specific Drugs

Designing a drug that specifically kills gliomas via the generation of a mitochondrial-accumulative toxin requires three main criteria.

First, the drug must have a toxic "warhead" that will destroy mitochondria (targeting mtDNA and mtRibosomal RNA).

Second, the drug must have a high MAO-B/MAO-A specificity ratio, so that gliomas, and not ordinary cells, are the primary target.

Third, the drug must possess intrinsic "druglikeness" and be able to cross the blood brain barrier.

Druglikeness is a calculated pharmaceutical scale, that is derived by comparing structures of potential drug compounds with know compounds that have useful pharmaceutical properties (Slimak, 2010; Gimenez et al., 2010; Lajiness et al., 2004; Lipinski et al., 2001; Lipinski et al., 1997; Verber et al., 2002).

Levels of MAO A and MAO-B Enzyme in Cancer Cells

The development of MP-MUS as an exemplary chemotherapeutic in the present invention was based on the well-known ability of the compound MPTP to be bio-converted into the mitochondrial targeting cationic MPP$^+$. Based on this work, variants of MPTP, which have been shown to have differential levels of bioconversion by MAO-A and MAO-B, can now be selectively synthesized that have MAO-A and/or MAO-B specificity. For instance, high levels of expression of MAO-A enzyme have been observed in high-grade prostate carcinoma (True et al., 2006). A comparison of 469 benign and 889 cancerous samples demonstrated that MAO-A protein expression was elevated in cancerous epithelium relative to benign secretory epithelium (P<0.0001), and MAO-A expression was significantly elevated in Gleason 4 or 5 samples relative to Gleason 3 samples (P<0.0001). MAO-B activity has been demonstrated to be significantly higher in glioblastoma multiformes, low-grade astrocytomas, and in anaplastic astrocytomas than in postmortem control brains (p<0.01) (Gabilondo et al., 2008).

Analogs of MP-MUS Based on Analogs of MPTP

A number of MPTP analogs have been prepared, and their MAO A/B substrate properties investigated. The crystal structures of human MAO-A and MAO-B are known, and that knowledge permits modeling studies and rational drug design. It has been found that: 1) the double bond at positions 4 and 5 of the tetrahydropyridine ring is essential for compounds to be MAO substrates; 2) substituents at the $C_4$ and $N_1$ positions of the tetrahydropyridine ring favorably increase the kinetics of MAO-A/MAO-B oxidation, and alter the specificity of the substrate towards the two enzymes (typically, the placement of an alkyl group anywhere else in the tetrahydropyridine ring diminishes reactivity towards both MAO-A and MAO-B, but differentially alters the substrate specificity toward the two enzymes); 3) substitution at the $N_1$ position is limited to small substituents (the N-methyl group appears to be the ideal size, while substituents such as N—H, N-methyl, N-ethyl and N-α-hydroxyethyl are less favorable; 4) the phenyl ring is not necessary for compounds to be MAO substrates, and replacement of the phenyl ring by a 1-methyl-2-pyrrolyl-, a benzyl-, or a phenoxy-group enhances MAO reactivity (e.g., the 4-cyclohexyl analog has been shown to be as effective of a substrate as MPTP); and 5) para-substituents on the phenyl ring produce steric hindrance unfavorable to reactivity, while ortho- and meta-substituents may have stabilizing interactions within the active site increasing reactivity.

MP-MUS Variants

The present invention is extendable to a variety of chemotherapeutic MAO-A and MAO-B compounds that have the generalized structure shown in FIG. 17. The MP-MUS "parental" compound comes in three functionalized blocks; an N-substituted tetrahydropyridine (targeting moiety or "seeker"), a linking group that is sculpted to fit the enzymatic pockets of either MAO-A and/or MAO-B and a therapeutic moiety (or "warhead") that has the property of causing damage to biological macromolecules like proteins, DNA and RNA, or to act as specific inhibitors of enzymes, transport systems, and/or signaling systems that are vital to life.

Exemplary Definitions

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

The term "e.g.," as used herein, is used merely by way of example, without limitation intended, and should not be construed as referring only those items explicitly enumerated in the specification.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof, that is pharmaceutically acceptable for administration to the relevant animal. The use of one or more delivery vehicles for chemical compounds in general, and chemotherapeutics in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed chemotherapeutic compositions.

As used herein, the term "patient" (also interchangeably referred to as "host" or "subject") refers to any host that can receive one or more of the pharmaceutical compositions disclosed herein. Preferably, the subject is a vertebrate animal, which is intended to denote any animal species (and preferably, a mammalian species such as a human being). In certain embodiments, a "patient" refers to any animal host including without limitation any mammalian host. Preferably, the term refers to any mammalian host, the latter including but not limited to, human and non-human primates, bovines, canines, caprines, cavines, corvines, epines, equines, felines, hircines, lapines, leporines, lupines, murines, ovines, porcines, ranines, racines, vulpines, and the like, including livestock, zoological specimens, exotics, as well as companion animals, pets, and any animal under the care of a veterinary practitioner. A patient can be of any age at which the patient is able to respond to inoculation with the present vaccine by generating an immune response. In particular embodiments, the mammalian patient is preferably human.

The phrase "pharmaceutically-acceptable" refers to molecular entities and compositions that preferably do not produce an allergic or similar untoward reaction when administered to a mammal, and in particular, when administered to a human. As used herein, "pharmaceutically acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from about 2 to about 20 amino acid residues in length, oligopeptides from about 10 to about 100 amino acid residues in length, and longer polypeptides including from about 100 amino acid residues or more in length. Furthermore, the term is also intended to include enzymes, i.e., functional biomolecules including at least one amino acid polymer. Polypeptides and proteins of the present invention also include polypeptides and proteins that are or have been post-translationally modified, and include any sugar or other derivative(s) or conjugate(s) added to the backbone amino acid chain.

As used herein, the term "substantially free" or "essentially free" in connection with the amount of a component preferably refers to a composition that contains less than about 10 weight percent, preferably less than about 5 weight percent, and more preferably less than about 1 weight percent of a compound. In preferred embodiments, these terms refer to less than about 0.5 weight percent, less than about 0.1 weight percent, or less than about 0.01 weight percent.

The term "glioma," as used herein, includes, without limitation, tumors that arise from non-neuronal cells of the central nervous system, such as from glial and related cells, such as ependymal cells, astrocytes, oligodendrocytes, and such like. The term glioma comprises disease conditions such as, without limitation, ependymomas, astrocytomas (and in particular, glioblastomas), oligodendrogliomas, oligoastrocytomas, and other gliomas of mixed origin, e.g., those originating from more than one type of cell, including cells of astrocytes, ependymal cells and/or oligodendrocytes. The affected tissue may include any one or more portions of the nervous system, such as, without limitation, the brain, spinal cord tissue, and such like.

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

As used herein, the terms "prevent," "preventing," "prevention," "suppress," "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be deemed medically useful.

As used herein, the terms "treat," "treating," and "treatment" refer to the administration of one or more compounds (either alone or as contained in one or more pharmaceutical compositions) after the onset of clinical symptoms of a disease state so as to reduce, or eliminate any symptom, aspect or characteristic of the disease state. Such treating need not be absolute to be deemed medically useful. As such, the terms "treatment," "treat," "treated," or "treating" may refer to therapy, or to the amelioration or the reduction, in the extent or severity of disease, of one or more symptom thereof, whether before or after its development afflicts a patient.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

The term "for example" or "e.g.," as used herein, is used merely by way of example, without limitation intended, and should not be construed as referring only those items explicitly enumerated in the specification.

In accordance with long standing patent law convention, the words "a" and "an" when used in this application, including the claims, denote "one or more."

EXAMPLES

The following examples are included to demonstrate illustrative embodiments of the invention. It should be appreciated by those of ordinary skill in the art that the techniques disclosed in these examples represent techniques discovered to function well in the practice of the invention, and thus can be considered to constitute preferred modes for its practice. However, those of ordinary skill in the art should, in light of the present disclosure appreciate that many changes can be made in the specific embodiments which are disclosed and still obtain a like or similar result without departing from the spirit and scope of the invention.

Example 1

Glioma-Specific Drug Design (1)

Using the aforementioned criteria, the inventors have designed and synthesized a novel pro-drug, the activated form of which has specifically designed to kill mammalian gliomas. This pro-drug, designated MP-MUS (I), is activated by mammalian MAO-B enzyme to form P$^+$-MUS (I), an acylation agent, whose ionic charge and inherent lipophilicity results in mitochondrial accumulation of the agent. This compound has been successfully tested in primary human glioblastoma cells, and shown to possess potent anti-cancer properties in vivo.

MP-MUS (I) is a Mitochondrial-Specific "Smart Bomb"

Figure 1:
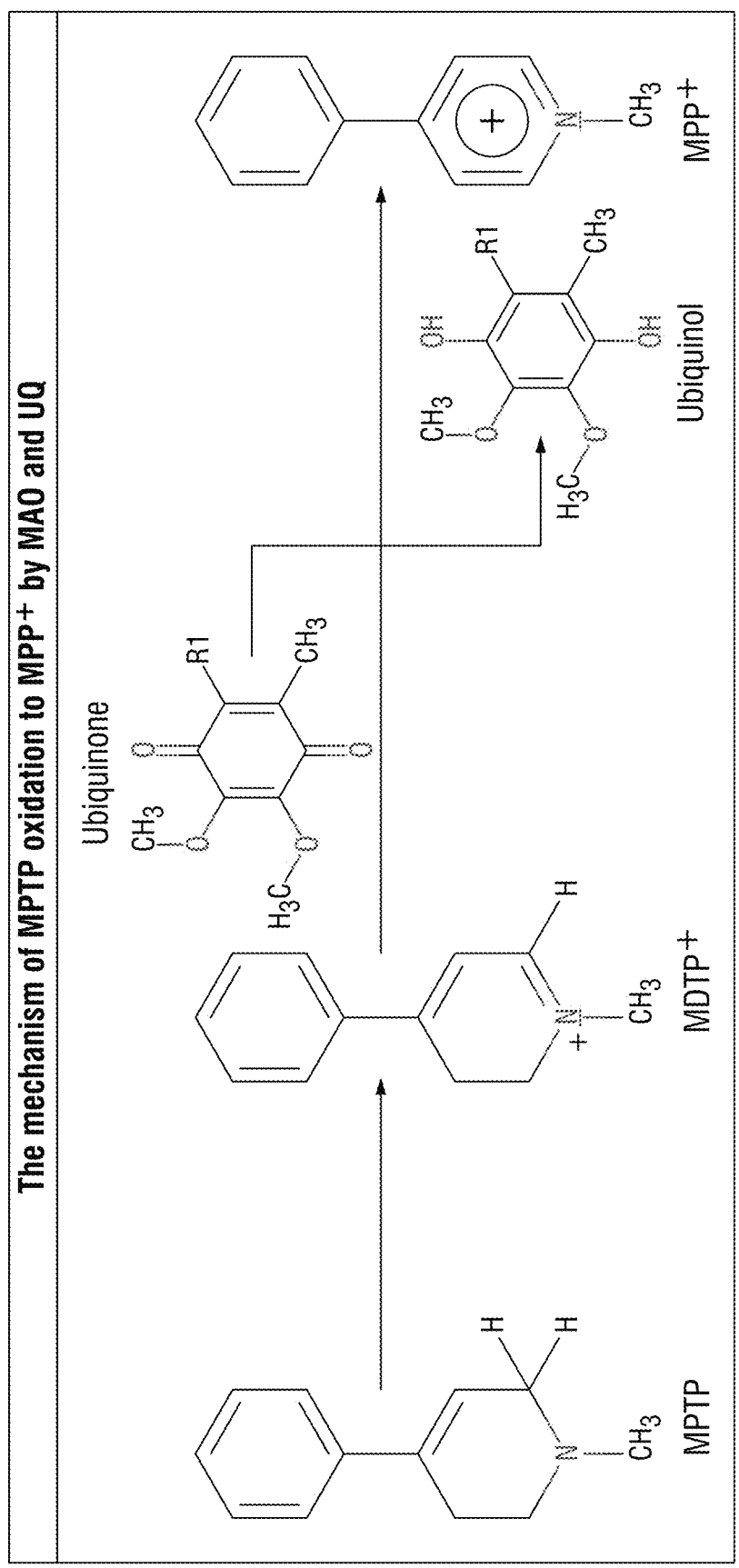

Design of a MAO-B Specific "warhead" compound. The MAO-B-mediated conversion of the 1-methyl-1,2,3,6-tetrahydropyridine moiety into a 1-methyl-pyridium cation facilitates mitochondrial targeting of the novel therapeutics described herein (FIG. 1).

The "warhead" of this "smart-bomb" chemotherapeutic is nitrogen mustard, which has been used in the treatment of cancer since the 1940s. Cyclization of N-chloroethane into reactive aziridine (an ammonium-based, three-membered ring), facilitates acylation of DNA/RNA bases, and particularly the N$_7$ group on guanine.

Traditional nitrogen mustards are subject to hydrolysis, and have a half-life of about 10 to 90 min at neutral pH (Price, 1968). In an ideal 'warhead' the reactivity of the 'warhead' will be tuned to the bioconversion of the gliomal MAO-B so that as large a part of 'warhead' activity as possible occurs within the mitochondria of the MAO-active, target cancer cell.

The inventors have designed a less-reactive nitrogen mustard that persists in the human body long enough to be activated by gliomal MAO-B, but is not a MAO-B suicide substrate, due to the incorporation of a carbonyl oxygen (see e.g., FIG. 2A and FIG. 2B). The carbonyl group is electron-withdrawing, and so it destabilizes the aziridine form, and produces two desirable effects: firstly, only a small fraction of the pro-drug/drug will be reactive at any one time, and secondly, the destabilized aziridine is more reactive than 'typical' nitrogen mustards.

Stabilization of aziridine affords the compound time to undergo the bioconversion by MAO-B in the glioma, and ensures the potency of the mature, mitochondrially-targeting active compound.

Additionally, it is possible that oxazol is formed via elimination of HCl and cyclization of immine/ethlychloride, which would also increase the stability of the acylating group.

Development of drug targeting systems. The rate at which MPTP is preferentially oxidized by MAO-B, in comparison to MAO-A, is typically presented as the ratio of the two $K_{cat}$'s; where $K_{cat}$ is the maximum catalytic activity divided by the $K_m$ (Heikkila et al., 1988). The MAO-B/MAO-A ratio is on the order of 4 to 10, depending on the particular buffering conditions (see e.g., Heikkila et al., 1988; Castagnoli et al., 1999; Nimkar et al., 1999; Palmer et al., 1997; Castagnoli et al., 1997). Moreover, the kinetics of MAO-B/MAO-A for a wide range of different substitutions on the two ring-systems of MPTP have been widely investigated (see e.g., Castagnoli et al., 1999; Nimkar et al., 1999; Palmer et al., 1997; Castagnoli et al., 1997).

Using the available information on the kinetics of different MPTP analogues (e.g., Palmer, 1998), the inventors have designed a pair of in silico 'ideal' MAO-A- and MAO-B-specific MPTP analogs. The substrate binding sites of MAO-A/B can be divided into three regions: an amine-binding pocket around the FAD moiety, P1', and a 'selectivity void,' which consists of two compartments, P2' and P3' (following the terminology of Efange and Boudreau, 1991). P2' is both larger and nearer to the FAD site, in MAO-A, whereas P3' is larger in MAO-B (Flamand et al., 2010; Castagnoli et al., 1999; Nimkar et al., 1999; Palmer et al., 1997; Castagnoli et al., 1997; Palmer, 1998; Efange and Boudreau, 1991; Binda et al., 2007).

MP-MUS (I) was designed so that it would fit into the pocket of human MAO-B, in silico. FIG. 2B shows the fit of MP-MUS (I) into the pocket of human MAO-B; (structure identification code, 2V60; Binda et al., 2007).

"Druglikeness." As noted above, candidate drug compounds to treat gliomas should possess "druglikeness," that is, they should possess properties that are predicted to lead to oral bioavailability, to readily cross the blood brain barrier, and to have adequate chemical and metabolic stability, and minimal toxic effects. The Molinspiration property calculator (Slimak, 2010) was used to examine the properties of both the pro-drug, MP-MUS(I), and the mature active "killer" compound, P$^+$-MUS (I). These data are shown in Table 1.

TABLE 1

'Druglikeness' of MP-MUS (I)/P$^+$-MUS (I) and MPTP/MPP$^+$

| Rule | Parameter | MP-MUS | MPTP | P$^+$-MUS | MPP$^+$ | MP | P$^+$ |
|---|---|---|---|---|---|---|---|
| Lipinski's | LogP | 2.24 | 2.33 | −3 | −2.73 | >1-5< | <<0 |
| | MW | 293 | 173 | 290 | 170 | <450 | |
| | H-Bond acceptors | 3 | 1 | 3 | 1 | ≤10 | |
| | H-Bond donors | 0 | 0 | 0 | 0 | ≤5 | |
| Veber's | Rotatable bonds | 6 | 1 | 6 | 1 | >6-10< | |
| | Mol Polar SA | 23.6 | 3.24 | 24.2 | 3.9 | >15-40< | |

A widely-used model for estimating druglikeness is known in the art as Lipinski's 'Rule of Five' (see e.g., Gimenez et al., 2010; Lajiness et al., 2004; Lipinski et al., 2001; and Lipinski et al., 1997). Lipinski's rule states that, in general, an orally-active drug should not violate more than one of the following criteria: 1) not more than five hydrogen bond donors (i.e., nitrogen or oxygen atoms with one or more hydrogen atoms); 2) not more than ten hydrogen bond acceptors (i.e., nitrogen or oxygen atoms); 3) a molecular mass that is less than 500 Daltons, and 4) an octanol-water partition coefficient log P not greater than five.

The ability of MP-MUS (I) to enter the brain, and for P+-MUS (I) to be retained in the brain, unable to re-cross the blood brain barrier, can be inferred from the partition coefficient, log P (van de Waterbeemd et al., 1998; Verber et al., 2002; Lajiness et al., 2004; Lipinski et al., 2001; Lipinski et al., 1997). The pro-drug has the correct lipophilicity to cross membranes, but is soluble enough in aqueous media to be supplied in oral form (van de Waterbeemd et al., 1998). Cationic P+-MUS (I) can cross the mitochondrial membrane (driven by the ΔΨ), has high solubility, and will not crystallize out of solution in the cellular matrix.

MP-MUS (I) also meets the "Veber rules" (Veber et al., 2002) for rotatable bond and polar surface area (see Table 1), and possesses significant "druglikeness" such that the mature drug compound, P+-MUS (I), accumulates within the mitochondria (driven by the membrane potential) at a concentration that can be as much as 1000× greater than that present in the cytosol.

Example 2

Glioma-Specific Drug Design (2)

APE-SN38, a Topoisomerase-Specific "Smart Bomb" for Cancer Treatment. Albers and co-workers (2007) demonstrated that aminopropyl ethers were labile in the presence of MAO, and it is this property that led to the development of a novel MAO-A/MAO-B assay system. 7-(3-aminopropoxy)-3H-phenoxazin-3-one is oxidized by MAO (via iminium and aldehyde intermediates), to release the fluorescent compound, resorufin, and propanal via a β-elimination reaction (FIG. 10). Utilizing the same iminium and aldehyde intermediates, followed by a β-elimination reaction, it should therefore be possible to convert existing pharmaceutical compounds having a tertiary/phenolic alcohol group into MAO-specific biotransformable drugs. For example, SN38 is the active metabolite of the pro-drug, camptothecin, and chemotherapeutic, irinotecan (Yao et al., 2011). To demonstrate the facility of utilizing extant therapeutic compounds having tertiary/phenolic alcohol groups in the methods described herein, the inventors exploited SN38 to develop a new "warhead" targetable therapeutic. In illustrative embodiments, the phenolic alcohol of position 10, ring A, of SN38 camptothecin structure was modified by the present inventors with propylamine to form the compound 7-ethyl-10-(3-aminprop)-oxy-camptothecine:

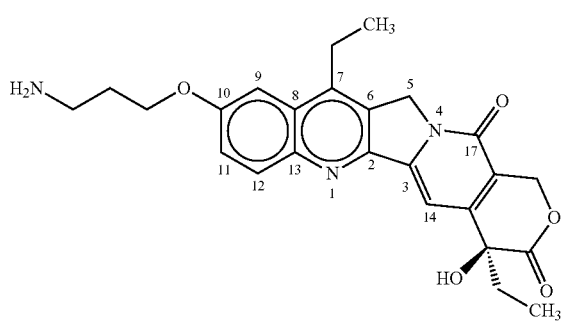

According to IUPAC nomenclature rules, the systematic name of the resulting compound can also be stated as either: (S)-4,11-diethyl-3,4,12,14-tetrahydro-4-hydroxy-3,14-dioxo1H-pyrano[3',4':6,7]-indolizino[1,2-b)]quinolin-9-oxy-propylamine, or (19S)-7-(3-aminopropoxy)-10,19-diethyl-19-hydroxy-17-oxa-3,13 diazapentacyclo[11.8.0.02, 11.04,9.015,20] henicosa-1(21),2,4(9),5,7,10,15(20)-heptaene-14,18-dione. In the present example, this compound was tested for its suitability as a therapeutic moiety in the methods of the invention.

Materials and Methods

Primary GBM. Primary human glioblastoma cells were obtained from surgical theater, and subsequently grown in MEM with penicillin/streptomycin and 10% FBS (Invitrogen Corp., Carlsbad, Calif., USA). After two or more weeks of growth and splitting, 250 µL of resulting cells (at a density of 1×10⁴ cells per mL) were plated into 96-well microtiter plates (Corning, Inc., New York City, N.Y., USA), and grown to confluence by incubation at 37° C. for at least 24 hr.

After 24 hrs, cells were treated with 20 µL/mL of ethanol, containing either the test drugs, inhibitors, or no additives (internal controls).

Selegiline (L-deprenyl) (Sigma-Aldrich, St. Louis, Mo., USA) was used as a specific inhibitor of MAO-B at concentrations of 2-10 µM, based on published reports (Hao et al., 1995), and was used at least an eight-fold higher concentration (2 µM=8*0.25 µM) based upon the approximate eight-fold higher expression level of MAO-B in GBM than in regular cells.

Epifluorescence Microscopy. Signals were acquired using a Nikon Eclipse TE2000-E fluorescent microscope equipped with a CoolSnap ES digital camera system (Roper Scientific, Tucson, Ariz., USA) containing an CCD-1300-Y/HS 1392× 1040 imaging array cooled by a Peltier device.

Images were recorded using Nikon NIS-Elements software version 3.2 Nikon Instruments Inc., Melville, N.Y., USA), and images were stored as jpg2000 files. Images were analyzed using the same NIS-Elements software.

Cell Viability Measurements. Cells were incubated with µM Hoechst 33258 (Cat #H1398) in the presence and absence of 500 nM Mitotracker® Red (Cat #M22425), or the reactive oxygen species specific reagent H₂DCFDA (6-carboxy-2',7'-dichlorodihydro fluorescein diacetate) for 1 hr (reagents obtained from Invitrogen, Corp. (Eugene, Oreg., USA). The buffer used was 5 mM glucose/3 mM Tris/30 mM HEPES/10 mM NaCl buffer (pH 7.4) at 37° C.

Fixing, Washing and Permeabilization of Cells. Cells were fixed in ice-cold 2% paraformaldehyde/phosphate buffered saline (PFA) for 2-24 hr, and cells were washed in 11.9 mM phosphate, 137 mM NaCl and 2.7 mM KCl (PBS; Fisher Bioreagents, Fair Lawn, N.J., USA) and then permeabilized in three washes of PBS+0.1% Triton X-100 (Sigma Aldrich).

Viability Cut-off. Cells were counted at 4× magnification, and cells were deemed to be non-viable if they had Hoechst signals>5 times the level found in untreated cells.

ddTUNEL. A Tdt reaction buffer was prepared daily diluting a stock solution of 125 mM Tris-HCl, 1 M sodium cacodylate, 1.25 mg/mL BSA, pH 6.6 by 1:5 and diluting 1:25 a 25 mM cobalt chloride stock solution. The sample was twice washed in this solution and then ≈50 µL of reaction buffer containing 20 U/mL of Tdt and 250 nM of labeled-ddUTP was applied to each of the sections, which were then incubated in a humidified box overnight at room temperature or for 2 hrs at 37° C. Roche Biotin-16-ddUTP (Roche Diagnostics, Branford, Conn., USA) was used throughout and was visualized using Texas-Red labeled Avidin (Baskin et al., 2010a; Baskin et al., 2010b).

Antibody Labeling. Anti-mitochondrial ribosomal protein L11 rabbit antibody (ab74285) and Anti-cytochrome c antibody (ab13575) were obtained from Abcam (Cambridge, Mass., USA), and were visualized using labeled secondary antibodies; Alexa Fluor 594 goat anti-mouse IgG (A-11032) and Alexa Fluor 488 goat anti-rabbit IgG (A-11034) from Invitrogen. Permeabilized cells were blocked with 10% equine sera (Invitrogen) for 1 hr, washed in PBS/0.1% Triton X-100 and then incubated overnight with primary antibody (1:1000), washed twice in PBS/0.1% Triton X-100, incubated with the secondary's overnight and then washed twice more. DNA was stained using DAPI (Invitrogen) by incubation with 30 nM DAPI in PBS for 5 min, and then cells were washed twice in PBS/0.1% Triton X-100. The wells were then filled with 100 μL PBS/0.1% Triton X-100, and imaging performed.

XTT Assay. Mitochondrial function was assayed using the XTT (2,3-Bis(2-methoxy-4-nitro-5-sulfophenyl)-2H-tetrazolium-5-carboxanilide) mitochondrial and extramitochondrial dehydrogenases assay method (Berridge et al., 2005; Huet et al., 1992) (Sigma-Aldrich). The medium was withdrawn from the cells that were then washed in 5 mM glucose/3 mM Tris/30 mM HEPES/10 mM NaCl buffer (pH 7.4) and treated with 0.5 mg/mL XTT in the same buffer for 1 hr at 37° C. The generated levels of formazan were read at 565-490 nm.

LDH Assay. After the XTT levels were determined the cells were washed using 2×250 μL of 5 mM glucose/3 mM Tris/30 mM HEPES/10 mM NaCl buffer (pH 7.4). The levels of lactate dehydrogenase activity in the presence of detergent (Korzeniewski and Callewaert, 1983; Decker and Lohmann-Matthes, 1988) were then assayed in each well (Corning). The final assay mixture contained 100 μL of 110 mM lactate, 3.35 mM $NAD^+$, 350 μM resazurin (Sigma-Aldrich), and 2.2 units/mL of diaphorase in 5 mM glucose/3 mM Tris/30 mM HEPES/10 mM NaCl buffer (pH 7.4) and 0.45% TritonX-100. The resorufin formed was measured over the course of 15 min in a plate reader using at 530/25 nm excitation (ex) and 590/35 nm emission (em). The rates at which resorufin was formed were proportional to the levels of LDH, and consequently, cell number (Korzeniewski and Callewaert, 1983; Decker and Lohmann-Matthes, 1988).

Protein Assay. Cell protein mass was measured using the Micro BCA Protein Assay Kit (Thermo-Fisher Scientific, Inc., Waltham, Mass., USA), supplemented with 1% sodium dodecyl sulfate (SDS) to solubilize all protein.

Synthesis of MP-MUS. The starting compound, methyl-1,2,3,6-tetrahydropyridin-4-yl-propanoic acid, was synthesized in three steps using the Wittig-Horner reaction, followed by lithium aluminum hydride reduction of the piperidine ring and ester hydrolysis of the ester, based on the published methodology (Differding and Ghosez, 1985).

Synthesis of ethyl (1-methylpiperidin-4-ylidene)propanoate (1). N-methyl-4-piperidone (0.5 gm, 4.42 mmol) was dissolved in anhydrous ether (5 mL) in a dry flask under argon and triethyl-2-phosphonopropionate (1.58 gm, 6.63 mmol) was added, followed by addition of sodium hydride (0.12 gm, 4.86 mmol) at 0° C. for 10 min. The reaction mixture was heated at reflux (50° C.) for 4 hr when thin layer chromatographic (TLC) analysis demonstrated that no starting material remained. Solvent was evaporated under vacuum, the residue was dissolved in dichloromethane (50 mL) and the solution washed with water (3×50 mL). The organic phase was dried ($MgSO_4$), evaporated to dryness and purified on a silica gel column using 2% methanol in dichloromethane. The pure compound 1 (0.54 gm) was obtained in 62% yield. $^1$H NMR 1 (CDCl$_3$) δ: 4.15 (m, 2H), 2.41-2.36 (m, 7H), 2.15 (s, 3H), 2.00 (t, J=7.2, 4H), 1.19 (t, J=7.6, 3H). MS: (M+1) calculated 198.27. found 198.35.

Synthesis of Ethyl (1-methyl-1,2,3,6-tetrahydropyridin-4-yl)propanoate (2). Compound 1 (0.4 gm, 2.02 mmol) was dissolved in anhydrous THF (5 mL) in a dry flask under argon atmosphere at −68° C. for 10 min. Lithium aluminum hydride (3 mL, 3.04 mmol) was added dropwise into this mixture and stirred for 1 hr. The reaction mixture was warmed to room temperature and again stirred for 1 hr, when TLC showed that no starting material remained. The reaction was quenched with 100 μL of $NH_4Cl$, filtered and evaporated under vacuum. The crude residue was dissolved in dichloromethane (50 mL) and washed with water (3×50 mL). The organic phase was dried and yielded the unsaturated ester 2 (~100% crude) which was directly saponified to acid. $^1$H NMR 2 (CDCl$_3$) δ: 5.78 (t, J=7.1, 1H), 4.39 (m, 2H), 3.16 (m, 1H), 2.88 (d, 2H), 2.52 (m, 2H), 2.18 (s, 3H), 2.01 (t, J=7.2, 2H), 1.21 (t, J=8.1, 3H), 1.1 (d, 3H). MS: (M+1) calculated 198.27. found 198.33.

Synthesis of methyl-1,2,3,6-tetrahydropyridin-4-yl-propanoic acid (3). Compound 2 (0.35 g, 1.77 mmol) was dissolved in TFA (5 mL) and 2 mL of 1 N NaOH solution was added into this mixture. The reaction mixture was heated at reflux (70° C.) for 2 hr when TLC showed that no starting material remained. Solvent was evaporated under vacuum and crude product was dissolved in dichloromethane (50 mL) and washed with brine (3×50 mL). The organic phase was dried ($MgSO_4$), evaporated to dryness and the crude product was purified on a silica gel column and using 2% methanol in dichloromethane as eluent. This afforded product 3 as white color solid (0.24 gm, 80% yield). $^1$H NMR 3 (CDCl$_3$) δ: 10.2 (bs, 1H), 5.72 (t, J=7.2, 1H), 3.19 (m, 1H), 2.85 (d, 2H), 2.50 (m, 2H), 2.18 (s, 3H), 2.03 (t, J=7.1, 2H), 0.91 (d, 3H).

MS: (M+1) calculated 170.22. found 170.28. Synthesis of chloroethyl-(methyl-1,2,3,6-tetrahydropyridin-4-yl)propanoyl)aziridinium (4)

Compound 3 (0.23 gm, 1.36 mmol) was dissolved in anhydrous dichloromethane (5 mL) in a dry flask under argon atmosphere and Benzotriazolyloxytris (dimethylamino) phosphonium Hexafluorophosphate (Sigma-Aldrich) (0.9 gm, 2.04 mmol) was added, followed by addition of bis(2-chloroethyl)amine (0.36 g, 2.04 mmol) at 0° C. for 10 min. The reaction mixture was warmed to room temperature and stirred for 3 hr, when TLC showed that no starting material remained. Solvent was evaporated under vacuum and crude product was extracted with dichloromethane (50 mL) and washed with water (3×50 mL). The organic extracted was dried and evaporated. The crude product was purified on a silica gel column and using 2% methanol in dichloromethane as eluent to isolate 4 (0.27 gm) in 77% yield. MS: M+K, calculated 296.78. found 296.90. $^1$H NMR 4 (DMSO-d$_6$) d: 4.03 (m, 5H, $CH_2$ and ArH), 3.05 (m, 2H, $CH_2$), 2.78 (d, J=10.5 Hz, 5H, $CH_2$, CH and $ArCH_2$), 1.23 (m, 10H, $ArCH_2$ and $CH_3$). The synthetic pathway is shown in FIG. 12.

Example 3

Killing Primary Human GBM Cells in Vitro Using MP-MUS(I)

1) Effect of MP-MUS (I) on Cell Growth and Mitochondria. Primary glioma human cells, (internally coded as "BT-111"), were obtained for a (first) resection of a Glioblastoma multiforme tumor, and grown in either 96-well microplate format or in slide tanks Cells were incubated with three different drugs; the traditional treatment; temozolomide, nitrogen mustard, or MP-MUS (I). The effects on cell growth and mitochondrial function are shown in FIG. 13A and FIG. 13B in the presence of MP-MUS (I), the parental mustard and Temozolomide in primary GBM cells; BT-111. These results demonstrate that MP-MUS (I) was a potent glioma toxin, with an $LD_{50}$ 5-fold lower than the standard chemotherapeutic drug, temozolomide. Of particular interest was the differing effect observed on mitochondria for these two compounds. MP-MUS (I) abolished half of the mitochondrial complex activity at concentrations of ≈2 μM, whereas temozolomide caused an increase in the levels of mitochondria in BT-111 cells, at concentrations>10 μM.

Growth (in microplate wells for 24 or 48 hr) of cells treated either with test drug or the ethanol vehicle alone was assayed using the lactate dehydrogenase assay method, and with the XTT mitochondrial complex activity, assay. Data collected from treatment with the parent nitrogen mustard, (bis-(2-chloroethyl)-amine), showed that it was not significantly toxic at concentrations less than 100 μM.

2) Effect of MP-MUS (I) on Mitochondrial Membrane Potential (ΔΨ). Mitochondrial targeting was confirmed using the ΔΨ probe, Mitotracker® Red. BT-111 cells were treated with MP-MUS (I), 12 μM for 24 hr with or without the addition of 10 μM selegiline (Geha et al., 2001); a MAO-B-specific inhibitor. Cells were then incubated with 500 nM Mitotracker® Red for 1 hr and after washing the living cells were imaged at 40× magnification in the wells of a 96-well plate (see FIG. 14A, FIG. 14B, FIG. 14C, and FIG. 14D). Selegiline had no effect on AT, but MP-MUS (I) lowered the signal to a statistically-significant 31%, a drop that was almost completely arrested by co-incubation with the MAO-B inhibitor selegiline.

3) Effect of MP-MUS (I) on Mitochondrial Proteins. To further demonstrate that the mitochondria was being targeted, the levels the mitochondrial matrix protein, L11, part of the mtRibosome and cytochrome c. found in the intermembrane space, were each probed using specific antibodies, in cells, following either 24 or 48 hrs' incubation with MP-MUS (I) (see FIG. 15A, FIG. 15B, and FIG. 15C). It was evident that there was an increase in the levels of L11 (red), and cytochrome c (green), after only 24 hrs' incubation. Extending the incubation time to 48 hrs resulted in >95% cell death, with the remaining survivors extremely damaged.

The control cells showed both proteins co-localized in the cytosol. After 24-hr incubation with 10 μM MP-MUS (I), cells had typical morphology, normal nuclei, but showed more mitochondrial protein. Extending the incubation to 48 hrs led to a loss of morphology, bloated nuclei, and a loss of defined mitochondria. Although the levels of L11 remained high, there was an almost complete loss of cytochrome c.

A paired sample underwent the same ligation following incubation with DNA polymerase/dNTP, so all overhanging ends were converted into blunt ends. The blue signals showed DAPI-stained DNA, while the red signals showed blunt-ended and total breaks (seen in FIG. 16A, FIG. 16B, FIG. 16C, FIG. 16D, FIG. 16E, and FIG. 16F). It was clear that MP-MUS (I) was extremely good at inducing DNA breaks, far more so than the conventional methylation agent, temozolomide. Moreover, the vast majority of the damage was extra-nuclear, indicating that it was mitochondrial DNA that was the target. Additionally, overhanging ends were the most common type of break observed.

Example 4

Killing Primary Human GBMCells in Vitro Using Ape-Sn38

Effect of APE-SN38 on cell growth; measured by protein levels and live cell counts. Primary glioma human cells (referred to as "BT-111" and "BT-115" herein), were obtained from resection of glioblastoma multiforme tumors from two separate patients, and grown in 96-well format.

Cells were incubated with a titration of APE-SN38 in the presence or absence of the MAO-B-specific inhibitor, selegiline, at 2 μM using published methods (Geha et al., 2001). Total cell protein mass was measured using the BCA/SDS method after a 24-hr incubation, and find an $LD_{50}$ of ≈50 μM APE-SN38 in both primary cell cultures, but that the MAO-B inhibitor selegiline affords the cells almost complete protection (FIG. 17A and FIG. 17B), indicating MAO-B bioconversion.

Cell counts (of five wells at each concentration), were also used to establish the numbers of live cells at each concentration (FIG. 18A and FIG. 18B).

Cell death at high concentrations of APE-SN38 could be arrested by co-incubation with 2 μM selegiline (see FIG. 19). FIG. 19 shows protected BT-111 and BT-115 GBM cultures from cell death. The protection afforded was seen after 24 hrs' incubation with APE-SN38. Cells were incubated for 24 hrs, then treated with Hoechst's viability stain, and fixed.

Example 5

Synthesis of APE-SN38

APE-SN38 was synthesized using the route of Albers, Rawls and Chang with 3-chloropropylamine (although N—$R_1$ substituted chloropropylamine is shown in the reaction scheme shown in FIG. 22).

N-R1,3 chloro-propylamine was Boc protected, to give the amine-protected, tert-butyl 3-chloropropyl-N-carbamate (1). The Boc-protected derivative was used to generate the SN38 (7-ethyl-10-hydroxycamptothecin) ether using $K_2CO_3$ in DMF. The product is an ether; 9-(Boc($R_1$)aminopropoxy)-7-ethyl-10-hydroxycamptothecin (2) was treated with trifluoroacetic acid to give the final product (wherein $R_1$=H); (19S)-7-(3-aminopropoxy)-10,19-diethyl-19-hydroxy-17-oxa-3,13-diazapentacyclohenicosa-1,2,4,5,7,10, 15-heptaene-14,18-dione (3), and purified by HPLC.

The NMR spectrum of the final product, APE-SN38 ($R_1$=H), is shown in FIG. 23.

Example 6

NMR Spectrum for MP-MUS

In DMSO the chloroethyl-(methyl-1,2,3,6-tetrahydropyridin-4-yl) propanoyl) aziridinium (4) was the most common form observed. The proton nmr, recorded in DMSO-d6, shows 22 H-signals of (4) (see FIG. 23).

$^1$H NMR 4 (DMSO-$d_6$) d: 4.03 (m, 5H, $CH_2$ and ArH), 3.05 (m, 2H, $CH_2$), 2.78 (d, J=10.5 Hz, 5H, $CH_2$, CH and $ArCH_2$), 1.23 (m, 10H, $ArCH_2$ and $CH_3$).

Example 7

Exemplary SN38-Related Compounds and Derivatives Thereof

Any chemotherapeutic that has requirement for either an alcohol or thiol for is action can be modified by being transformed into either an ether or thioether using an N-substituted 3-chloropropylamine, and thus also represent additional compounds that may be useful in the practice of the present invention. In addition to $R_1$=H (i.e., SN38), additional alternative $R_1$ groups are also contemplated to be useful in generating analogs and/or derivatives of the exemplary compound, APE-SN38, that are also expected to be pharmacologically effective in the methods of the present invention. Such variables include, without limitation, substituted and unsubstituted $C_1$-$C_6$ alkyl (including methyl, ethyl), benzyl, cyclopropyl, cyclobutyl, cyclopentyl, cyclohexyl, and cycloheptyl.

Figure 26A:
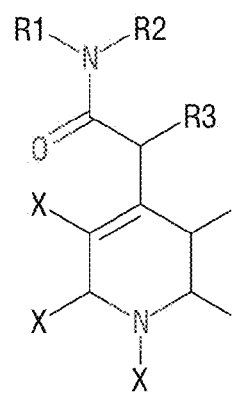

This example demonstrated that dipropylpropanamide-based linker has been synthesized that has high MAO-B activity/specificity (FIG. 26A). Previously-published work (Palmer et al.; 1998; and Yu et al., 2006) showed the general characteristics of N-substituted tetrahydropyridine compounds that had high MAO-A and/or MAO-B catalytic activity and/or specificity. For example, 4-cyclohexyl-1-methyl-1,2,3,6-tetrahydropyridine (FIG. 26B) and 1-methyl-4-(3-methylfuran-yl)-1,2,3,6-tetrahydropyridine (FIG. 26C) are excellent MAO-B substrates that exhibit a high degree of MAO-B specificity.

Figure 26B:
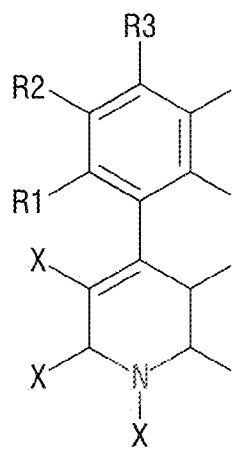
Figure 26C:
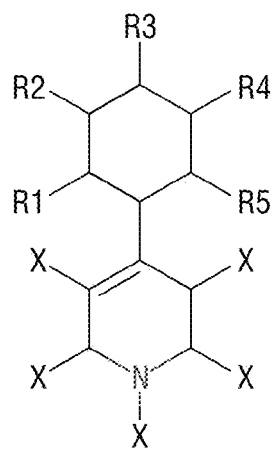
Figure 26D:
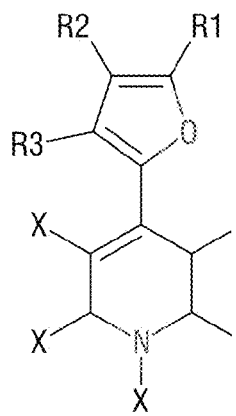
Figure 26E:
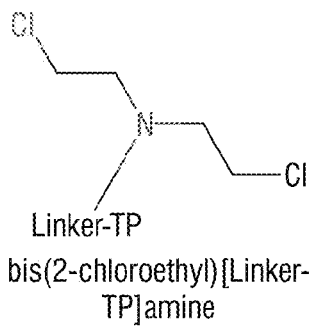
Figure 26F:
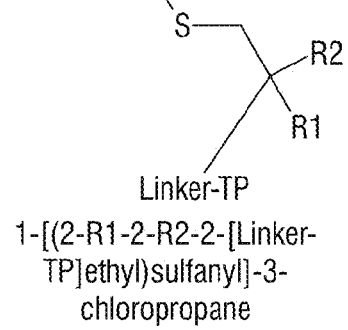
Figure 26G:
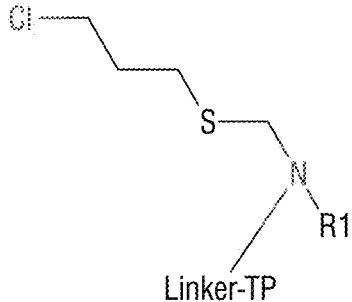
Figure 26H:
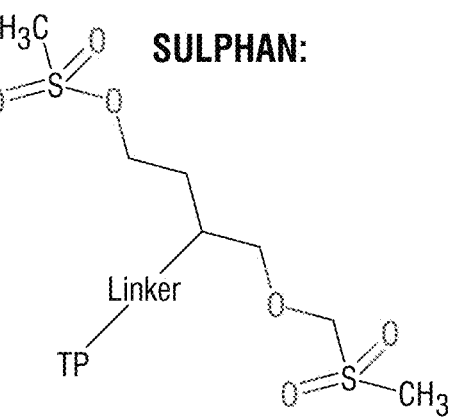
Figure 26I:
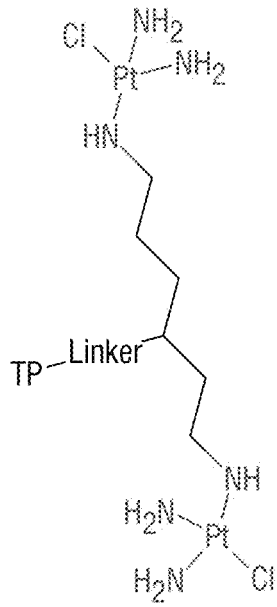
Figure 26J:
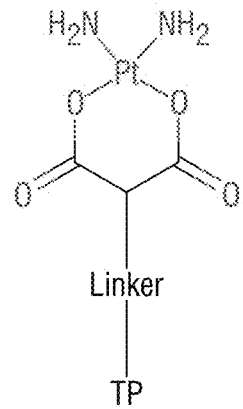

In FIG. 19A, R1, R2 and R3 each consist either of a 'warhead' and/or other substitution, wherein O═ may also be substituted for sulfur (S═), and the amide nitrogen may also be substituted for C—$R_4$. In FIG. 26B, $R_2$, $R_3$ and $R_4$ each consist either of a 'warhead' moiety and/or other substitution, and $R_1$ and $R_5$ are other substituents. In FIG. 26C, $R_2$, $R_3$ and $R_4$ each consist either of a 'warhead' moiety and/or other substitution, and $R_1$ and $R_5$ are other substituents. In FIG. 26D, $R_1$, $R_2$ and $R_3$ each consist either of a 'warhead' and/or other substitution, wherein the furanic —O— may also be substituted for sulfur —S— (thiophene), N—$R_4$ (X-pyrrole) or $R_4$—C—$R_5$ (5-$R_{4-5}$—$R_5$-cyclopenta-1,3-diene). The $R_1$, $R_2$, $R_3$, $R_5$, and $R_6$ substituents may include, but are not limited to, one or more of halogen, hydroxy-, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as —$NR_aR_b$, —$NR_aC(═O)R_b$, —$NR_aC(═O)NR_aNR_b$, —$NR_aC(═O)OR_b$, —$NR_aSO_2R_b$, —$C(═O)R_a$, —$C(═O)OR_a$, —$C(═O)NR_aR_b$, —$OC(═O)NR_aR_b$, —$OR_a$, —$SR_a$, —$SOR_a$, —$S(═O)_2R_a$, —$OS(═O)_2R_a$, and —$S(═O)_2OR_a$. In addition, each of these substituents may also be further substituted with one or more of the above substituents, including, without limitation, a substituted alkyl, a substituted aryl, a substituted arylalkyl, a substituted heterocycle, and/or a substituted heterocyclealkyl. $R_a$ and $R_b$ in this context may be the same or different and, independently, hydrogen, alkyl, haloalkyl, substituted alkyl, aryl, substituted aryl, arylalkyl, substituted arylalkyl, heterocycle, substituted heterocycle, heterocyclealkyl and/or substituted heterocyclealkyl.

"Warhead" therapeutic moiety. Exemplary therapeutic moieties include, but are not limited to, methylation/acylation agents that are known for their ability to conjugate both DNA and RNA. Examples include nitrogen and sulfur mustards, sulfan derivatives, and platins. In FIG. 27 illustrative DNA/RNA acylation agents are show that can also be combined with the linker and N-substituted tetrahydropyridine [linker-TP] moieties of the present invention to generate additional chemotherapeutics having the desired properties.

Example 8

Ability of MP-MUS to Treat Intracranial Human Glioblastoma

In the previous examples, it was shown that MP-MUS can successfully treat human glioblastoma multiforme xenograft cultures in a nude mouse flank model. The present study demonstrates the efficacy of MP-MUS in a nude mouse intracranial model of human glioblastoma, and to demonstrate that MP-MUS is able to cross the blood/brain barrier.

Brain Model Developments. Recently, Iwami and coworkers (2012) have developed an innovative methodology for the injection of human glioblastoma cultures into mouse brain via the postglenoid foramen. Previous orthotopic xenograft models typically required formal craniotomies requiring skin incision, bone removal and skin suturing, all of which are highly invasive and can result in excessive stress for the animals. Percutaneous injection into the adult mouse brain via the postglenoid foramen is a technically simpler, is significantly more time efficient, and importantly, is a less-stressful procedure for the mice to undergo, all of which translate into fewer procedural complications.

Postglenoid Foramen Injection. Initial studies demonstrated that it was possible to inject mice with a glioblastoma culture directly into the brain, and without the need for drilling through the skull. Some five minutes after injection and recovery from the anesthetic, the majority of the mice were walking around and were phenotypically normal within an hour. In the main study 40 SCID immuno-deficient mice were injected via the postglenoid foramen with glioblastoma in Matrigel™:tissue culture medium, 4:6, to a final cell load of 2,500,000 cells per animal; according to Iwami et al., (2012). The primary glioblastoma culture used, BT116, was an aggressive, grade IV, glioblastoma multiforme initially located in the left posterior temporal tumor 46 year-old man that proved fatal in less than 2 years. A number of the SCID mice died following the glioma injections or had deficits in the first few weeks following the initial injection. After >3 months, 24 animals were asymptomatic, and 22 animals were split into two groups; MP-MUS treated and Saline treated. The remaining pair was sacrificed and their brains were fixed/waxed and archived as pre-treatment controls.

Primary human glioblastoma grow very slowly in mice and the onset of symptoms following the inoculation of >2,000,000 cells directly into the mouse brain has been found to typically occur somewhere between 6 months and 12 months. It has also been noted that unlike typical transformed glioma cell lies, e.g., U87MG, U254 or U373MG, which grow as focal tumors, that can be easily identified using traditional histological staining techniques like H&E stains, primary human glioma infiltrate the whole brain and have to be identified using antibodies specific to human antigens (Valadex et al., 2014).

Drug Therapy and Symptom Monitoring. On day 115 mice are then given either 200 μL saline or 200 μL of 1 mg/mL MP-MUS in saline, via tail-vein injection. The same treatment was repeated on days 122 and 129.

The mice were initially placed in groups of 2×4 and 1×3 animals and were individually every 1-3 days. The mice were assessed for the onset of neurological symptoms caused by an intracranial tumor throughout the study. Symptoms in the mice that require euthanasia were sudden weight loss; >2 grams in 7 days, deficits of movement that caused the animal to be unable to drink/feed and immobility.

It was noted that some animals developed loss of fur, especially on the back of the neck, during the course of the study. The loss of hair was typically found to occur some 30-60 days before large neurological deficits were obvious.

TABLE 2

A STUDY EXAMINING THE EFFECT OF MP-
MUS ON AN INTRACRANIAL GBM MODEL

| Day 1 | 40 SCID mice injected with 2.5*10⁶ Glioblastoma cells | |
|---|---|---|
| Day 110 | Control Group 11 mice | MP-MUS Group 11 mice |
| Day 115 | 200 µL saline in tail | 200 µL 1 mg/mL MP-MUS in tail |
| Day 122 | 200 µL saline in tail | 200 µL 1 mg/mL MP-MUS in tail |
| Day 129 | 200 µL saline in tail | 200 µL 1 mg/mL MP-MUS in tail |
| Day 171 | 1$^{st}$ Saline mouse symptomatic | |
| Day 175 | 2$^{nd}$ Saline mouse symptomatic | |
| Day 207 | 3$^{rd}$ Saline mouse symptomatic | |
| Day 225 | | 1$^{st}$ MP-MUS mouse symptomatic |
| Day 235 | 4$^{th}$ Saline mouse symptomatic | |
| Day 241 | 5$^{th}$ Saline mouse symptomatic | |
| Day 248 | 6$^{th}$ Saline mouse symptomatic | |
| Day 277 | 7$^{th}$ Saline mouse symptomatic | |
| Day 307 | Final Day. All remaining animals sacrificed; brains were fixed/waxed/sliced | |

Table 2 shows the important study dates, starting from Day 0, where the animals received their brain injections of BT116 glioblastoma inoculum. The animals received three tail-vein injections of either saline or MP-MUS in saline, 7 days apart.

The weight changes in the two groups, with error bar representing the SEM is shown in FIG. 37. Weights were typically taken 5-6 times per week and some of the daily recordings are not shown to allow the individual error bars to be observed.

In FIG. 39, it should be noted bald patches on four Saline treated mice, arrowed, compared with the well-groomed MP-MUS treated mice. The human vimentin epitope that is recognized by the mouse-V9 antibody is labile with respect to peroxide. The mildest conditions that would remove the majority of endogenous and added peroxidase activity were used, so as not to destroy the human vimentin.

For vector mouse anti-vimentin clone #V9 and Santa Cruz Mouse anti-EGFR clone #528 the procedure was performed as shown. For CD3-ε, an extra step was used. CD3-ε was bound using an Arminian Hamster anti-CD3 epsilon antibody [145-2C11] conjugated with FITC, at a 1:10 dilution, for 1 hr. This was developed using a mouse anti-FITC antibody. Sigma clone FL-D6, at 1:100 dilution for 1 hr. Either an HRP-linked horse anti-Mouse antibody (to develop DAB), or the HiDef™ HRP-polymer system (which gives better signal-to-noise ratio, but may detect endogenous IgG in SCID mice) was used.

FIG. 40A, FIG. 40B, and FIG. 40C show the left, non-injected hemisphere of Saline #7. Saline #7 survived until the end of the trial at Day 307. Three fixed sagittal sections of both hemispheres were treated identically, except that the first pair of sections (FIG. 40A) was incubated with an anti-(human) Vimentin mouse antibody, the second pair of sections (FIG. 40B) is a negative control with no primary antibody added, and the final pair of sections (FIG. 40C) was incubated with an Armenian hamster anti-CD3-ε antibody conjugated with FITC, and then with a mouse anti-FITC antibody.

It can be noted that there is much co-localization of vimentin and CD3-ε, and that the level of background DAB signal is higher in these same regions. This is likely due to the presence of mouse immune cells that are positive for myeloperoxidase, from tumor-associated macrophages and tumor-associated neutrophils.

Detection of Vimentin and CD3-ε in MP-MUS Treated Animals. The same histological analysis was performed on three complete brains of the MP-MUS-treated animals. Their fixed brains were sectioned in groups of five, cut at 5 µm, with 3-4 individual brain sections per slide, the whole width of the brain. In MP-MUS #7, the inventors were unable to detect human vimentin in representative sections of the entire brain. At the injection site, there were voids, with some blood/blood breakdown products. CD3-ε cells, with low expression level were identifiable throughout the brain, but at lower density to those observed in the Saline treated mice. To ensure that this was not an artifact of labeling (due to lack of epitope retrieval or due to a loss of epitope during peroxidase blocking), the inventors labeled samples where the Uni-Trieve (Innovex Bioscience, CA, USA) mild epitope retrieval solution was also used, and no treatment with peroxide/periodate/NaBH$_4$ was performed. No human vimentin was identified in MP-MUS #7, including at the remains of the injection site, but it was possible to visualize the presence of CD3-ε, again near the injection site.

In MP-MUS #1, it was possible to detect <20 cell numbers in one section (40), but not in sections 50 µm either side of the part of the injection point (FIG. 40). In FIG. 45 <20 Vimentin-positive cells and many CD3-ε cells were co-localized near the gliomal injection site, without counter-staining In MP-MUS #8, no human gliomal cells were identified in the left, non-injected, hemisphere; but CD3-ε cells were identified. Vimentin- and CD3-ε-positive cells were identified near the injection site, but only CD3-ε (and not vimentin) was found in sections ≥200 µm away from this site. In FIG. 46, <20 vimentin-positive cells, and many CD3-ε cells were co-localized near the gliomal injection site, without counter staining. It was noted, however, that the CD3-ε cells had a different distribution to the vimentin-positive gliomal cells. Finally, Table 3 shows the presence of human vimentin and CD3 in mouse brains:

TABLE 3

PRESENCE OF HUMAN VIMENTIN AND CD3 IN MOUSE BRAINS

| | Control Group (11 mice) | | | MP-MUS-Treated Group (11 mice) | | |
|---|---|---|---|---|---|---|
| # | SAC | Right H | Left H | SAC | Right H | Left H |
| 1 | Day 171 | | | Day 225 | V−<br>CD3++ | V−<br>CD3++ |
| 2 | Day 175 | V++<br>CD3+++ | V+<br>CD3++ | Day 307 | | |
| 3 | Day 207 | V++<br>CD3+++ | V+<br>CD3++ | Day 307 | | |
| 4 | Day 235 | V++<br>CD3+ | V−<br>CD3+ | Day 307 | | |
| 5 | Day 241 | | | Day 307 | | |
| 6 | Day 248 | V++<br>CD3++ | V+<br>CD3++ | Day 307 | | |
| 7 | Day 277 | V++++<br>CD3+++ | V+++<br>CD3+++ | Day 307 | V−<br>CD3++ | V−<br>CD3++ |
| 8 | Day 307 | | | Day 307 | V+<br>CD3++++ | V−<br>CD3++++ |
| 9 | Day 307 | V++++<br>CD3+++ | V+++<br>CD3+++ | Day 307 | | |
| 10 | Day 307 | V+++<br>CD3+++ | V++<br>CD3+++ | Day 307 | | |
| 11 | Day 307 | | | Day 307 | | |

REFERENCES

The following references, to the extent that they provide exemplary procedural or other details supplementary to those set forth herein, are specifically incorporated herein in their entirety by express reference thereto:

Albers, A E et al., "Activity-based fluorescent reporters for monoamine oxidases in living cells,"*Chem. Comm. (Camb.)*, 44:4647-4649 (2007).

Baskin, D S et al., "Quantification and calibration of images in fluorescence microscopy," *Anal. Biochem.*, 404:118-126 (2010).

Baskin, D S et al., "Quantification of DNase type I ends, DNase type II ends, and modified bases using fluorescently labeled ddUTP, terminal deoxynucleotidyl transferase, and formamidopyrimidine-DNA glycosylase," *Biotechniques*, 49(1):505-512 (2010).

Berridge, M V et al., "Tetrazolium dyes as tools in cell biology: New insights into their cellular reduction," *Biotechnol. Annu. Rev.*, 11:127-152 (2005).

Binda, C et al., "Structures of human monoamine oxidase B complexes with selective noncovalent inhibitors: safinamide and coumarin analogs," *J. Med. Chem.*, 50(23): 5848-5852 (2007).

Boveris, A and Chance, B "The mitochondrial generation of hydrogen peroxide. General properties and effect of hyperbaric oxygen," *Biochem. J.*, 134(3):707-716 (1973).

Castagnoli, K et al., "The neuronal nitric oxide synthase inhibitor 7-nitroindazole also inhibits the monoamine oxidase-B-catalyzed oxidation of 1-methyl-4-phenyl-1,2,3,6-tetrahydropyridine," *Chem. Res. Toxicol.*, 10(4):364-368 (1997).

Castagnoli, K et al., "Neuroprotection by (R)-deprenyl and 7-nitroindazole in the MPTP C57BL/6 mouse model of neurotoxicity," *Neurobiol.*, 7(2):135-149 (1999).

Decker, T and Lohmann-Matthes, M L "A quick and simple method for the quantitation of lactate dehydrogenase release in measurements of cellular cytotoxicity and tumor necrosis factor (TNF) activity," *J. Immunol. Methods*, 115(1):61-69 (1988).

De Colibus, L et al., "Three-dimensional structure of human monoamine oxidase A (MAO-A): Relation to the structures of rat MAO-A and human MAO-B," *Proc. Natl. Acad. Sci. USA*, 102:12684-12689 (2005).

Differding, E and Ghosez, L "Intramolecular Diels-alder cyclo-additions of vinylketenimines: a convergent route to carbazoles and pyridocarbazole alkaloids," *Tetrahedron Lett.*, 26(13):1647-1650 (1985).

Dröge, W "Free radicals in the physiological control of cell function," *Physiol. Rev.*, 82(1):47-95 (2002).

Efange, S M N and Boudreau, R J "Molecular determinants in the bioactivation of the dopaminergic neurotoxin N-methyl-4-phenyl-1,2,3,6-tetrahydropyridine (MPTP)," *J. Comp. Aided Mol. Des.*, 5(5):405-417 (1991).

Fierro, A et al., "Similarities between the binding sites of monoamine oxidase (MAO) from different species—is Zebrafish a useful model for the discovery of novel MAO inhibitors?" In *An Integrated View of the Molecular Recognition and Toxinology—From Analytical Procedures to Biomedical Applications*, Radis-Baptista, G., (Ed.) (2013).

Flamand, V et al., "Targeting monoamine oxidase A in advanced prostate cancer," *J. Cancer Res. Clin. Oncol.*, 136(11):1761-1771 (2010).

Fukuda, T "Neurotoxicity of MPTP," *Neuropathology*, 21(4):323-332 (2001).

Gabilondo, A M et al., "Monoamine oxidase B activity is increased in human Gliomas," *Neurochem. Int.*, 52(1-2): 230-234 (2008).

Geha, R M et al., "Substrate and inhibitor specificities for human monoamine oxidase A and B are influenced by a single amino acid," *J. Biol. Chem.*, 276(13):9877-9882 (2001).

Gimenez, B G et al., "Evaluation of blockbuster drugs under the rule-of-five." *Pharmazie*, 65(2):148-152 (2010).

Hao, R et al., "Selegiline protects dopaminergic neurons in culture from toxic factor(s) present in the cerebrospinal fluid of patients with Parkinson's disease," *Neurosci. Lett.*, 200(2):77-80 (1995).

Hare, M L C "Tyramine oxidase: A new enzyme system in liver," *Biochem. J.*, 22(4):968-979 (1928).

Heikkila, R E et al., "Importance of monoamine oxidase A in the bioactivation of neurotoxic analogs of 1-methyl-4-phenyl-1,2,3,6-tetrahydropyridine," *Proc. Natl. Acad. Sci. USA*, 85:6172-6176 (1988).

Huet, O et al., "NADH-dependent dehydrogenase-activity estimation by flow cytometric analysis of 3-(4,5-dimethylthiazolyl-2-Y1)-2,5-diphenyltetrazolium bromide (MTT) reduction," *Cytometry*, 13(5):532-539 (1992).

Iwami, K et al., "A novel method of intracranial injection via the postglenoid foramen for brain tumor mouse models," *J. Neurosurgery*, 116:630-635 (2012).

Jekabsone, A et al., "Fibrillar beta-amyloid peptide $A\beta_{1-40}$ activates microglial proliferation via stimulating TNF-$\alpha$ release and $H_2O_2$ derived from NADPH oxidase: a cell culture study," *J. Neuroinflammation*, 3:24 (2006).

Jian, Y "Synthesis and mechanistic studies on the monoamine oxidase (MAO) catalyzed oxidation of 1,4-disubstituted-1,2,3,6-tetrahydropyridines," in *Chemistry*, Virginia Polytechnic Institute and State University, Blacksburg, Va., USA, p. 179 (1998).

Korzeniewski, C and Callewaert, D M "An enzyme-release assay for natural cytotoxicity," *J. Immunol. Methods*, 64(3):313-320 (1983).

Lajiness, M S et al., "Molecular properties that influence oral drug-like behavior," *Curr. Opin. Drug Discov. Develop.*, 7(4):470-477 (2004).

Lipinski, C A et al., "Experimental and computational approaches to estimate solubility and permeability in drug discovery and development settings," *Adv. Drug Delivery; Rev.*, 46(1-3):3-26 (2001).

Malmström, B G et al., "Copper-containing oxidases and superoxide dismutase. in: P. D. Boyer, (Ed.), The Enzymes, Academic Press, New York, pp. 507-579 (1975).

Mander, P K et al., "Microglia proliferation is regulated by hydrogen peroxide from NADPH oxidase," *J. Immunol.*, 176(2):1046-1052 (2006).

Nimkar, S K et al., "Studies on the monoamine oxidase-B-catalyzed biotransformation of 4-azaaryl-1-methyl-1,2,3,6-tetrahydropyridine derivatives," *J. Med. Chem.*, 42(10):1828-1835 (1999).

Ottoboni, S et al., "Deuterium isotope effect measurements on the interactions of the neurotoxin 1-methyl-4-phenyl-1,2,3,6-tetrahydropyridine with monoamine oxidase B," *J. Biol. Chem.*, 264:13684-13688 (1989).

Palmer, S L "The investigation of the active sites of monoamine oxidase (MAO) A and B and the study of MAO-A mediated neurotoxicity using 4-substituted tetrahydropyridines," Ph.D. thesis, Department of Chemistry, Virginia Polytechnic Institute, Blacksburg, Va., USA (1998).

Palmer, S L et al., "Probing the active sites of monoamine oxidase A and B with 1,4-di-substituted tetrahydropyridine substrates and inactivators," *J. Med. Chem.*, 40(13):1982-1989 (1997).

Price, C C et al., "Relative reactivities for monofunctional nitrogen mustard alkylation of nucleic acid components," *Biochim. Biophys. Acta*, 166(2):327-359 (1968).

Regina, G L et al., "New pyrrole inhibitors of monoamine oxidase: synthesis, biological evaluation, and structural determinants of MAO-A and MAO-B selectivity," *J. Med. Chem.*, 50(5):922-931 (2007).

Sharpe, M A et al., "Thimerosal-derived ethylmercury is a mitochondrial toxin in human astrocytes: possible role of Fenton chemistry in the oxidation and breakage of mtDNA," *J. Toxicol.*, 2012:1-12 (2012).

Shi, H et al., "1-Methyl-4-phenyl-2,3-dihydropyridinium is transformed by ubiquinone to the selective nigrostriatal toxin 1-methyl-4-phenylpyridinium," *FEES Lett.*, 461(3):196-200 (1999).

Toninello, A et al., "Amine oxidases in apoptosis and cancer," *Biochim. Biophys. Acta*, 1765:1-13 (2006).

True, L et al., "A molecular correlate to the Gleason grading system for prostate adenocarcinoma," *Proc. Natl. Acad. Sci. USA*, 103(29):10991-10996 (2006).

van de Waterbeemd, H et al., "Estimation of blood-brain barrier crossing of drugs using molecular size and shape and H-bonding descriptors," *J. Drug Target.*, 6(2):151-165 (1998).

Veber, D F et al., "Molecular properties that influence the oral bioavailability of drug candidates," *J. Med. Chem.*, 45(12):2615-2623 (2002).

Vizi, E S "Role of high-affinity receptors and membrane transporters in nonsynaptic communication and drug action in the central nervous system," *Pharmacol. Rev.*, 52:63-90 (2000).

Wang, Y X and Castagnoli, N J "Studies on the monoamine oxidase (MAO)-catalyzed oxidation of phenyl-substituted 1-methyl-4-phenoxy-1,2,3,6-tetrahydropyridine derivatives: factors contributing to MAO-A and MAO-B selectivity," *J. Med. Chem.*, 38(11):1904-1910 (1995).

Yao, Y-S et al., "Total synthesis of 7-ethyl-10-hydroxycamptothecin (SN38) and its application to the development of $C_{18}$-functionalized camptothecin derivatives," *Chemistry*, 17(37):10462-10469 (2011).

Youngster, S K et al., "Evaluation of the biological activity of several analogs of the dopaminergic neurotoxin 1-methyl-4-phenyl-1,2,3,6-tetrahydropyridine," *J. Neurochem.*, 48 (3): 929-934 (1987).

It should be understood that the examples and embodiments described herein are for illustrative purposes only and that various modifications or changes in light thereof will be suggested to persons skilled in the art and are to be included within the spirit and purview of this application and the scope of the appended claims. All references, including publications, patent applications and patents, cited herein are hereby incorporated by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A compound, comprising a targeting/seeker moiety that is specific for a mammalian monoamine oxidase B (MAO-B) enzyme, operably linked via a linker moiety to a therapeutic moiety that comprises a DNA acylating agent or a DNA damaging agent, wherein the therapeutic moiety is a neutral, blood-brain barrier-permeable pro-drug selected from the group consisting of a nitrogen mustard, a sulfur mustard, a platin tetranitrate, vinblastine, docetaxel, etoposide, SN38, camptothecin, carmustine, and any combination thereof, and further wherein the targeting/seeker moiety has a specificity for a MAO-B enzyme that is at least two-fold greater than its specificity for a MAO-A enzyme.

2. The compound of claim 1, wherein the targeting/seeker moiety is converted by the enzymatic action of mammalian MAO-B to its corresponding 1-methyl-4-(X)-pyridinium cationic form, where X is a therapeutic moiety selected from the group consisting of a nitrogen mustard, a sulfur mustard, a platin tetranitrate, and any combination thereof.

3. The compound of claim 2, wherein the resulting 1-methyl-4-(X)-pyridinium cationic form of the targeting/seeker moiety facilitates uptake of the compound across the mitochondrial membrane of a mammalian cell that expresses the MAO-B enzyme, at a rate that is at least about 5-fold to about 10-fold higher than that of the corresponding, non-ionic form of the pro-drug.

4. The compound of claim 3, wherein the resulting 1-methyl-4-(X)-pyridinium cationic form of the targeting/seeker moiety facilitates accumulation of the therapeutic moiety within one or more mitochondria of a population of mammalian cells to which the compound has been administered, in an amount that is about 50- to about 500-fold higher than the amount of the therapeutic moiety present in the cytosol of the mammalian cells following administration of the compound to the mammalian cells.

5. The compound of claim 1, wherein the first targeting/seeker moiety has a specificity for the MAO-B enzyme that is at least four-fold greater than the specificity for a MAO-A enzyme.

6. The compound of claim 1, wherein the targeting/seeker moiety is 1-methyl-1,2,3,6-tetrahydropyridine, 1-cyclopropyl-1,2,3,6-tetrahydropyridin.

7. The compound of claim 1, wherein the linker moiety comprises 2-methylpropanamide, cyclohexane.

8. The compound of claim 1, wherein the therapeutic moiety, is operably linked to the linker moiety and is selected from the group consisting of bis(2-chloroethyl) [Linker-TP]amine, 1-[(2-$R_1$-2-$R_2$-2-[Linker-TP]ethyl)sulfanyl]-3-chloro-propane, ({[(3-chloropropyl)sulfanyl]methyl})[Linker-TP]-$R_1$-amine, 3-[Linker-TP]-4-(methanesulfonylmethoxy)butyl methanesulfonate, 1,10-dichloro-5-[Linker-TP]-2,9-diaza-1,10-diplatinadecane-1,1,10,10-tetramine, and 2,2-diamino-5-[Linker-TP]-1,3-dioxa-2-platinacyclohexane-4,6-dione, wherein $R_1$, and $R_2$ are each halogen, hydroxyl, oxo, cyano, nitro, amino, alkylamino, dialkylamino, alkyl, alkoxy, alkylthio, haloalkyl,aryl, arylalkyl, heteroaryl, heteroarylalkyl, heterocycle, heterocyclealkyl, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, $C(=O)OR_a$, —$C(=O)NR_aR_b$, —$C(=O)NR_aR_b$—$OR_a$, —$SR_a$, —$SOR_a$, —$SOR_b$, —$S(=O)_2R_a$, —$OS(=O)_2R_a$, —$S(=O)_2$ $OR_a$, substituted alkyl, substituted aryl, substituted arylalkyl, substituted heterocycle, or substituted heterocyclealkyl;

wherein $R_3$ is halogen, hydroxyl, oxo, cyano, nitro, amino, alkylamino, dialkylamino, alkyl, alkoxy, alkylthio, haloalkyl,aryl, arylalkyl, heteroaryl, heteroarylalkyl, heterocycle, heterocyclealkyl, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, $C(=O)OR_a$, —$C(=O)NR_aR_b$, —$C(=O)NR_aR_b$, —$OR_a$, —$SR_a$, —$SOR_a$, —$SOR_b$, —$S(=O)_2R_a$, —$OS(=O)_2R_a$, —$S(=O)_2OR_a$, substituted alkyl, substituted aryl, substituted arylalkyl, substituted heterocycle, or substituted heterocyclealkyl; and wherein $R_a$ and $R_b$ are the same or different and, are, independently, hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

9. The compound of claim 1, defined as 2-$R_3$—N—$R_2$—N—$R_1$-2-(1-X-1,2,3,6-tetrahydropyridin-4-yl) acetamide, 4-phenyl-1-X-1,2,3,6-tetrahydropyridine, 4-cyclohexyl-1-X-1,2,3,6-tetrahydropyridine, or 4(5-$R_1$-4-$R_2$-3-$R_3$-furan-2-yl)-1-X-1,2,3,6-tetrahydropyridine, wherein $R_1$, $R_2$, and $R_3$ are each halogen, hydroxyl, oxo, cyano, nitro, amino, alkylamino, dialkylamino, alkyl, alkoxy, alkylthio, haloalkyl,aryl, arylalkyl, heteroaryl, heteroarylalkyl, heterocycle, heterocyclealkyl, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, $C(=O)$ $OR_a$, —$C(=O)NR_aR_b$, —$C(=O)NR_aR_b$, —$OR_a$, —$SR_a$, —$SOR_a$, —$SOR_b$, —$S(=O)_2R_a$, —$OS(=O)_2R_a$, —$S(=O)_2OR_a$, substituted alkyl, substituted aryl, substituted arylalkyl, substituted heterocycle, or substituted heterocyclealkyl;

wherein $R_a$ and $R_b$ are the same or different and, are, independently, hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl; and further wherein X is a therapeutic moiety selected from the group consisting of a nitrogen mustard, a sulfur mustard, a platin tetranitrate, and any combination, thereof.

10. The compound of claim 1, wherein the pro-drug is catalyzed to an active metabolite selected from the group consisting of:

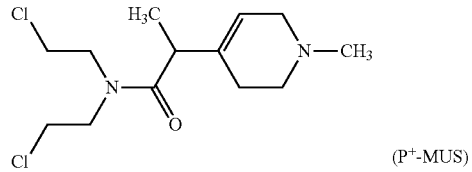

(P⁺-MUS)

and

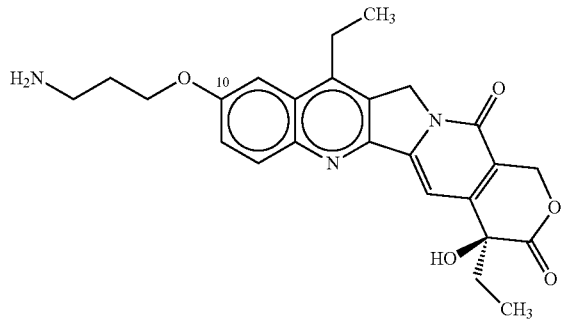

APE-SN-38 (P⁺-SN38).

11. The compound of claim 10, wherein the pro-drug is catalyzed to the active metabolite,

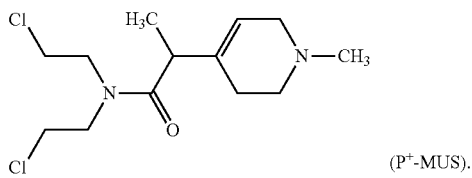 [SMILES: CC(C(=O)N(CCCl)CCCl)C1=CCN(C)CC1 ; "(P+-MUS),"]

(P⁺-MUS).

12. The compound of claim 6, wherein the targeting/seeker moiety is 1-methyl-1,2,3,6-tetrahydropyridine.

13. The compound of claim 7, wherein the at least a first linker moiety comprises 2-methylpropanamide.

14. The compound of claim 1, formulated for administration to a mammalian host cell.

15. The compound of claim 1, adapted and configured as part of a therapeutic kit that further comprises a pharmaceutically-acceptable buffer or diluent, and at least a first set of instructions for administration of the compound to a human in need thereof.

16. A compound, comprising a 1-methyl-1,2,3,6-tetrahydropyridine, 1-cyclopropyl-1,2,3,6-tetrahydropyridin- targeting moiety operably linked via 2-methylpropanamide to a a neutral, blood-brain barrier-permeable pro-drug selected from the group consisting of a nitrogen mustard, a sulfur mustard, a platin tetranitrate, vinblastine, docetaxel, etoposide, SN38, camptothecin, carmustine, and any combination thereof, wherein the targeting moiety is converted by the enzymatic action of a mammalian MAO-B enzyme to its corresponding 1-methyl-4-(X)-pyridinium cationic form at a rate that is at least about 50-fold to about 500-fold higher than that of the corresponding neutral pro-drug.

17. The compound of claim 16, wherein the resulting 1-methyl-4-(X)-pyridinium cationic form of the targeting moiety facilitates uptake of the compound across the mitochondrial membrane of a mammalian cell that expresses the MAO-B enzyme, at a rate that is at least about 5-fold to about 10-fold higher than that of the corresponding, neutral pro-drug.

18. A MAO-B-convertible, tetrahydropyridine chemotherapeutic delivery system, comprising a chemotherapeutic agent that possesses DNA acylating or DNA damaging activity, operably linked, via a chemical linker moiety, to a mitochondrial-targeting moiety that has a specificity for MAO-B that is at least four-fold greater than that for MAO-A.

19. The MAO-B-convertible, tetrahydropyridine chemotherapeutic delivery system of claim 18, having the general formula: 1-methyl-4-(X)-pyridine, wherein X is a chemotherapeutic moiety selected from the group consisting of a nitrogen mustard, a sulfur mustard, a platin tetranitrate, and any combination thereof.

20. The MAO-B-convertible, tetrahydropyridine chemotherapeutic delivery system of claim 18, wherein the chemotherapeutic agent comprises a nitrogen mustard, a sulfur mustard, a sulfan, a platin tetranitrate, temozolomide, camptothecin, irinotecan, carmustine, or any combination thereof.

21. The MAO-B-convertible, tetrahydropyridine chemotherapeutic delivery system of claim 20, wherein the chemotherapeutic agent comprises an SN38 metabolite of the pro-drug, camptothecin.

22. The MAO-B-convertible, tetrahydropyridine chemotherapeutic delivery system of claim 20, defined as N,N-bis(2-chloroethyl)-2-(1-methyl-1,2,3,6-tetrahydropyridin-4-yl)propanamide (MP-MUS).

23. The MAO-B-convertible, tetrahydropyridine chemotherapeutic delivery system of claim 19, wherein the platin tetranitrate is cis-platin.

24. A composition comprising: (a) the compound of claim 1, or the MAO-B-convertible, tetrahydropyridine chemotherapeutic delivery system of claim 18; and (b) a pharmaceutically-acceptable carrier, buffer, excipient, diluent, vehicle, or any combination thereof.

25. The composition of claim 24, further comprising one or more additional compounds selected from the group consisting of an antineoplastic agent, a cytotoxic agent, a cytostatic agent, a therapeutic molecule, a radiotherapeutic molecule, a chemotherapeutic molecule, and any combination thereof.

26. The composition of claim 25, wherein the one or more additional compounds comprises a sulfan, a platin tetranitrate, a nitrogen mustard, a sulfur mustard, camptothecin, temozolomide, APE-SN38, vinblastine, docetaxel, etoposide, carmustine, a topoisomerase, or an active metabolite thereof.

27. The composition of claim 24, formulated for administration to a mammal diagnosed with glioma astrocytoma, ependymoma, oligodendroglioma, or any combination thereof.

28. The composition of claim 26, wherein the active metabolite is

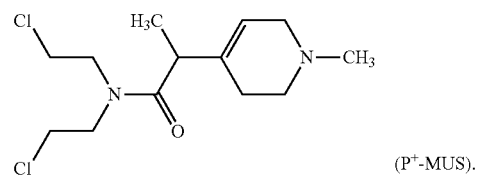

(P$^+$-MUS).

29. The composition of claim 27, wherein the glioma is selected from the group consisting of Glioblastoma Multiforme (GBM), recurrent Glioblastoma Multiforme (rGBM), an oligodendroglioma, a brainstem glioma, a mixed glioma, and any combination thereof.

30. The composition of claim 29, wherein the glioma is selected from the group consisting of a radiation-resistant glioma, a tumor comprising one or more gliomal stem cells, an advanced-stage glioma, an advanced-grade gliomal tumor, and any combination thereof.

31. A therapeutic kit for treating a mammalian cancer, comprising a) the compound of claim 1, the MAO-B-convertible, tetrahydropyridine chemotherapeutic delivery system of claim 18, or the composition of claim 16; and b) at least a first set of instructions for administration of the compound, the system, or the composition to a mammal in need thereof.

32. The therapeutic kit of claim 31, further comprising one or more additional anti-cancer agents formulated for administration to a mammal.

33. A method of targeting a therapeutic agent to one or more cancer cell mitochondria in an animal in need of anti-cancer therapy, comprising providing an effective amount of the composition of claim 24 to one or more cells, tissues, or organs of the animal, wherein the concentration of the therapeutic agent localized to the mitochondria is substantially higher than the concentration of the therapeutic agent remaining in the cytosol of the one or more cancer cells.

34. The method of claim 33, wherein the composition comprises a mitochondrially-localizable, cytotoxic or chemoactive compound.

35. The method of claim 34, wherein the composition comprises

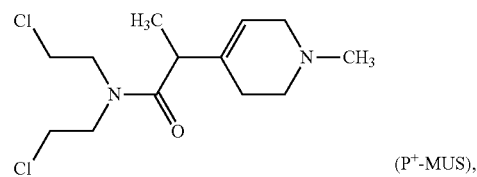

(P$^+$-MUS),

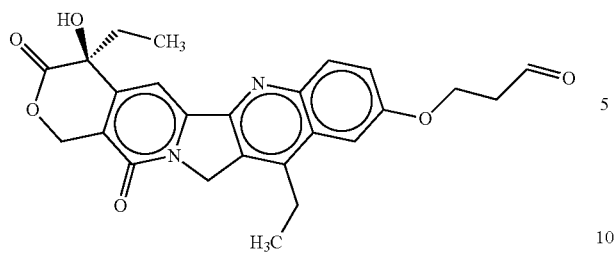

amino propyl ether (APE)-7-ethyl-10-hydroxycamptothecin ($P^+$-SN38), or any combination thereof.

36. A method of increasing the effectiveness of a chemotherapeutic agent in killing cancer cells in an animal, comprising administering an effective amount of the composition of claim 24 to one or more cells, tissues, or organs of the animal, wherein the effectiveness of the composition for killing one or more cancer cells in the animal is substantially greater than the effectiveness of administering a composition comprising the pro-drug alone.

* * * * *

SEQUENCE LISTING

```
<160> NUMBER OF SEQ ID NOS: 2

<210> SEQ ID NO 1
<211> LENGTH: 519
<212> TYPE: PRT
<213> ORGANISM: Homo sapiens

<400> SEQUENCE: 1

Met Ser Asn Lys Cys Asp Val Val Val Gly Gly Gly Ile Ser Gly
1               5                   10                  15

Met Ala Ala Lys Leu Leu His Asp Ser Gly Leu Asn Val Val Val
            20                  25                  30

Leu Glu Ala Arg Asp Arg Val Gly Gly Arg Thr Tyr Thr Leu Arg Asn
            35                  40                  45

Gln Lys Val Lys Tyr Val Asp Leu Gly Gly Ser Tyr Val Gly Pro Thr
    50                  55                  60

Gln Asn Arg Ile Leu Arg Leu Ala Lys Glu Leu Gly Leu Glu Thr Tyr
65                  70                  75                  80

Lys Val Asn Glu Val Glu Arg Leu Ile His His Val Lys Gly Lys Ser
                    85                  90                  95

Tyr Pro Phe Arg Gly Pro Phe Pro Pro Val Trp Asn Pro Ile Thr Tyr
                100                 105                 110

Leu Asp His Asn Asn Phe Trp Arg Thr Met Asp Asp Met Gly Arg Glu
            115                 120                 125

Ile Pro Ser Asp Ala Pro Trp Lys Ala Pro Leu Ala Glu Glu Trp Asp
        130                 135                 140

Asn Met Thr Met Lys Glu Leu Leu Asp Lys Leu Cys Trp Thr Glu Ser
145                 150                 155                 160

Ala Lys Gln Leu Ala Thr Leu Phe Val Asn Leu Cys Val Thr Ala Glu
                    165                 170                 175

Thr His Glu Val Ser Ala Leu Trp Phe Leu Trp Tyr Val Lys Gln Cys
                180                 185                 190

Gly Thr Thr Arg Ile Ile Ser Thr Thr Asn Gly Gly Gln Glu Arg Lys
            195                 200                 205

Phe Val Gly Gly Ser Gly Gln Val Ser Glu Arg Ile Met Asp Leu Leu
        210                 215                 220

Gly Asp Arg Val Lys Leu Glu Arg Pro Val Ile Tyr Ile Asp Gln Thr
225                 230                 235                 240

Arg Glu Asn Val Leu Val Glu Thr Leu Asn His Glu Met Tyr Glu Ala
                    245                 250                 255

Lys Tyr Val Ile Ser Ala Ile Pro Pro Thr Leu Gly Met Lys Ile His
                260                 265                 270

Phe Asn Pro Pro Leu Pro Met Met Arg Asn Gln Met Ile Thr Arg Val
            275                 280                 285

Pro Leu Gly Ser Val Ile Lys Cys Ile Val Tyr Tyr Lys Glu Pro Phe
        290                 295                 300

Trp Arg Lys Lys Asp Tyr Cys Gly Thr Met Ile Ile Asp Gly Glu Glu
305                 310                 315                 320

Ala Pro Val Ala Tyr Thr Leu Asp Asp Thr Lys Pro Glu Gly Asn Tyr
                    325                 330                 335
```

```
Ala Ala Ile Met Gly Phe Ile Leu Ala His Lys Ala Arg Lys Leu Ala
            340                 345                 350

Arg Leu Thr Lys Glu Glu Arg Leu Lys Lys Leu Cys Glu Leu Tyr Ala
        355                 360                 365

Lys Val Leu Gly Ser Leu Glu Ala Leu Glu Pro Val His Tyr Glu Glu
370                 375                 380

Lys Asn Trp Cys Glu Glu Gln Tyr Ser Gly Gly Cys Tyr Thr Thr Tyr
385                 390                 395                 400

Phe Pro Pro Gly Ile Leu Thr Gln Tyr Gly Arg Val Leu Arg Gln Pro
                405                 410                 415

Val Asp Arg Ile Tyr Phe Ala Gly Thr Glu Thr Ala Thr His Trp Ser
            420                 425                 430

Gly Tyr Met Glu Gly Ala Val Glu Ala Gly Glu Arg Ala Ala Arg Glu
        435                 440                 445

Ile Leu His Ala Met Gly Lys Ile Pro Glu Asp Glu Ile Trp Gln Ser
    450                 455                 460

Glu Pro Glu Ser Val Asp Val Pro Ala Gln Pro Ile Thr Thr Thr Phe
465                 470                 475                 480

Leu Glu Arg His Leu Pro Ser Val Pro Gly Leu Leu Arg Leu Ile Gly
                485                 490                 495

Leu Thr Thr Ile Phe Ser Ala Thr Ala Leu Gly Phe Leu Ala His Lys
            500                 505                 510

Arg Gly Leu Leu Val Arg Val
        515

<210> SEQ ID NO 2
<211> LENGTH: 527
<212> TYPE: PRT
<213> ORGANISM: Homo sapiens

<400> SEQUENCE: 2

Met Glu Asn Gln Glu Lys Ala Ser Ile Ala Gly His Met Phe Asp Val
1               5                   10                  15

Val Val Ile Gly Gly Gly Ile Ser Gly Leu Ser Ala Ala Lys Leu Leu
            20                  25                  30

Thr Glu Tyr Gly Val Ser Val Leu Val Leu Glu Ala Arg Asp Arg Val
        35                  40                  45

Gly Gly Arg Thr Tyr Thr Ile Arg Asn Glu His Val Asp Tyr Val Asp
    50                  55                  60

Val Gly Gly Ala Tyr Val Gly Pro Thr Gln Asn Arg Ile Leu Arg Leu
65                  70                  75                  80

Ser Lys Glu Leu Gly Ile Glu Thr Tyr Lys Val Asn Val Ser Glu Arg
                85                  90                  95

Leu Val Gln Tyr Val Lys Gly Lys Thr Tyr Pro Phe Arg Gly Ala Phe
            100                 105                 110

Pro Pro Val Trp Asn Pro Ile Ala Tyr Leu Asp Tyr Asn Asn Leu Trp
        115                 120                 125

Arg Thr Ile Asp Asn Met Gly Lys Glu Ile Pro Thr Asp Ala Pro Trp
    130                 135                 140

Glu Ala Gln His Ala Asp Lys Trp Asp Lys Met Thr Met Lys Glu Leu
145                 150                 155                 160

Ile Asp Lys Ile Cys Trp Thr Lys Thr Ala Arg Arg Phe Ala Tyr Leu
                165                 170                 175

Phe Val Asn Ile Asn Val Thr Ser Glu Pro His Glu Val Ser Ala Leu
```

-continued

```
                    180                 185                 190
Trp Phe Leu Trp Tyr Val Lys Gln Cys Gly Gly Thr Thr Arg Ile Phe
            195                 200                 205

Ser Val Thr Asn Gly Gly Gln Glu Arg Lys Phe Val Gly Gly Ser Gly
        210                 215                 220

Gln Val Ser Glu Arg Ile Met Asp Leu Leu Gly Asp Gln Val Lys Leu
225                 230                 235                 240

Asn His Pro Val Thr His Val Asp Gln Ser Ser Asp Asn Ile Ile Ile
                245                 250                 255

Glu Thr Leu Asn His Glu His Tyr Glu Cys Lys Tyr Val Ile Asn Ala
            260                 265                 270

Ile Pro Pro Thr Leu Thr Ala Lys Ile His Phe Arg Pro Glu Leu Pro
        275                 280                 285

Ala Glu Arg Asn Gln Leu Ile Gln Arg Leu Pro Met Gly Ala Val Ile
        290                 295                 300

Lys Cys Met Met Tyr Tyr Lys Glu Ala Phe Trp Lys Lys Lys Asp Tyr
305                 310                 315                 320

Cys Gly Cys Met Ile Ile Glu Asp Glu Asp Ala Pro Ile Ser Ile Thr
                325                 330                 335

Leu Asp Asp Thr Lys Pro Asp Gly Ser Leu Pro Ala Ile Met Gly Phe
                340                 345                 350

Ile Leu Ala Arg Lys Ala Asp Arg Leu Ala Lys Leu His Lys Glu Ile
            355                 360                 365

Arg Lys Lys Lys Ile Cys Glu Leu Tyr Ala Lys Val Leu Gly Ser Gln
        370                 375                 380

Glu Ala Leu His Pro Val His Tyr Glu Glu Lys Asn Trp Cys Glu Glu
385                 390                 395                 400

Gln Tyr Ser Gly Gly Cys Tyr Thr Ala Tyr Phe Pro Pro Gly Ile Met
                405                 410                 415

Thr Gln Tyr Gly Arg Val Ile Arg Gln Pro Val Gly Arg Ile Phe Phe
                420                 425                 430

Ala Gly Thr Glu Thr Ala Thr Lys Trp Ser Gly Tyr Met Glu Gly Ala
            435                 440                 445

Val Glu Ala Gly Glu Arg Ala Ala Arg Glu Val Leu Asn Gly Leu Gly
        450                 455                 460

Lys Val Thr Glu Lys Asp Ile Trp Val Gln Glu Pro Glu Ser Lys Asp
465                 470                 475                 480

Val Pro Ala Val Glu Ile Thr His Thr Phe Trp Glu Arg Asn Leu Pro
                485                 490                 495

Ser Val Ser Gly Leu Leu Lys Ile Ile Gly Phe Ser Thr Ser Val Thr
            500                 505                 510

Ala Leu Gly Phe Val Leu Tyr Lys Tyr Lys Leu Leu Pro Arg Ser
            515                 520                 525
```